US008440436B2

(12) United States Patent
Van Der Werf et al.

(10) Patent No.: US 8,440,436 B2
(45) Date of Patent: *May 14, 2013

(54) PRODUCTION OF ITACONIC ACID

(75) Inventors: Maria Johanna Van Der Werf, Tuil (NL); Martinus Petrus Maria Caspers, Rijswijk (NL); Nicole Van Luijk, Utrecht (NL); Peter Jan Punt, Houten (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 143 days.

This patent is subject to a terminal disclaimer.

(21) Appl. No.: 12/669,955

(22) PCT Filed: Jul. 21, 2008

(86) PCT No.: PCT/NL2008/050499
§ 371 (c)(1),
(2), (4) Date: Aug. 23, 2010

(87) PCT Pub. No.: WO2009/014437
PCT Pub. Date: Jan. 29, 2009

(65) Prior Publication Data
US 2010/0311132 A1 Dec. 9, 2010

(30) Foreign Application Priority Data
Jul. 20, 2007 (EP) .................................... 07112895

(51) Int. Cl.
*C12P 7/46* (2006.01)
*C12N 9/00* (2006.01)
*C12N 9/88* (2006.01)
*C12N 15/00* (2006.01)
*C07H 21/04* (2006.01)

(52) U.S. Cl.
USPC ........ 435/145; 435/183; 435/232; 435/320.1; 536/23.2

(58) Field of Classification Search ........................ None
See application file for complete search history.

(56) References Cited

U.S. PATENT DOCUMENTS
5,637,485 A    6/1997   Jarry et al.

FOREIGN PATENT DOCUMENTS
WO    WO-00/37629    6/2000

OTHER PUBLICATIONS

Lopez et al. J Biotechnol. Mar. 2, 2005;116(1):61-77. Epub Nov. 30, 2004.*
Bonnarme et al. J Bacteriol. Jun. 1995;177(12):3573-8.*
Dwiarti et al. J Biosci Bioeng. 2002;94(1):29-33.*
Bentley et al., Journal of Biological Chemistry (1957) 226(2):703-720.
Database GenBank Accession No. CH476609, Sep. 8, 2006.
Dwiarti et al., Journal of Bioscience and Bioengineering (2002) 94:29-33.
International Search Report for PCT/NL2008/050499, mailed on Dec. 12, 2008, 3 pages.
International Preliminary Report on Patentability for PCT/NL2008/050499, issued Jan. 26, 2010, 8 pages.
Kanamasa et al., Appl. Microbiol. Biotechnol. (2008) 80:223-229.
Magnuson and Lasure, "Organic Acid Production by Filamentous Fungi" in Advances in Fungal Biotechnology for Industry, Agriculture, and Medicine (2004), Lange and Lange (eds.), Plenum Publishers, pp. 307-340.

* cited by examiner

*Primary Examiner* — Christian Fronda
(74) *Attorney, Agent, or Firm* — Morrison & Foerster LLP

(57) ABSTRACT

The invention relates to the production of itaconic acid in micro-organisms by introducting into a suitable host cell a gene coding for the enzyme cis-aconitic acid decarboxylase, preferably derived from *A. terreus*. Further part of the invention are host cells, preferably from *A. niger*, provided with the above mentioned genes.

8 Claims, 9 Drawing Sheets

Fig. 2

Figure 1:
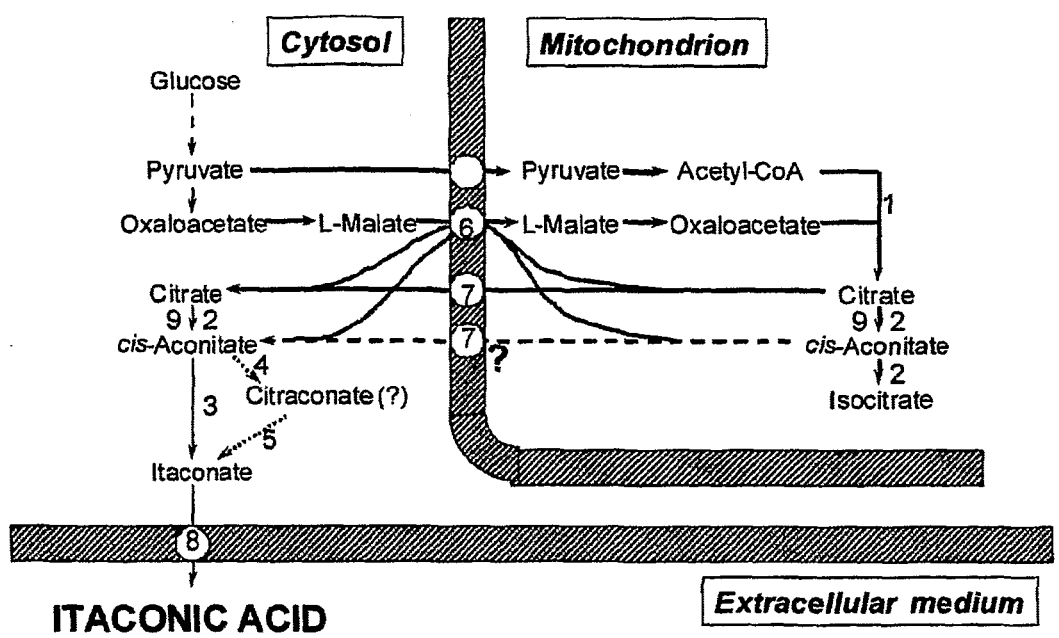

A. CAD genomic nucleotide sequence from *A. terreus*

*ATG* startcodon
TAA stop codon
Intron sequence

```
1     GTCCCTGGTG GGTCTTGAAA TCGCATGTCA CACTCATTCC GGATGAAACA CATTCCGGAG
61    CACGCGTTGA TATTGCTAAA CAGTATAGAC CCGAATGGTC TGCAGAAGCC CTAAATAGTA
121   GGTCTCATTA GCCAGCATTT AGTTGTGATT GCAGATCATT GTCAGCCTAA CATCAGTGTA
181   GGTTACGGTG TGATATTTAC TTGCATAGAA GGTTCCAGAC CACACGGTTC TAGATCCTTT
241   GACAGCAGCA TGAATGGATT GCCCTCTAGG TGCCGGGCGC CGACGTGTGT GTTGCTCCGG
301   GATTTGTAGG ACGGAGCTCG GATACCTAGC CGCTATGGGC ATCGGAGGTT GTAGCAGCGT
361   ACACACTTGG ATAGTTAAAT AATCGGGTGT ACACCCACTG TTGGAAATGA CGGGGGCCTA
421   AAAACACGAG ATTATCTGAC CCAATTTCTG TTCGTTGGCA TTCTATCATT CGCAGCGAAG
481   ATCGTCCTCT TAAATTGACC ATGACCAAGC AATCTGCGGA CAGCAACGCA AAGTCAGGAG
541   TTACGGCCGA AATATGCCAT TGGGCATCCA ACCTGGCCAC TGACGACATC CCTTCGGACG
601   TATTAGAAAG AGCGAAATAC CTGATTCTCG ATGGTATTGC ATGTGCCTGG GTTGGTGCAA
661   GAGTGCCTTG GTCAGAGAAG TATGTGCAGG CAACAATGAG CTTTGAGCCG CCAGGAGCCT
721   GCAGGGTGAT TGGATATGGG CAGGTAAGCT TTATCCAATC TAGACAGTCT ACAAAGTATA
781   CTGACGATTC TTTGTATAGA AACTGGGGCC TGTTGCAGCA GCCATGACCA ATTCCGCTTT
841   CATACAGGCC ACAGAGCTTG ACGACTACCA CAGCGAAGCC CCCTACACT CTGCAAGCAT
901   CGTCCTCCCT GCGGTCTTTG CAGCAAGTGA GGTCTTAGCC GAGCAAGGCA AAACAATTTC
961   TGGTATAGAT GTCATTCTAG CCGCCATTGT GGGGTTTGAA TCTGGCCCGC GGATCGGCAA
1021  AGCAATTTAC GGATCGGACC TCTTGAACAA CGGCTGGCAT TGTGGAGCCG TGTATGGTGC
1081  TCCAGCTGGT GCGCTGGCCA CAGGAAAGCT CCTCGGTCTA ACTCCAGACT CCATGGAAGA
1141  TGCTCTCGGA ATCGCGTGCA CGCAAGCCTG TGGTTTAATG TCGGCGCAAT ACGGAGGCAT
1201  GGTCAAGCGC GTGCAACATG GATTCGCAGC GCGTAATGGT CTTCTTGGGG GACTGTTGGC
1261  CTATGGTGGG TACGAGGCCA TGAAGGGTGT CCTGGAGAGA TCTTATGGCG GTTTCCTCAA
1321  AATGTTCACC AAGGGCAATG GCAGAGACCC TCCCTACAAA GAGGAGGAAG TGGTGGCCGG
1381  TCTCGGTTCA TTCTGGCATA CCTTTACTAT TCGCATCAAG CTCTATGCCT GCTGCGGACT
1441  TGTCCATGGT CCAGTCGAAG CTATCGAAAA GCTTCAGAGG AGATACCCCG AGCTCTTGAA
1501  TAGAGCCAAC CTCAGCAACA TTCGCCATGT TTATGTACAG CTTTCAACAG CCTCGAACAG
1561  TCACTGTGGA TGGATACCAG AGGAGAGGCC CATCAGTTCA ATCGCAGGGC AGATGAGTGT
1621  CGCATACATC CTCGCCGTCC AGCTGGTCGA CCAGCAATGT CTTCTGGCTC AGTTTCTGA
1681  GTTTGATGAC AACTTGGAGA GACCAGAAGT GTGGGATCTG GCCAGGAAGG TTACTCCATC
1741  TCATAGCGAA GAGTTTGATC AAGACGGCAA CTGTCTCAGT GCGGGTCGCG TGAGGATTGA
1801  GTTCAACGAT GGCTCTTCTG TTACGGAAAC TGTCGAGAAG CCTCTTGGAG TCAAAGAGCC
1861  CATGCCAAAC GAACGGATTC TCCACAAATA CCGAACCCTT GCGGGTAGCG TGACGGACGA
1921  ATCCCGGGTG AAAGAGATTG AGGATCTTGT CCTCAGCCTG GACAGGCTCA CCGACATTAC
1981  CCCATTGCTG GAGCTGCTTA ATTGTCCCGT GAAATCGCCA CTGGTATAA
```

B. CAD Amino acid sequence (490 aa):

```
1    MTKQSADSNA KSGVTAEICH WASNLATDDI PSDVLERAKY LILDGIACAW VGARVPWSEK
61   YVQATMSFEP PGACRVIGYG QKLGPVAAAM TNSAFIQATE LDDYHSEAPL HSASIVLPAV
121  FAASEVLAEQ GKTISGIDVI LAAIVGFESG PRIGKAIYGS DLLNNGWHCG AVYGAPAGAL
181  ATGKLLGLTP DSMEDALGIA CTQACGLMSA QYGGMVKRVQ HGFAARNGLL GGLLAYGGYE
241  AMKGVLERSY GGFLKMFTKG NGREPPYKEE EVVAGLGSFW HTFTIRIKLY ACCGLVHGPV
301  EAIEKLQRRY PELLNRANLS NIRHVYVQLS TASNSHCGWI PEERPISSIA GQMSVAYILA
361  VQLVDQQCLL AQFSEFDDNL ERPEVWDLAR KVTPSHSEEF DQDGNCLSAG RVRIEFNDGS
421  SVTETVEKPL GVKEPMPNER ILHKYRTLAG SVTDESRVKE IEDLVLSLDR LTDITPLLEL
481  LNCPVKSPLV *
```

Fig. 3

```
                    10         20         30         40         50         60
                    |          |          |          |          |          |
Aterreus_CAD        ------------------------------------------------------------
XP001209273         ------------------------------------------------------------
AAD34563            ------------------------------------------------------------
BAE66063            ------------------------------------------------------------
XP001393934         ------------------------------------------------------------
XP001389415         ------------------------------------------------------------
XP391396            ------------------------------------------------------------
XP001383451         ------------------------------------------------------------
XP001217495         MAKLLERSIAWVLYARRGHDSGLLHRSPPFAQHPSPTMTVECTIGPSESPIPPEYSAFEH
NP961187            ------------------------------------------------------------
YP880968            ------------------------------------------------------------
YP891060            ------------------------------------------------------------
ZP01648681          ------------------------------------------------------------
YP001161249         ------------------------------------------------------------

70         80         90        100        110        120
                    |          |          |          |          |          |
Aterreus_CAD        ------------------------------------------------------------
XP001209273         ------------------------------------------------------------
AAD34563            ------------------------------------------------------------
BAE66063            ------------------------------------------------------------
XP001393934         ------------------------------------------------------------
XP001389415         ------------------------------------------------------------
XP391396            ------------------------------------------------------------
XP001383451         ------------------------------------------------------------
XP001217495         GLFPTFSWTPPPNAAEYLLVVEDPDAPLAEPVVHGLYYGIPASKTSVSSTDFEPVGDDGE
NP961187            ------------------------------------------------------------
YP880968            ------------------------------------------------------------
YP891060            ------------------------------------------------------------
ZP01648681          ------------------------------------------------------------
YP001161249         ------------------------------------------------------------

130        140        150        160        170        180
                    |          |          |          |          |          |
Aterreus_CAD        ------------------------------------------------------------
XP001209273         ------------------------------------------------------------
AAD34563            ------------------------------------------------------------
BAE66063            ------------------------------------------------------------
XP001393934         -----------MVTITAKSEAASATSPISSNTITTTLNGVGDPKNKEKDLQLQEKE
XP001389415         ------------------------------------------------------------
XP391396            --------------------MSHGCIGINYRLISF-----VLTNSFPTT-------
XP001383451         -----------------------------------------MDLSLP---------
XP001217495         LRLNGGFKYGLNRRRNVYMPPRGFLGHGPHRYFYQIVALSERIEQSQLSAPATKEEVVRC
NP961187            ---------------------------------------------------------MTA
YP880968            ---------------------------------------------------------MTA
YP891060            -----------------------------------------------------------M
ZP01648681          ------------------------------------------------------------
YP001161249         ------------------------------------------------------------
```

Fig. 3, Contd.

```
                        190        200        210        220        230        240
                         |          |          |          |          |          |
Aterreus_CAD    -----MTKQS---ADSNAKSGVTAEICHWASNLATDDIPSDVLERAKYLILDGIACAWVG
XP001209273     -----MTKQS---ADSNAKSGVTAEICHWASNLATDDIPSDVLERAKYLILDGIACAWVG
AAD34563        -----MTKQS---ADSNAKSGVTAEICHWASNLATDDIPPDVLERAKYLILDGIACAWVG
BAE66063        -----MTVT-----DSTPEGNVTAELCNWVTELKPSDIPADVLQRAKHLLLDGIACGLVG
XP001393934     GEEEEISKET---KAYNSSNGVTSQLCTWIASLQLDDIPDSVRTRAKYLFLDGIACALVG
XP001389415     -----MTTLTPT-PANSTSTPITHTLSTWLEDLTPESIPVEVRERAKYLILDGLACALLG
XP391396        -YNPSMSESKP---------SPTVQLSRWVSQLKLDDIPEQVRTRAKYLILDGIACAFVG
XP001383451     -YDRKINSR----------SVTTELSEWVAQLKWEDVPDKIKDRTKFLILDGIGCALVG
XP001217495     LQDKIISMTEHSGLTTQQNNGVTRQLCSWVDRLRLADVPEDQLVRAKYLILDGIGCTIVG
NP961187        LQQETVTDP----------VGPTGLLATWVAELTLDDVPAPVVDRAKHLLLDGIGCALVG
YP880968        LQQETVTDP----------VGPTGLLATWVAELTLDDVPPPVVDRAKHLLLDGIGCALVG
YP891060        GQVNTLTDPS-------APEGPTGQLVNWVRTLEWDQVPEHVRVRAAHLLLDGIGCALVG
ZP01648681      MAGTTPTDA----------DGPTGRLATWLAETSVDAIPTEVSTRARHLILDGIGCLLVG
YP001161249     MAGTTPTDA----------DGPTGRLATWLAETSVDAIPTEVSTRARHLILDGIGCLLVG 250        260        270        280        290        300
                         |          |          |          |          |          |
Aterreus_CAD    ARVPWSEKYVQATMSFEPP-GACRVIGYG-QKLGPVAAAMTNSAFIQATELDDYHSEAPL
XP001209273     ARVPWSEKYVQATMSFEPP-GACRVIGYG-QKLGPVAAAMTNSAFIQATELDDYHSEAPL
AAD34563        ARVPWSEKYVQATMSFEPP-GACRVIGYG-QKLGPVAAAMTNSAFIQATELDDYHSEAPL
BAE66063        SHVPWSEQAAKAIDDYEPE-GYCSVIGYN-RRYGPQAAAILNGSFIQAVELDDYHSAAPL
XP001393934     ARVPWSQKAFDAMTAFEER-GKHVVIGYE-ERLGAIAAATLNGSWIQACEVDDYHSVAPL
XP001389415     ARLPWSVKAHDAITTIEGQ-GKCTVIGWN-ETLSPNAAALLNSTFLQGFDLDDIHVEAPI
XP391396        SHLPWSETAAHAIFKLEPTQGDASLVGWGGRKATALSAALLNGTFIQGFELDDWHSEAPL
XP001383451     AHLPWSEEAVEAVLKFETPGGDSPIVGWKGRKTGLVSAALLNSTFIQGFELDDYHSYAPL
XP001217495     AHLPWSEKAAHAILDMEPP-GDCPVWGYN-KKIGPLPSALVNSTAIQAFELDDWHSLAPL
NP961187        AQLPWSRIATDAVLALEGS-GDSIVIGTG-RRTSAPAAAVLNGTFIQGFELDDFHPLAPL
YP880968        AQLPWSRIATDAVLALEGS-GDSIVIGTG-RRTSAPAAAVLNGTFIQGFELDDFHPLAPL
YP891060        AQLPWSRLATDAVLGIEGD-GAVPVIGTG-RTSTPVGAVLLNSTFIQGFELDDFHPFAPL
ZP01648681      ARLPWSRIAVQS-LTVEP--GASVVAGWD-RTASAPTAVMLNSSFIQGFELDDVSYRIPW
YP001161249     ARLPWSRIAVQS-LTVEP--GASVVAGWD-RTASAPTAVMLNSSFIQGFELDDVSYRIPW 310        320        330        340        350        360
                         |          |          |          |          |          |
Aterreus_CAD    HSASIVLPAVFAASEVLAE---QGKTISGIDVILAAIVGFESGPRIGKAIYGSDLLNNGW
XP001209273     HSASIVLPAVFAASEVLAE---QGKTISGIDVILAAIVGFESGPRIGKAIYGSDLLNNGW
AAD34563        HSASIVLPAVFAASEVLAE---QGKTISGIAVILAAIVGFESGPRIGKAIYGSDLLNNGW
BAE66063        HSASVLLPALFAAAEVQSKG-HRKSVVSGLDFLVALVVGFETGPRVGSAMYGADLLSRGW
XP001393934     HSQAVVIPPLFAAAVGARDHPTTPRIIDGRTLLLASVVGFEIGPRVGMALHGTEMLAKGW
XP001389415     HTMSVILPAILAAAEQEHGG--STRPISGNDFITATVAGCETGPRVGYALGGTHMLTIGW
XP391396        HSNSIILPALIAAAQNSHST------TSGKDFLLATIAGYEIGPRVGRALWGTHVLSSGW
XP001383451     HSNSIILPTLLSLCSKDPSK------HSGRDFILATIVGFEVGPRVGKSIGGSSILSLGW
XP001217495     HSNAILLPALFAAAAHQKARG-GPAINGASLLLSTIVGYEIGPRVGLCLHGSHMLTRGW
NP961187        HSCSLLIPALLSTAATRS------ATTTGRELLLAAIAGFEVGPRVGHALHGTQMLDRGW
YP880968        HSCSLLIPALLSTAATRS------ATTTGRELLPAAIAGFEVGPRVGHALHGTQMLDRGW
YP891060        HSASLVVPALLATTAHLN------RPVSGKELLMAAIVGFETGPRIGRALGGTEMLSRGW
ZP01648681      HANAVVLPVLLAVAGLR-------GKVTGAEFLRAEVLGFETGARVGLALRGPQLVTHGW
YP001161249     HANAVVLPVLLAVAGLR-------GKVTGAEFLRAEVLGFETGARVGLALRGPQLVTHGW
```

Fig. 3, Contd.

```
                       370        380        390        400        410        420
                        |          |          |          |          |          |
Aterreus_CAD   HCGAVYGAPAGALATGKLLGLTPDSMEDALGIACTQACGLMSAQYGGMVKRVQHGFAARN
XP001209273    HCGAVYGAPAGALATGKLLGLTPDSMEDALGIACTQACGLMSAQYGGMVKRVQHGFAARN
AAD34563       HCGAVYGAPAGALATGKLLGLTPDSMEDALGIACTQACGLMSAQYGGMVKRVQHGFAARN
BAE66063       HSGPVFGSPAAAAASSKLLGLSPDDTESAVGIACTQAGGLMAAQYEGMVKRVQHAFAARN
XP001393934    HCGSVFGAPAAAGSSAKLLGLSAGQIEDAIGVAATQACGLMAAQYDGMVKRMHHGFAARN
XP001389415    HCGAIFGPAASAAAVSKLLNLPAAQIEDALGMACTQACGLMSVQFESMVKRMQHGFASRS
XP391396       HSGAVFGPAAAASSVSKLYGFSADKIEDAFGIACTQACGLMSAQFESDVKRMHHGIAARN
XP001383451    HSGAVFGPPVAAASACKFLSHNAIQIEDAFGIACTQASGLMSAQFESSVKRMQHGFAVRN
XP001217495    HSGVVFGHAASAAAVSKLLGLGSDAIEDAVGIACTQACGLMSAQFGSDVKRMQHGFAARN
NP961187       HSGPVFGTHAAAMASGKLRGLPPAQLEDALGLAGTQSAGLMAAQYEAMSKRMHHGLAARN
YP880968       HSGPVFGTHAAAMASGKLRGLPPAQLEDALGLAGTQSAGLMAAQYEAMSKRMHHGLAARN
YP891060       HSGPVFGGIGTALACGRLRGLNGEQLEDAVGFAATQSAGLMSAQYEAMGKRMQHGFAARN
ZP01648681     HSGAVFGGPGAAAAGGVLYGLTPARFEDALGIAATQSCGLMAN--EAMVKRMQHGFAARN
YP001161249    HSGAVFGGPGAAAAGGVLYGLTPARFEDALGIAATQSCGLMAN--EAMVKRMQHGFAARN 430        440        450        460        470        480
                        |          |          |          |          |          |
Aterreus_CAD   GLLGGLLAYGGYEAMKGVLERSYGGFLKMFTKGNGREPPYKEEEVVAGLGSFWHTFT-IR
XP001209273    GLLGGLLAYGGYEAMKGVLERSYGGFLKMFTKGNGREPPYKEEEVVAGLGSFWHTFT-IR
AAD34563       GLLGGLLAHGGYEAMKGVLERSYGGFLKMFTKGNGREPPYKEEEVVAGLGSFWHTFT-IR
BAE66063       GLFGALLARDGYVGIKKVFDRSYGGFLTMFTQGNGRTPQYKPEEVTTALGKEWQTTN-IR
XP001393934    GLLGTMLAWGGYEGIKKVFERPYGGFLAMFGLGSKNTPSSKPEEVAKDLGTFWHTAEWIR
XP001389415    GVLATYLAKQGFTGIKEIFDREYGGFLKMFSYGAETERKYYPEEVCKGLGEVWQTKK-IK
XP391396       GLMAAVLARDGYVGIKKVFEREYGGFLKQFSSGNGREPQYRLDELTSELGTKWQTNG-IR
XP001383451    GLFAALLADSNYKGISKVFERKYGGYIPVFTLG-GLKP--KPEEISLGLGEIWRIEG-TL
XP001217495    GLFGALLAKSGYTGIKRVFEEPYGGFLAVFGEGSGKEPPFLAEELVNGLGQTWQLDA-IR
NP961187       GFYAAGLAAAGYTGIKRVFEREYGGFLSVFGEGHDPDA----AALTADLGQRWETSL-IM
YP880968       GFYAAGLAAAGYTGIKRVFEREYGGFLSVFGEGHDPDA----AALTADLGQRWETSL-IM
YP891060       GFYSAALAQSGYTGIDQVLERPYGGFLAVYGEGHRPDA----SAITRGLGDEWETTA-IM
ZP01648681     GLVAAMLAAGGYGGTKRIFERGYGGYLTVYGAGHGPDP----SHIDDALGEHWYLRE-QT
YP001161249    GLVAAMLAAGGYGGTKRIFERGYGGYLTVYGAGHGPDP----SHIDDALGEHWYLRE-QT 490        500        510        520        530        540
                        |          |          |          |          |          |
Aterreus_CAD   IKLYACCGLVHGPVEAIEKLQRRYPELLNRANLSNIRHVYVQLSTASNSHCGWIPEERPI
XP001209273    IKLYACCGLVHGPVEAIEKLQRRYPELLNRANLSNIRHVYVQLSTASNSHCGWIPEERPI
AAD34563       IKLYACCGLVHGPVEAIENLQRNYPDRFAVDQLHNIRRITVSLSEPVFAHDGWAPEERPL
BAE66063       VKLHACVGGCHGQIEALEKLQRNYPDRFAVDQLHNIRRITVSLSEPVFAHDGWAPEERPL
XP001393934    LKLHACCGGIHGTIECLAEMQEMYPERLGREKLGEIKEIRIQLSDAVFHHCGWAPETRPL
XP001389415    QKLHALCAVSHCTVDCIKDLQAMYPAKMG--EWKKIVKIEAEMARAAMKKGGWAPE-KPA
XP391396       IKPYAAMAGTHPSIDCIRRLQEQNPERMN--KFDEITKIEILLGEAAFHHGGWKAK-KPL
XP001383451    VKLHPCMGGIHSTCECVEELVNSQEVDS-----KNIEGVKIELGKAAFHHGGWKAQ-RPI
XP001217495    VKPYASMAGTHCIIDSVAALQREYPEKLK--DLDAIVSIAIEMSEPAWKHGGWKAH-RPL
NP961187       VKSYAAMGGLHGAIDAARRLR--NSVAP-----QNISSVDITVGETVYKHGWWLPE-RPL
YP880968       VKSYAAMGGLHGAIDAARRLR--NSVAP-----QNISSVDITVGETVYKHGWWLPE-RPL
YP891060       VKSWAVMGGLHGVVEAARILR--NRLHG-----RTIEHIDIRVGDVVYHHGWWQPQ-RPL
ZP01648681     IKPYAAMGYTHPAIDAALALRAADRVDP-----AATARIEIEVADSVFDHTAFPIH-RPI
YP001161249    IKPYAAMGYTHPAIDAALALRAADRVDP-----AATARIEIEVADSVFDHTAFPIH-RPI
```

Fig. 3, Contd.

```
                    550        560        570        580        590        600
                     |          |          |          |          |          |
Aterreus_CAD   SSIAGQMSVAYILAVQLVDQQCLLAQFSEFDDNLERPEVWDLARKVTPSHSEEFDQDGN-
XP001209273    SSIAGQMSVAYILAVQLVDQQCLLAQFSEFDDNLERPEVWDLARKVTPSHSEEFDQDGN-
AAD34563       SSIAGQMSVAYILAVQLVDQQCLLAQFSEFDDNLERPEVWDLARKVTPSHSEEFDQDGN-
BAE66063       TATGGQMNAAYIGAAQLVYGQVLLDQFEP--HALDSDAVWSLIDKTTCVHSSEFDKPG--
XP001393934    TPTGAQMNTAFVAASQLVDGQVLLEQFSS--GKLDRDEIWELIGKTSCVHTTELDQPN--
XP001389415    TATAAQMSIPYAVALQVLDGEIVPGQFAP--GMLNREELWDVIRLVECREAKELDNTW--
XP391396       TATGAQMSNSFTTALQIVHRQVLMAQFTS--NMLNDERVWRLVHMTECKLYITDGDSIG-
XP001383451    NVIGAQMNNSYIAASIFVDGSLQMKSFTE--DKLNREEVWDIVKKTQCVENNFEG-QIDP
XP001217495    TATGAQMSCAYVAAVQLVDGQVLPQQFQP--EKVDRDVIWRLVDKTECFHTPELGEKYE-
NP961187       TPIGAQMNIGYATVAAALLDGNVLPEQFTA--ARLDADDIWALISATRVHLDESLADADI-
YP880968       TPIGAQMNIGYATAAALLDGNVLPEQFTA--ARLDADDIWALISATRVHLDESLADADI-
YP891060       TAIGAQMNIGYAAAVTLLDGVALPQQFTA--ERLDADDVWRLLARTHVELDESIDELPP-
ZP01648681     ESVAAQMSVRYVTAAALLDGTVSLEQLRP--ERLDRDDVWRLVDRTTVTRGSGSAS----
YP001161249    ESVAAQMSVRYVTAAALLDGTVSLEQLRP--ERLDRDDVWRLVDRTTVTRGSGSAS----

610        620        630        640        650        660
                     |          |          |          |          |          |
Aterreus_CAD   -CLSAGRVRIEFNDGSSVTETVEKPLG-VKEPMPNERILHKYRTLAGSVTDESRVKEIED
XP001209273    -CLSAGRVRIEFNDGSSVTETVEKPLG-VKEPMPNERILHKYRTLAGSVTDETRVKEIED
AAD34563       -CLSAGRVRIEFNDGSSVTETVEKPLG-VKEPMPNERILHKYRTLAGSVTDESRVKEIED
BAE66063       -HLCGARIVVEFNDGETVEDVVAMPKG-FDPPITDDEIREKWRKLASSVIDSERLQRIEN
XP001393934    -IGCGALISIAFADGSQVQHSLLKPKG-VDEPISNEEILEKFRRLTGGLIGVERQEKIER
XP001389415    --AQR--VKITFEDGEVVEKLLKAPKG-VHPGVTNEEVLQKWRAVTKGVISEERQKKIEE
XP391396       ----CQEVRIEFQDGTALHHAVQNAYG-VDPPLSNEDIVGKWRDLTKGIVENKVLDKIEE
XP001383451    QFKLCTQVTVTTKDGKEHISRVVNPKG-VLPPLTGKEIVEKFKNLTNNVITKDQQDKIIE
XP001217495    -----QRVTVAFQDGSKISRLLEAPKG-VSPPLSNEEILDKFRMFTYGLVEKERRDAIEQ
NP961187       TEKFRTDLAVTTREGTVHRARVTLPHGAPNDPVTNDEVVAKFHALADRVTSRGRAAAIER
YP880968       TEKFRTDLAVTTREGTVHRARVALPHGAPNDPVTNDEVVAKFHALADRVTSRGRAAAIER
YP891060       TERFQTHLTLTFSDGSTETASVMAPHGNPRDPVTNHEVVDKFARLVAPVMPADRAAAIQH
ZP01648681     ----QGRVRLTDVDGRTHEHRTEAPLGSVERPLGDAAIVDKYRDLTGRVVDRHRQRAIED
YP001161249    ----QGRVRLTDVDGRTHEHRTEAPLGSVERPLGDAAIVDKYRDLTGRVVDRHRQRAIED 670        680
                     |          |
Aterreus_CAD   LVLSLDRLTDITPLL-ELLNCPVKSPLV
XP001209273    LVLSLDRLTDITPLL-ELLNCPVKSPLV
AAD34563       LVLSLDRLTDISPLL-ELLNCPVKSPLV
BAE66063       SVLSLETSADVSELL-ALISGEL-----
XP001393934    AVLGMEELQDVNELI-ELLSVNVVNPLQ
XP001389415    IVLNLEEVEDVAGVLGELLREETVNVLQ
XP391396       IVLSLEELDDLSTLCDLLGQIAKSPLAE
XP001383451    TVLNLDKFD-MSCLLDSLDIDTSNPLAV
XP001217495    LVLRIEYVEDVSALEELLSGPTLSPIA-
NP961187       AVIRLDDLTD-VENLMDLLADPVAGALD
YP880968       AVIRLDDLTD-VENLMDLLADPVAGALD
YP891060       AFLGLPEVPD-VAPLVELLSGPVGRVLD
ZP01648681     LVLHLDEHRDGPAALLTLLAPAVGDALD
YP001161249    LVLHLDEHRDGPAALLTLLAPAVGDALD
```

PRODUCTION OF ITACONIC ACID

CROSS-REFERENCE TO RELATED APPLICATIONS

This application is the national phase of PCT application PCT/NL2008/050499 having an international filing date of 21 Jul. 2008, which claims benefit of European application No. 07112895.3 filed 20 Jul. 2007. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 313632008300Seqlist.txt | Jul. 19, 2012 | 121,828 bytes |

The invention relates to the field of microbial production, more specifically production of itaconic acid (itaconate), more specifically production of itaconate in micro-organisms.

Production and metabolism of itaconic acid in microbial cells has been studied extensively for several decades (Calam, C. T. et al., 1939, Thom. J. Biochem., 33:1488-1495; Bentley, R. and Thiessen, C. P., 1956, J. Biol. Chem. 226:673-720; Cooper, R. A. and Kornberg, H. L., 1964, Biochem. J., 91:82-91; Bonnarme, P. et al., 1995, J. Bacteriol. 117:3573-3578; Dwiarti, L. et al., 2002, J. Biosci. Bioeng. 1:29-33), but the metabolic pathway for itaconic acid has not been unequivocally established (Wilke, Th. and Vorlop, K.-D., 2001, Appl. Microbiol. Biotechnol. 56:289-295; Bonnarme, P. et al., 1995, J. Bacteriol. 177:3573-3578). Two complicating factors in this respect are that the biosynthesis route for itaconic acid is thought to occur both in the cytosol and the mitochondria (Jaklitsch, W. M. et al., 1991, J. Gen. Microbiol. Appl. 6:51-61) and that aconitase, the enzyme that interconverts citric acid into cis-aconitate, and vice versa, and other enzymes in the metabolic pathway have been found to be present in many isoforms in microbial cells.

Production of itaconic acid is now commercially achieved in *Aspergillus terreus*, which has physiological similarity to *A. niger* and *A. oryzae*. However, these latter two accumulate citric acid, due to the absence of cis-aconic acid decarboxylase (CAD) activity. Substrates used by these fungi include mono- and disaccharides, such as glucose, sucrose and fructose and starches, as they exist in forms which are degradable by the micro-organism, and molasses. Recently, it has been discovered that also glycerol is a useful substrate in itaconic acid production by *A. terreus* (U.S. Pat. No. 5,637,485).

The general scheme currently envisioned for itaconic acid biosynthesis is given in FIG. 1, wherein clearly the existence of the biosynthetic route both in the cytosol and the mitochondria is depicted and the putative connection between these two compartments. At several point of this scheme possibilities exist to try to improve the existing commercial production of itaconic acid in micro-organisms.

SUMMARY OF THE INVENTION

The present inventors now have elucidated the gene coding for the cis-aconitate decarboxylase enzyme and have found that overexpression of the cis-aconitate decarboxylase gene from *Aspergillus* is able to boost the production of itaconic acid. Accordingly, the invention comprises a method for the production of itaconic acid comprising overexpression of a gene coding for the enzyme cis-aconitic acid decarboxylase (CAD) in a suitable host cell. Preferably said gene is derived from *Aspergillus terreus*. The suitable host cell is preferably an *Aspergillus niger* or *A. terreus* host cell. According to a further preferred embodiment, the CAD gene is under control of its own or other promoters.

Another embodiment of the present invention is formed by a host cell wherein a gene coding for the enzyme cis-aconitic acid decarboxylase is introduced, preferably wherein said enzyme is derived from *Aspergillus terreus*. Said host cell preferably is a host cell selected from filamentous fungi, yeasts and bacteria, more preferably from *Escherichia coli*, *Aspergillus niger* and citrate- or lovastatin-producing hosts.

Further, the invention pertains to the use of the enzyme cis-aconitic acid decarboxylase for the production of itaconic acid in a suitable host cell.

Also comprised in the invention is a method as described above, wherein the production and/or transport of itaconic acid is further increased by increasing the intracellular itaconic acid, using at least one but preferably a combination of the following methods: 1. overexpression of a gene coding for a protein capable of transporting di/tricarboxylate, preferably cis-aconitate, citrate or isocitrate, from the mitochondrion to the cytosol, more preferably the dicarboxylate transporter encoded by the nucleic acid sequence of ATEG_09970.1 (SEQ ID NO:19) (see co-pending application EP 08151584); 2. a method as described above, wherein the activity of a regulator protein that comprises a zinc finger and a fungal specific transcription factor domain is modulated. Preferably said regulator protein is the protein encoded by the nucleic acid sequence of ATEG_09969.1 (SEQ ID NOS:17-18), located in the same gene cluster as the transporter of the invention; 3 overexpression of a nucleic acid sequence encoding an itaconate transporting Major Facilitator Superfamily Transporter (MFST) gene sequence (hereinafter "the itaconate transporter"). Preferably said nucleic acid comprises the ATEG_09972.1 sequence of *Aspergillus terreus* (SEQ ID NO:20) or a nucleic acid that shares more than about 70%, preferably more than about 80%, preferably more than about 90% sequence identity with the sequence of ATEG_09972.1 (SEQ ID NO:20) (as described in co-pending application EP 08152332).

LEGENDS TO THE FIGURES

FIG. 1: Postulated biosynthesis route(s) for itaconic acid in *A. terreus*. 1, Citrate synthase; 2, Aconitase; 3, cis-aconitic acid decarboxylase (itaconate-forming); 4, cis-aconitic acid decarboxylase (citraconate-forming); 5, citraconate isomerase; 6, mitochondrial dicarboxylate-tricarboxylate antiporter; 7, mitochondrial tricarboxylate transporter; 8, dicarboxylate transporter; 9, 2-methylcitrate dehydratase.

FIG. 2: Genomic nucleic acid sequence (SEQ ID NO:1) (A) and encoded amino acid sequence (SEQ ID NO:2) (B) of the *A. terreus* CAD gene. The depicted genomic sequence also shows 500 nucleotides 5' to the ATG start of the coding sequence. Further, the genomic sequence has a small intron.

FIG. 3: Sequence comparison of the CAD protein from *A. terreus* and several homologous proteins (see detailed description for the species of which the NCBI accession number is given in the figure). (SEQ ID NOS:2, 3, 15, 4, 5, 6, 7, 8, 9, 10, 13, 11, 12, and 14, in order of appearance)

Figure 4:
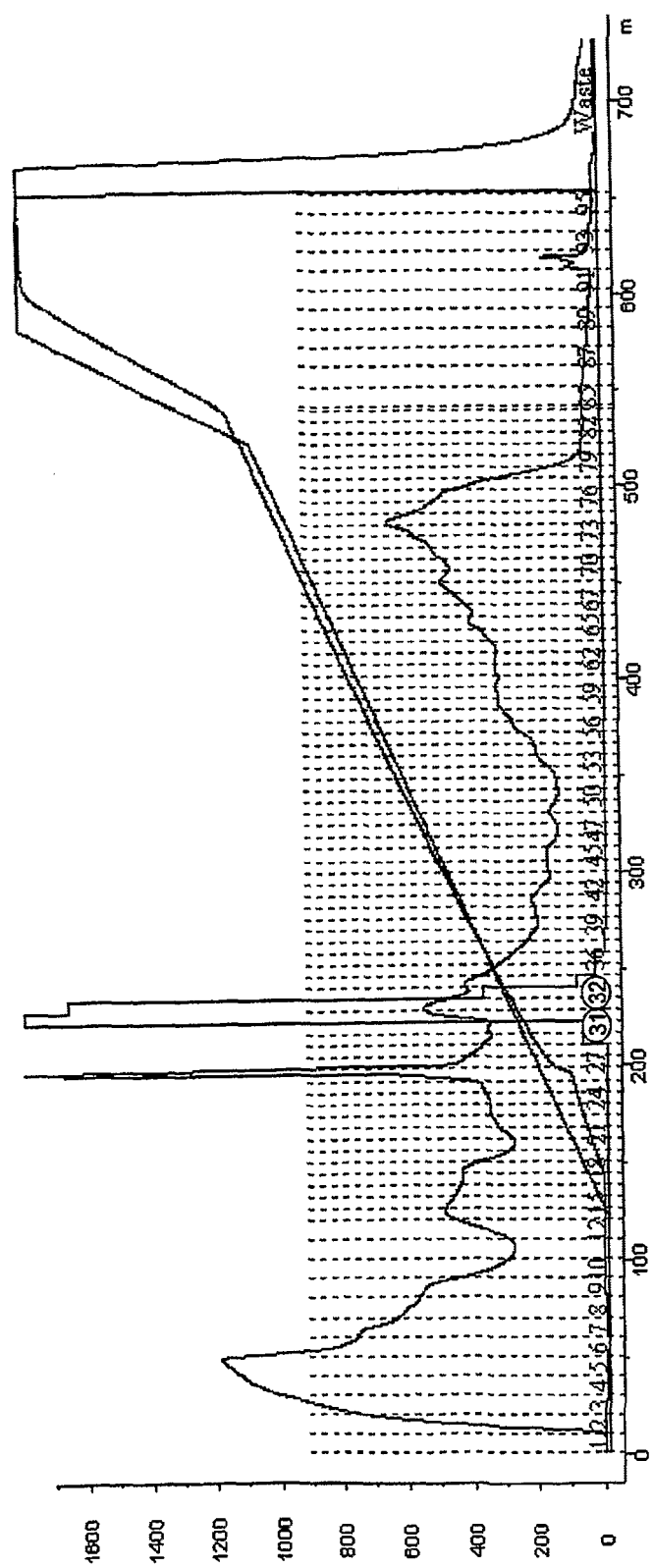

FIG. 4: Separation of proteins from a G25 chromatography desalted 35-60% ammonium sulfate pellet of cell extracts of *A. terreus* on an anion exchange Source Q15 column. Blue=OD280, black=% solution B (1 M NaCl) salt B in gradient, red=conductivity, green=CAD activity.

Figure 5:
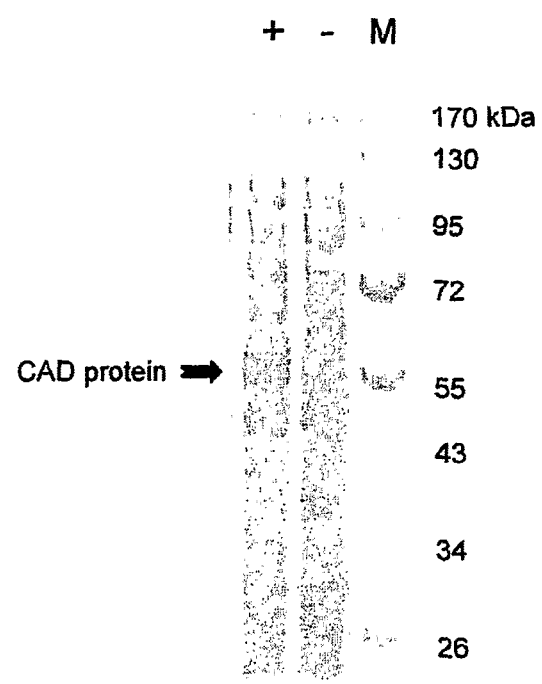

FIG. 5: SDS-PAGE of cell extract of recombinant *E. coli* containing the CAD gene on the pET52 expression vector. (+) and (−), with and without IPTG induction; M, protein markers.

Figure 6:
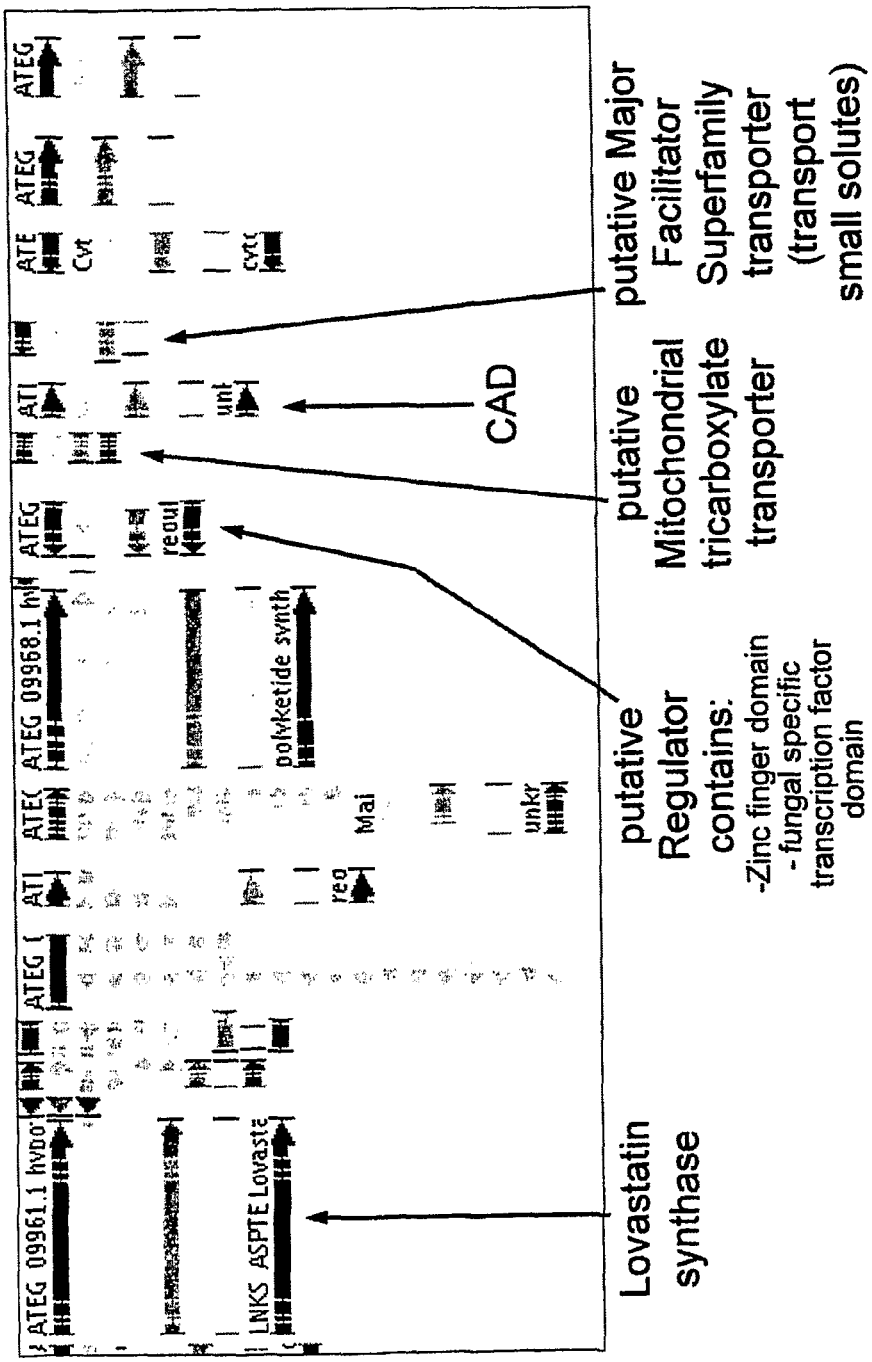

FIG. 6: Overview of *Aspergillus terreus* genome segment with the cluster of genes involved in production of itaconic acid and lovastatin ranging from ATEG 09961.1-ATEG 09975.1. The cluster contains the cis-aconitate decarboxylase (ATEG_09971.1) and the mitochondrial tricarboxylate transporter (ATEG_9970.1).

DETAILED DESCRIPTION OF THE INVENTION

"Fungi" are herein defined as eukaryotic microorganisms and include all species of the subdivision Eumycotina (Alexopoulos, C. J., 1962, In: Introductory Mycology, John Wiley & Sons, Inc., New York). The term fungus thus includes both filamentous fungi and yeast. "Filamentous fungi" are herein defined as eukaryotic microorganisms that include all filamentous forms of the subdivision Eumycotina. These fungi are characterized by a vegetative mycelium composed of chitin, cellulose, and other complex polysaccharides. The filamentous fungi used in the present invention are morphologically, physiologically, and genetically distinct from yeasts. Vegetative growth by filamentous fungi is by hyphal elongation and carbon catabolism of most filamentous fungi are obligately aerobic. "Yeasts" are herein defined as eukaryotic microorganisms and include all species of the subdivision Eumycotina that predominantly grow in unicellular form. Yeasts may either grow by budding of a unicellular thallus or may grow by fission of the organism.

The term "fungal", when referring to a protein or nucleic acid molecule thus means a protein or nucleic acid whose amino acid or nucleotide sequence, respectively, naturally occurs in a fungus.

One of the key enzymes in the biosynthetic pathway for itaconic acid is cis-aconitic acid decarboxylase (CAD). Purification and characterization of said enzyme from *Aspergillus terreus* has been reported (Dwiarti et al., 2002, J. Biosc. Bioeng. 94(1):29-33). The present inventors have followed the purification protocol and moreover have applied a transcriptomics approach. Using these approaches they have been able to identify the gene coding for CAD. The genomic sequence, along with the encoded amino acid sequence, is indicated in FIG. 2.

Also comprised in the invention are homologous proteins that are derived from other micro-organisms (also called orthologues). It will be clear for a person skilled in the art that on basis of the nucleotide sequences coding for the CAD enzyme of *A. terreus* as depicted in FIG. 2, orthologues from other micro-organism species can be easily found through database searching in NCBI GenBank based on sequence similarity and alignment analysis using minimal gap size in the alignment.

Also part of the invention are nucleotide sequences which are conservatively modified variants of the above mentioned sequences or polymorphic variants thereof. Those of skill in the art will recognize that the degeneracy of the genetic code allows for a plurality of polynucleotides to encode the identical amino acid. Such "silent variations" can be used, for example, to selectively hybridize and detect allelic variants of the nucleotide sequences of the present invention. Additionally, the present invention provides isolated nucleotide sequences comprising one or more polymorphic (allelic) variants of the above nucleotide sequences. Further part of the invention are polynucleotides still coding for a protein which has a biological function identical to the function of the CAD enzyme, which are the product of amplification from a nucleotide library using primer pairs which selectively hybridize under stringent conditions to loci within the above mentioned nucleotide sequences. The primer length in nucleotides is selected from the group of integers consisting of from at least 15 to 50. Those of skill in the art will recognize that a lengthened primer sequence can be employed to increase specificity of binding (i.e. annealing) to a target sequence. Stringent conditions in this respect means a reaction at a temperature of between 60° C. and 65° C. in 0.3 strength citrate buffered saline containing 0.1% SDS followed by rinsing at the same temperature with 0.3 strength citrate buffered saline containing 0.1% SDS.

Thus, also part of the invention are polynucleotides which selectively hybridize, under selective hybridization conditions, to one or more of the above discussed nucleotide sequences, and which code for an amino acid sequence which has a biological function similar to the function of the CAD enzyme disclosed in the present invention. Another way to indicate hybridization potential is on sequence identity. In this sense, the present invention provides also for nucleotide sequences which have a percentage of identity related to the above mentioned sequences of 40% to 95%. Thus, for example, the percentage of identity can be at least, 40%, 45%, 50%, 55%, 60%, 65%, 70%, 75%, 80%, 85%, 90%, or 95%. Sequence identity on nucleotide sequences can be calculated by using the BLASTN computer program (which is publicly available, for instance through the National Center for Biotechnological Information, accessible via the internet on http://www.ncbi.nlm.nih.gov/) using the default settings of 11 for wordlength (W), 10 for expectation (E), 5 as reward score for a pair of matching residues (M), −4 as penalty score for mismatches (N) and a cutoff of 100.

Similarly, the homology can be calculated on basis of the amino acid sequence of the enzyme encoded by said nucleotide sequences. For amino acids, the sequence identity can be calculated through the BLASP computer program (also available through http://www.ncbi.nlm.nih.gov/). On the amino acid level homologues or orthologues are defined as amino acid sequences having a biological function similar to the CAD enzyme (i.e. active in the decarboxylation of cis-acotinic acid) and having a sequence identity of at least 50%, preferably at least 55%, preferably at least 60%, more preferably at least 70%, more preferably at least 80%, more preferably at least 90%, more preferably at least 95% to the amino acid sequence of the *A. terreus* CAD enzyme as depicted in FIG. 2B.

Examples of such homologues (with NCBI numbers in brackets) are *Aspergillus terreus* (ATEG_09971 or XP_001209273 (SEQ ID NO:3)), *Aspergillus terreus* (ATEG_08909 or AAD34563 (SEQ ID NO:15) or XP_001217495 (SEQ ID NO:9)), *Aspergillus terreus* (ATEG_07260 or XP_001209946 (SEQ ID NO:16)), *Aspergillus oryzae* (BAE66063 (SEQ ID NO:4)), *Aspergillus* niger (XP_001393934 (SEQ ID NO:5)), *Gibberella zeae* (XP_391316 (SEQ ID NO:7)), *Aspergillus niger* (XP_001389415 (SEQ ID NO:6)), *Pichia stipitis* (XP_001383451 (SEQ ID NO:8)), *Mycobacterium smegmatis* (YP_891060 (SEQ ID NO:11)), *Mycobacterium avium* subsp. *pratuberculosis* (NP_961187 (SEQ ID NO:10)), *Mycobacterium avium* (YP_880968 (SEQ ID NO:13)), Salinispora arenicola (ZP_01648681 (SEQ ID NO:12)) and *Salonispora tropica* (YP_001161249 (SEQ ID NO:14)). For a sequence comparison of the sequences from these organisms with the CAD sequence of *A. terreus* (SEQ ID NO:2), see FIG. 3.

It further is contemplated that overexpression of the gene in a heterologous organism, which in nature does not or hardly produce itaconic acid, is able to provide such an organism with a functional pathway for expression of itaconic acid. Preferably such overexpression is accomplished in filamentous fungi, yeasts and/or bacteria, such as, but not limited to, *Aspergillus* sp., such as the fungi *A. terreus*, *A. itaconicus* and *A. niger*, *Ustilago zeae*, *Ustilago maydis*, *Ustilago* sp., *Candida* sp., *Yarrowia lipolytica*, *Rhodotorula* sp. and *Pseudozyma Antarctica*, the bacterium *E. coli* and the yeast *Saccharomyces cerevisiae*. Especially preferred are heterologous organisms in which the substrate cis-aconitate is available in the host organism. This cis-aconitate is formed from citric acid by either the enzyme aconitase or the enzyme 2-methylcitrate dehydratase, likely both in the cytosol and in the mitochondrion (see FIG. 1). It is submitted that this substrate is sufficiently available in *Aspergillus* strains since several aconitase-like genes have been identified on the genomes of the presently sequenced *Aspergillus* micro-organisms. Thus, other citric acid producing organisms, such as the above mentioned *Yarrowia lipolytica*, could be used for the overexpression of the CAD gene. It is further submitted that the CAD substrate cis-aconitate, or its precursor citrate, is available in large amounts in every cell, since it is part of the ubiquitous Krebs cycle. The production of itaconic acid can be further optimised by combining the overexpression of a CAD gene as described above, with overexpression of di/tricarboxylate transporters, capable of transporting, among others, cis-aconitate, citrate or isocitrate from the mitochondrion to the cytosol, preferably the gene encoded by the nucleic acid sequence of ATEG_09970.1 (SEQ ID NO:19). Overexpression of this transporter will lead to an increase in cis-aconitate in the cytosol, which can be further converted to itaconic acid.

Even further optimisation of the present invention can be achieved by modulating the activity of the regulator protein that comprises a zinc finger and a fungal specific transcription factor domain as can be found on the gene cluster that also comprises ATEG_09970 (SEQ ID NOS:19-20), wherein this regulator protein is indicated as ATEG_09969.1 (SEQ ID NO:18) (see FIG. 6). Further, overexpression of a nucleic acid sequence encoding an itaconate transporting Major Facilitator Superfamily Transporter (MFST) gene sequence (hereinafter "the itaconate transporter") enhances the production/ transport of itaconate as described herein. Preferably said nucleic acid comprises the ATEG_09972.1 sequence of *Aspergillus terreus* (SEQ ID NO:20) or a nucleic acid that shares more than about 70%, preferably more than about 80%, preferably more than about 90% sequence identity with the sequence of ATEG_09972.1 (SEQ ID NO:20) (as described in co-pending application EP 08152332).

Modulation of the activity of the (expression of the) regulator protein can be achieved by overexpression of a nucleic acid encoding said regulator protein, preferably the nucleic acid comprised in ATEG_09969.1 (as indicated in FIG. 6) when an increase in the regulator protein is intended. If a decrease in the amount of regulator protein is intended, expression of the gene can be inhibited by ways known in the art, such as anti-sense expression, sense co-suppression or RNA inhibition (RNAi).

Recently (see US 2004/0033570) it has also been established that the so-called D4B segment of *Aspergillus terreus*, which comprises amongst others the CAD gene as disclosed in FIG. 2, is responsible for the synthesis of lovastatin (see also FIG. 6). Thus, it is submitted that also these micro-organisms which are known to produce lovastatin would be suitable candidates for the production of itaconic acid. Such micro-organisms include *Monascus* spp. (such as *M. ruber, M. purpureus, M. pilosus, M. vitreus* and *M. pubigerus*), *Penicillium* spp. (such as *P. citrinum, P. chrysogenum*), *Hypomyces* spp., *Doratomyces* spp. (such as *D. stemonitis*), *Phoma* spp., *Eupenicillium* spp., *Gymnoascus* spp., *Pichialabacensis, Candida cariosilog/licola, Paecilomyces virioti, Scopulariopsis brevicaulis* and *Trichoderma* spp. (such as *T. viride*). Consequently also the CAD encoding part of the D4B segment and the enzyme with CAD activity for which it codes from these above-mentioned lovastatin producing micro-organisms are deemed to be suitable for use in the present invention.

Recombinant host cells can be obtained using methods known in the art for providing cells with recombinant nucleic acids. These include transformation, transconjugation, transfection or electroporation of a host cell with a suitable plasmid (also referred to as vector) comprising the nucleic acid construct of interest operationally coupled to a promoter sequence to drive expression. Host cells of the invention are preferably transformed with a nucleic acid construct as further defined below and may comprise a single but preferably comprises multiple copies of the nucleic acid construct. The nucleic acid construct may be maintained episomally and thus comprise a sequence for autonomous replication, such as an ARS sequence. Suitable episomal nucleic acid constructs may e.g. be based on the yeast 2µ or pKD1 (Fleer et al., 1991, Biotechnology 9: 968-975) plasmids. Preferably, however, the nucleic acid construct is integrated in one or more copies into the genome of the host cell. Integration into the host cell's genome may occur at random by illegitimate recombination but preferably the nucleic acid construct is integrated into the host cell's genome by homologous recombination as is well known in the art of fungal molecular genetics (see e.g. WO 90/14423, EP-A-0 481 008, EP-A-0 635 574 and U.S. Pat. No. 6,265,186).

Transformation of host cells with the nucleic acid constructs of the invention and additional genetic modification of the fungal host cells of the invention as described above may be carried out by methods well known in the art. Such methods are e.g. known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

In another aspect the invention relates to a nucleic acid construct comprising a nucleotide sequence encoding a CAD enzyme as defined above and used for transformation of a host cell as defined above. In the nucleic acid construct, the nucleotide sequence encoding the CAD protein preferably is operably linked to a promoter for control and initiation of transcription of the nucleotide sequence in a host cell as defined below. The promoter preferably is capable of causing sufficient expression of the CAD enzyme in the host cell. Promoters useful in the nucleic acid constructs of the invention include the promoter that in nature provides for expression of the CAD gene. Said promoter is comprised in the 500 nucleotides 5' to the coding sequence of the CAD gene, as depicted in FIG. 2A. Further, both constitutive and inducible natural promoters as well as engineered promoters can be used. Promoters suitable to drive expression of the CAD gene in the hosts of the invention include e.g. promoters from glycolytic genes (e.g. from a glyceraldehyde-3-phosphate dehydrogenase gene), ribosomal protein encoding gene promoters, alcohol dehydrogenase promoters (ADH1, ADH4, and the like), promoters from genes encoding amylo- or cellulolytic enzymes (glucoamylase, TAKA-amylase and cellobiohydrolase). Other promoters, both constitutive and inducible and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the CAD gene is homologous to the host cell in which the CAD protein is expressed.

In the nucleic acid construct, the 3'-end of the nucleotide acid sequence encoding the CAD enzyme preferably is operably linked to a transcription terminator sequence. Preferably the terminator sequence is operable in a host cell of choice. In any case the choice of the terminator is not critical; it may e.g. be from any fungal gene, although terminators may sometimes work if from a non-fungal, eukaryotic, gene. The transcription termination sequence further preferably comprises a polyadenylation signal.

Optionally, a selectable marker may be present in the nucleic acid construct. As used herein, the term "marker" refers to a gene encoding a trait or a phenotype which permits the selection of, or the screening for, a host cell containing the marker. A variety of selectable marker genes are available for use in the transformation of fungi. Suitable markers include auxotrophic marker genes involved in amino acid or nucleotide metabolism, such as e.g. genes encoding ornithine-transcarbamylases (argB), orotidine-5'-decarboxylases (pyrG, URA3) or glutamine-amido-transferase indoleglycerol-phosphate-synthase phosphoribosyl-anthranilate isomerases (trpC), or involved in carbon or nitrogen metabolism, such e.g. niaD or facA, and antibiotic resistance markers such as genes providing resistance against phleomycin, bleomycin or neomycin (G418). Preferably, bidirectional selection markers are used for which both a positive and a negative genetic selection is possible. Examples of such bidirectional markers are the pyrG (URA3), facA and amdS genes. Due to their bidirectionality these markers can be deleted from transformed filamentous fungus while leaving the introduced recombinant DNA molecule in place, in order to obtain fungi that do not contain selectable markers. This essence of this MARKER GENE FREE™ transformation technology is disclosed in EP-A-0 635 574, which is herein incorporated by reference. Of these selectable markers the use of dominant and bidirectional selectable markers such as acetamidase genes like the amdS genes of *A. nidulans, A. niger* and *P. chrysogenum* is most preferred. In addition to their bidirectionality these markers provide the advantage that they are dominant selectable markers that, the use of which does not require mutant (auxotrophic) strains, but which can be used directly in wild type strains.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g. be based on the yeast 2μ or pKD1 (Fleer et al., 1991, Biotechnology 9: 968-975) plasmids. Alternatively the nucleic acid construct may comprise sequences for integration, preferably by homologous recombination (see e.g. WO98/46772). Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987).

In a further aspect the invention relates to fermentation processes in which the transformed host cells of the invention are used for the conversion of a substrate into itaconic acid. A preferred fermentation process is an aerobic fermentation process. The fermentation process may either be a submerged or a solid state fermentation process.

In a solid state fermentation process (sometimes referred to as semi-solid state fermentation) the transformed host cells are fermenting on a solid medium that provides anchorage points for the fungus in the absence of any freely flowing substance. The amount of water in the solid medium can be any amount of water. For example, the solid medium could be almost dry, or it could be slushy. A person skilled in the art knows that the terms "solid state fermentation" and "semi-solid state fermentation" are interchangeable. A wide variety of solid state fermentation devices have previously been described (for review see, Larroche et al., "Special Transformation Processes Using Fungal Spores and Immobilized Cells", Adv. Biochem. Eng. Biotech., (1997), Vol 55, pp. 179; Roussos et al., "Zymotis: A large Scale Solid State Fermenter", Applied Biochemistry and Biotechnology, (1993), Vol. 42, pp. 37-52; Smits et al., "Solid-State Fermentation-A Mini Review, 1998), Agro-Food-Industry Hi-Tech, March/April, pp. 29-36). These devices fall within two categories, those categories being static systems and agitated systems. In static systems, the solid media is stationary throughout the fermentation process. Examples of static systems used for solid state fermentation include flasks, petri dishes, trays, fixed bed columns, and ovens. Agitated systems provide a means for mixing the solid media during the fermentation process. One example of an agitated system is a rotating drum (Larroche et al., supra). In a submerged fermentation process on the other hand, the transformed fungal host cells are fermenting while being submerged in a liquid medium, usually in a stirred tank fermenter as are well known in the art, although also other types of fermenters such as e.g. airlift-type fermenters may also be applied (see e.g. U.S. Pat. No. 6,746,862).

Preferred in the invention is a submerged fermentation process, which is performed fed-batch. This means that there is a continuous input of feed containing a carbon source and/or other relevant nutrients in order to improve itaconic acid yields. The input of the feed can, for example, be at a constant rate or when the concentration of a specific substrate or fermentation parameter falls below some set point.

EXAMPLES

Example 1

Purification of CAD

Spores 5×10⁸ were inoculated into 100 ml medium (glucose 20 g/L (pre-culture), 100 g/L (production culture); 2.0 g/L NH$_4$NO$_3$; 0.08 g/L KH$_2$PO$_4$; 1 g/L MgSO$_4$*7H$_2$O; 10 g/L CaCl$_2$*2H$_2$O; 15 mg/L CuSO$_4$*5H$_2$O; 1.7 mg/L Fe(II)SO$_4$*7H$_2$O; pH 3.1) and incubated at 30° C. for 48 h on a rotary shaker at 250 rpm. Of the preculture 8 ml was used per 200 ml in 1 L Erlenmeyer flasks for the production culture. Then the mycelium was collected from the broth by filtration and washed with 0.2 M sodium phosphate buffer (pH 6.5). Batches of ±5 g were frozen in liquid nitrogen and stored at −80° C.

Twenty grams of mycelium obtained from 2 liter production culture was ground with a pestle under liquid nitrogen in a pre-chilled mortar. The mycelium powder was suspended in 160 ml of 0.2 M sodium phosphate (pH 6.5), 1 mM EDTA, 1 mM DTT, 1 mM PMSF and 1.0 µg/ml pepstatin A. The suspension was subsequently centrifuged for 10 minutes (10.000 g) at 4° C. After ammonium sulphate precipitation (35-60% saturation) the precipitated protein fraction was resuspended and desalted on a G25 gel filtration column in 16 ml of 50 mM sodium phosphate buffer (pH 6.5), 30% glycerol, 1 mM EDTA, 1 mM DTT and 1.0 µg/ml pepstatin A (CAD buffer). After desalting the pooled, protein containing fractions (high molecular weight material), were diluted with CAD buffer to ±38 ml and supplied to a 23 ml Source 15Q ion-exchange resin, packed in an HR 16/10 column. This column was eluted with a linear gradient of 0-0.6 M NaCl in 400 ml CAD buffer, followed by a gradient of 0.6-1 M NaCl in 60 ml CAD buffer with a speed of 6 ml/min. Fractions of 10 and 6 ml were collected and cooled on ice. Analysis showed that two fractions contained approximately 4.5 mg protein of which 2.6 mg CAD (purity±60%).

Approximately 4.5 ml of one of the fractions was desalted on a G25 gel filtration column, after which the desalted, high molecular weight material was bound to a 1 ml Source 15Q column in CAD buffer and subsequently eluted with a steep gradient of 1 M NaCl in CAD buffer. The eluted active fractions were pooled and applied to a 24 ml Superdex 75 (14 µm) resin, packed in an HR 10/30 column. The column was eluted with CAD buffer with 0.15 M NaCl, with a speed of 0.2 ml/min (see FIG. 4). The fractions showing the highest specific CAD activity were analyzed through gel electrophoresis using SDS-PAGE (8-16% gradient). An abundant band at approximately 55 kDa was observed. This band was isolated from the gel for N-terminal sequencing. For ESI/MS/MS analysis the gel was first blotted onto a PVDF membrane from which the 55 kDa protein band was subsequently isolated. N-terminal sequencing and MS/MS data both reveal the hypothetical protein from *A. terreus*, having homology to prpD (ATEG_09971).

Example 2

Enzymatic Activity Analysis

During the isolation as described in Example 1 the isolated fractions were subjected to enzymatic activity assays for determining the presence/activity of the CAD protein. A sample of the fractions was incubated at 37° C. for 30 min in 0.2 M sodium phosphate with 19 mM cis-aconitic acid at pH 6.2. The enzyme reaction was terminated by addition of strong acid (HCl to a final concentration of ±1 M). The following Table indicates the concentrations of itaconate in the samples and control samples (control samples are treated according to the above assay, but without addition of the substrate cis-aconitic acid to determine the background itaconate level).

Analysis was performed with a reversed phase HPLC, using a Develosil™ 3 µm RP-Aqueous C30 140A column at a constant temperature of 25° C., with alution with 20 mM NaH$_2$PO$_4$, pH 2.25 and acetonitril. Detection was performed by UV 210 nm. Retention time of the cis-aconitate was 10.89 min, the trans-aconitic acid 16.11 min and itaconic acid 18.82 min.

| sample | Itaconate in µg/ml | Control itaconate |
|---|---|---|
| Crude extract after grinding (total volume 175 ml, 160 µl in assay) | 239.7 | 35.8 |
| Resuspended 35-60% ammonium sulphate fraction (total volume 16 ml, 160 µl in assay) | 1296.7 | 17.1 |
| Desalted fractions prior to ion-exchange | 1092.9 | |

Example 3

Construction of Micro-Array

An anonymous clone/EST-based array approach was taken according to the following scheme:

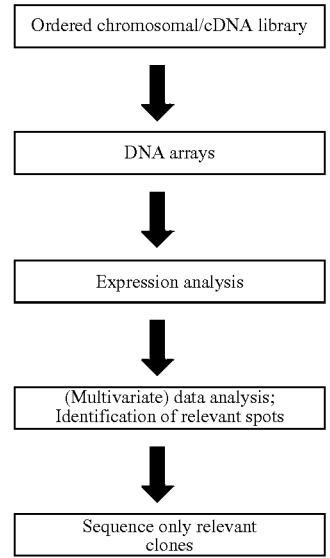

An *A. terreus* micro-array was made composed of a clone-based and an EST-based array.

Materials and Methods Construction Micro-Array

Isolation of Chromosomal DNA from *A. terreus*

*A. terreus* was cultivated overnight in a shake flask in enriched minimal medium at 33° C. and 250 rpm. Enriched minimal medium (pH 5.5) is mineral medium (MM) supplemented with 0.5% yeast extract and 0.2% casamino acids. The composition of MM was: 0.07 M NaNO$_3$, 7 mM KCl, 0.11 M KH$_2$PO$_4$, 2 mM MgSO$_4$, and 1 ml/l of trace elements (1000*stock solution: 67 mM $ZnSO_4$, 178 mM $H_3BO_3$, 25 mM $MnCl_2$, 18 mM $FeSO_4$, 71 mM $CoCl_2$, 6.4 mM $CuSO_4$, 6.2 mM $Na_2MoO_4$, 174 mM EDTA).

Mycelium was harvested after 22 hours and frozen in liquid nitrogen. Chromosomal DNA was isolated from 4.5 g mycelium following the protocol described below.

Grind 0.5-1.0 g mycelium under liquid nitrogen using the membrane disrupter.

Place polypropylene tubes (Greiner) with 1.5 ml water-saturated phenol, 1 ml TNS, 1 ml PAS and as ml 5×RNB in a water bath at 55° C., add the still frozen mycelium to the tubes and vortex every 20 seconds for totally 2-4 minutes.

TNS: triisopropyl naphthalene sulphonic acid, 20 mg/ml in water, freshly prepared PAS: 4 aminosalisylic acid, 120 mg/ml in water, freshly prepared 5×RNB: 60.55 g Tris, 36.52 g NaCl, 47.55 g EGTA in 500 ml water (pH=8.5)

Add 1 ml sevag and vortex with intervals for another 1-2 minutes.

Spin for 10 min. in the tabletop centrifuge at 4° C. at maximum velocity.

Extract the water-phase once again with phenol-sevag and twice with sevag. GENTLY, AVOID SHEARING!

Precipitate the DNA with 2 volumes ethanol. Spin directly for 10 min. in the tabletop centrifuge.

Drain the tube, dry it with Kleenex and resuspend the pellet in 500 µl Tris/EDTA. Transfer to a microvial.

Extract with phenol-sevag until interface stays clean. Then extract once with sevag.

Precipitate with 2 volumes ice-cold ethanol, spin down and resuspend the pellet in 100-200, µl TE with 50 µg/ml RNase.

Construction of Clone-Based gDNA Library

The gDNA library was prepared as follows:

Chromosomal *A. terreus* DNA was sheared into fragments of size 1.5-2.5 kb

The sheared DNA was subsequently size fractionated, end-repaired (Lucigen), and ligated into blunt-end pSMART-HC-Amp vectors (Lucigen).

The ligated constructs were transformed into *E. coli* DH 10b

Colony PCR was performed on 96 transformants to check that >90% of the inserts had the correct size Sequence analysis (short run) was performed on 20 clones to confirm their diversity and fungal origin Colony picking of 20,000 amp-resistant colonies was carried out into 96-well microtiter plates containing TY medium+100 µg/ml ampicillin The 20.000 clones were replicated into 96-well microtiter plates. The ordered libraries are stored as glycerol stocks at −80° C.

Generation of mRNA for cDNA Library Construction

Precultures: *A. terreus* spores $10^6$-$10^7$/ml) were inoculated into 100 ml B medium (2 g/l NH4NO3; 1 g/l MgSo4*7H2O; 0.008 g/l ZnSO4*7H20; 0.015 g/l CuSO4*5H2O; 1.5 ppm FeSO4*5H2O; 0.08 g/l KH2PO4; 10 g/l CaCl2*2H2O, set to pH 3.1 with HCl) containing 20 g/l glucose, and incubated for 24-48 hours at 37° C. at 250 rpm. Production cultures (B medium containing 100 g/l glucose) were inoculated 1/10 (v/v) for 2-days cultivations and 1/25 (v/v) for 3-day cultivations. After 2-3 days cultivation mycelium was harvested, filtered over miracloth, washed with 0.2 M sodium phosphate buffer (pH 6.5), frozen in liquid nitrogen and stored at −80° C.

Isolation of mRNA from *A. terreus* grind mycelium with mortar and pestle under liquid nitrogen; add 100 µl β-mercaptoethanol before grinding to inactivate RNAse transfer powder to cooled plastic tube (1.0 g per tube); keep mycelium frozen add 4 ml Trizol and vortex till homogenous add 0.4 ml chloroform and vortex centrifuge for 20-30 min. at 3700 rpm, 4° C.

transfer supernatant to Eppendorf tubes (1.2 ml per tube)

add 0.7 ml per 1.2 ml supernatant centrifuge in eppendorf centrifuge for 15 min. at 14.000 rpm, 4° C.

wash pellet with 1 ml 70% ethanol centrifuge 5 min., 14.000 rpm, 4° C.

air-dry pellet and resuspend in 0.2 ml water store RNA samples at −80° C.

Construction of cDNA Library

The cDNA library was prepared as follows:

The RNA was run on gel to determine the quality of the sample polyT-primed cDNA was prepared from the total RNA provided (RT-PCR reaction using superscript and dT primers The cDNA was size fractionated to give fragments of size 1.0-1.5 kb The fragments were end-repaired (Lucigen), and ligated into blunt-end pSMART-HC-kan vectors (Lucigen).

Restriction analysis of 96 clones was performed to check the insert size and the % of transformants which had the correct insert size Sequence analysis (short run) of 20 clones was performed to confirm diversity and fungal origin 5,000 kanamycin-resistant colonies were picked into microtiter plates The 5000 cDNA clones were replicated into 96-well microtiter plates. The ordered libraries were stored as glycerol stocks at −80° C.

Construction of the *A. terreus* Clone-Based Array

PCR fragments were generated from the different clones from the gDNA (20,000 clones) and cDNA (5,000 clones) library by mass 96 well PCR (50 µl/well, Lucigen SMART-SR1/SL1 primers with 5'-C6-aminolinkers, SuperTaq and buffer from HT Biotech. Ltd, dNTP's (Roche 11 969 064 001), pintool dipped template from grown colony plates).

All above PCR products were purified by 96 well precipitation (isopropanol and 96% ethanol wash), speedvac dried, dissolved in 15 µl 3×SSC/well and spotted with quill pins (Telechem SMP3) on CSS100 silylated aldehyde glass slides (Telechem, USA) using a SDDC2 Eurogridder (ESI, Canada). During spotting, aminolinkers of PCR products will covalently link with aldehyde groups of the coated slides.

gDNA and cDNA PCR products were spotted on two separate slides (slide a: 1st 10,000 gDNA's+5000 cDNA's; slide b: 2nd 10,000 gDNA's+same 5000 cDNA's).

For the clone-based array a genomic library was constructed. A total of 20,000 clones containing chromosomal fragments was generated, 90% of which had an average insert size of 1.5-2.5 kb. This resulted in a full genome coverage of 64% (Akopyants, N. S. et al., Mol. Biochem. Parasitol. 113: 337-340, 2001).

For the EST-based array a cDNA library of in total 5000 cDNA clones was constructed, 70% of which had an average insert size of 1.0-1.5 kb. This so-called EST-based approach has the advantage that it will be enriched for the genes expressed under the selected (itaconic acid producing) conditions, Moreover, in the EST-based approach per clone (and thus spot) only a single gene is represented in eukaryotes.

The complete micro-array, thus consisting of 20,000 genomic DNA clones and 5,000 cDNA clones was composed of an A and a B glass slide. Both slides contained the same 5,000 cDNA spots. The A and B slide each contained 10,000 of the gDNA spots.

Example 4

Generation of the Different RNA Samples by Fermentation

Materials and Methods Fermentation and mRNA Isolation
Fermentation Conditions of *A. terreus*

5-Liter controlled batch fermentations were performed in a New Brunswick Scientific Bioflow 3000 fermentors. The following conditions were used unless stated otherwise:
37° C.
pH start 3.5 set point 2.3
DO set points Day 1: 75%
  Day 2, 3, 4: 50%
  Subsequent days: 25%
Preculture: 100 ml of the same medium as used in the fermentation medium ($10^7$ spores/ml) in 500 ml Erlenmeyer flask with baffles, overnight, 37° C., 150 rpm
pH control: 4M KOH (Base), 1.5 M $H_3PO_4$(Acid)
Antifoam: Struktol (Schill & Seilacher)
Fermentation Medium Compositions:
Per litre: 2.36 g of $NH_4SO_4$, 0.11 g of $KH_2PO_4$, 2.08 g of $MgSO_4*7H_2O$, 0.13 g of $CaCl_2*2H_2O$, 0.074 g of NaCl, 0.2 mg of $CuSO_4*5H_2O$, 5.5 mg of Fe(III) $SO_4*7H_2O$, 0.7 mg of $MnCl_2*4H_2O$ and 1.3 mg of $ZnSO_4*7H_2O$ and 100 g of glucose as a carbon source.
All media were prepared in demineralised water.
Isolation of mRNA from *A. terreus*
See mRNA isolation protocol described in Example 1
Determination of the Itaconate Concentration by HPLC 5 µl of a 10-times diluted supernatant sample (split ratio 1:3) was separated using a Waters 2695 Separations module on a reversed-phase Develosil 3 µm RP-Aqueous C30 140A column (150×3 mm) (Phenomenex p/n CH0-6001) at 25° C. using the solvent gradient profile (flow rate was 0.4 ml/min) shown in Table 1.

TABLE 1

Solvent gradient of the RP-UV method.

| Time (min) | A (20 mM $NaH_2PO_4$ pH 2.25) (%) | B (Acetonitril) (%) |
|---|---|---|
| 0 | 100 | 0 |
| 10 | 100 | 0 |
| 15 | 95 | 5 |
| 20 | 95 | 5 |
| 21 | 100 | 0 |
| 30 | 100 | 0 |

Compounds were detected by UV at 210 nm using a Waters 2487 Dual wavelength Absorbance detector (Milford, MA, USA).

Itaconate Productivity

Itaconate productivity at a certain time point was calculated as the slope of the regression line between that particular time point and the time points right before and after that time point. To this end of 6-10 supernatant samples of the different fermentations, the itaconate concentrations were determined by HPLC.

For the transcriptomics approach it is essential to have RNA samples from fermentations that result in the production of different amounts of itaconate. Therefore a literature survey was performed in order to identify medium components and/or physicochemical conditions that affect the amount of itaconate produced by *A. terreus*. Although many conflicting reports were found regarding the effect that a specific parameter has on itaconic acid production, 4 key overall parameters were identified from this literature survey, i.e. (i) carbon source, (ii) pH, (iii) trace element (i.e. Mn) concentration and (iv) oxygen tension. Fermentations with *A. terreus* varying principally in these four parameters were performed on a mineral salts medium to ensure that the elemental limitations required for itaconate production would be achieved. Table 2 presents an overview of the fermentations performed in this study.

As shown in Table 2, a considerable variation in the amount of itaconate is produced in this set of fermentations, ranging from almost no itaconate (fermentation #11; pH 4.5) to about 50 g/l itaconate (#8 and #12; $O_2$ set point 25% and 10% respectively).

Of each fermentation 2 to 5 samples were harvested for isolation of mRNA.

TABLE 2

Overview of the fermentations performed in order to generate RNA samples for transcriptome analysis. The reference fermentation is on 100 g/l glucose, dO2, day 1, 75%, day 2-4, 50%, day 5 and further 25%, pH start 3.5, set point at 2.3.

| Fermentation run | Fermentation | Environmental condition | Max. Itaconic acid (g/l) | Max. Biomass (gDWT/kg) |
|---|---|---|---|---|
| First Run | 1 | Glucose (100 g/l) (control) | 16.1 | 12.7 |
| | 2 | Fructose as C-source | 8.84 | 13.7 |
| | 3 | Maltose as C-source | 13.9 | 12.1 |
| Second run | 4 | Glucose (100 g/l) pH start 3.5, set point 2.3 (control) | 25.8 | 11.6 |
| | 5 | pH set 3.5 | 8.7 | 16.5 |
| | 6 | pH start 3.5 no set point | 30.6 | 8.7 |
| Third run | 7 | Low glucose (30 g/l) | 11.1 | 6.7 |
| | 8 | $O_2$ set point 25% | 47.2 | 12.0 |
| | 9 | 5* higher Mn | 20.3 | 13.8 |
| Fourth run | 10 | Glucose (100 g/l) (control) | 26.9 | 17.9 |
| | 11 | pH set 4.5 | 0.1 | 20.4 |
| | 12 | $O_2$ set point 10% | 52.9 | 10.6 |

From in total 23 fermentation samples mRNA could be isolated. Of 7 samples, mRNA was isolated twice independently. It proved to be especially difficult (impossible) to extract RNA from the samples taken in the stationary phase. A number of samples showed partial degradation of the RNA. Although no mRNA could be isolated from the samples from fermentations #6 and #12, the remaining samples still covered the complete range of itaconate production (Table 3).

TABLE 3

List of 30 mRNA samples from various fermentation conditions that were used for transcriptome analysis. The samples marked with asterisk were the samples used for the differential expression data analysis.

| Sample no. | Fermentation condition | RNA id | EFT (hours) | Itaconic acid (g/l) | Productivity | RNA quality |
|---|---|---|---|---|---|---|
| R3 | gluc100 | 1.3.a | 50.3 | 14.6 | 0.117 | ok |
| R4 | gluc100 | 1.4.a | 74.8 | 16.1 | 0.060 | ok |
| R5 | fruc100 | 2.3.a | 50.3 | 8.2 | 0.082 | ok |
| R6 | fruc100 | 2.3.b | 50.3 | 8.2 | 0.082 | ok |
| R7 | fruc100 | 2.4.a | 75.05 | 8.6 | −0.013 | ok |
| R8 | malt100 | 3.3.a | 50.3 | 7 | 0.355 | ok |
| R9 | malt100 | 3.4.a | 75 | 12.1 | 0.220 | ok |
| R10 | pH-i3.5 | 4.3.a | 53.25 | 25.8 | 0.146 | part degr |
| R11 | pH-i3.5 | 4.3.b | 53.25 | 25.8 | 0.146 | part degr |
| R12 | pH-i3.5 | 4.4.a | 73 | 24 | −0.153* | ok |
| R13 | pH-c3.5 | 5.3.a | 53.5 | 7.5 | −0.042 | ok |
| R14 | pH-c3.5 | 5.3.b | 53.5 | 7.5 | −0.042 | ok |
| R15 | pH-c3.5 | 5.4.a | 73.25 | 7.9 | 0.035 | ok |
| R16 | gluc30 | 7.2.a | 30.25 | 9 | 0.317 | ok |
| R1 | gluc30 | 7.3.a | 43.5 | 10 | 0.030 | ok |
| R17 | gluc30 | 7.3.a | 43.5 | 10 | 0.030 | ok |
| R18 | O2s25% | 8.2.a | 30.5 | 36* | 0.824* | ok |
| R19 | O2s25% | 8.4.a | 78.25 | 46 | 0.029 | part degr |
| R20 | 5xMn | 9.2.a | 30.75 | 1 | 0.194 | ok |
| R21 | 5xMn | 9.2.b | 30.75 | 1 | 0.194 | ok |
| R22 | 5xMn | 9.3.a | 53.5 | 10 | 0.496 | part degr |
| R23 | 5xMn | 9.3.b | 53.5 | 10 | 0.496 | part degr |
| R24 | 5xMn | 9.4.a | 78.5 | 19 | 0.189 | part degr |
| R25 | 5xMn | 9.4.b | 78.5 | 19 | 0.189 | part degr |
| R26 | 5xMn | 9.5.a | 93.25 | 20 | 0.106 | ok |
| R2 | Gluc100 | 10.3.a | 51.5 | 14.7 | 0.256 | ok |
| R27 | Gluc100 | 10.3.a | 51.5 | 14.7 | 0.256 | ok |
| R28 | Gluc100 | 10.4.a | 74 | 19.5 | 0.085 | ok |
| R29 | Gluc100 | 10.5.a | 100.4 | 22 | 0.177 | part degr |
| R30 | Gluc100 | 10.5.b | 100.4 | 22 | 0.177 | part degr |
| R31 | pH4.5 | 11.3.a | 51.5 | 0.04* | −0.001 | ok |
| R32 | pH4.5 | 11.4.a | 74 | 0.05* | 0.003 | ok |

Example 6

Transcriptome Analysis, Data Analysis of the Array Data

Materials and Methods Transcriptome Analysis, Data Normalization and Data Analysis
Labelling of RNA and gDNA Total RNA's (5 μg/30 μl reaction), isolated from various *A. terreus* cultures (strain NRRL 1960, BASF) with differential itaconate production, were labelled with amino-allyl-dUTP (0.75 μM aa-dUTP final conc., Sigma A0410), using 3 μl 50 μM oligo p (dT)$_{15}$ primer (La Roche, 814270), unlabelled dNTP's (added to 1.25 μM final conc. for each dNTP), 2 μl Superscript II Reverse Transcriptase and buffer (Life Technologies, 10297-018: primer annealing 10 min 70° C., transcriptase 180 min 42°). After RNA hydrolysis (3 μl 2.5M NaOH, 30 min 37°, 3 μl 2.5 M HAc) the aa-dUTP labelled cDNA was directly purified (below).

As a reference for correcting slide differences (spotting, labeling-, hybridization- and scan efficiency), gDNA (0.5 μg/reaction) of *Aspergillus terreus* (strain NRRL 1960, BASF) was labelled with aa-dUTP, using dNTP's (conc. as above), Klenov-DNA Polymerase and buffer (Bioprime kit, Invitrogen 18094-011: primer annealing 5 min 96° C., polymerase 90 min 37 °.

The aa-dUTP-labelled cDNA or gDNA was purified (QIAquick column, Qiagen 28106), speedvac dried, dissolved (4.5 μl 0.1 M Na$_2$CO$_3$), coupled with 4.5 μl Cy5-NHS-ester for cDNA, or 4.5 μl Cy3-NHS-ester for gDNA (Amersham/GE-Healthcare PA25001 or PA23001 respectively, each in 73 μl DMSO) for 60 min at 20° C., diluted with 10 μl of water, and again purified on Autoseq G50 columns (GE-Healthcare 27-5340).

Array Blocking, (pre) hybridization and Image Analysis

Before hybridization with the array produced as described above, slides were blocked (removal surplus of spotted PCR products and blocking of free aldehyde groups) by 3× quickly washing (20° C.) with Prehyb buffer and 45 min incubation (42° C.) in PreHyb buffer (5×SSC, 1% BSA, 0.1% SDS). After 4 washes in water, spotted PCR products were denatured by dipping the slides 5 sec in boiling water and drying them with a N$_2$-gas-pistol.

The Cy5- and Cy3-labelled sample were combined, 8 μl 25 μg/μl yeast tRNA (Invitrogen, 15401-029) and 4 μl 5 μg/μl poly-dA/dT (Amersham 27-7860) were added, the mixture was speed vac dried, dissolved in 160 μl Easyhyb buffer (Roche, 1 796 895), denatured (2 min, 96° C.), cooled to 50° C., applied on a pair of prehybridised slides (a+b, 80 μl/slide) prewarmed at 50° C., covered with a cover slide (Hybri slibs, Mol. Probes. H-18201) and incubated overnight at 42° C. in a humidified hybridization chamber (Corning 2551). Slides were washed (pair a+b in one 50 ml tube, 1× in 1×SSC/0.1% SDS 37° C., 1× in 0.5×SSC 37° C., 2× in 0.2×SSC 20° C.) and dried with N$_2$-gas. All pre-hybridisation buffers were 0.45 μm filtered to reduce dust noise. Slide images of Cy5- and Cy3-fluorescence intensity (ScanArray Express Scanner & Software, Packard Biosc.) were analysed (Imagene 5.6 Software, Biodiscovery) to obtain for each spot signal- and local background value (medians) for the hybridized Cy5-RNA and Cy3-reference gDNA. These values were used for further data analysis.

Array Data Normalization

Before normalization, all low abundant spots having a Signal/Background below 1.5 were removed. Data were normalized using a total cDNA signal correction. For each slide and each spot, the difference between signal and background was calculated for Cy5 and Cy3. Per slide, the sum of the differences was taken for Cy5 and Cy3, and the ratio between these two was used as normalisation factor for that particular slide. All spots (chromosomal and genomic) were normalised using this total cDNA signal.

Data Analysis of the Transcriptomics Data by Differential Expression Analysis

The differential expression value was calculated by dividing the Cy5(RNA)/Cy3 (gDNA) ratio of a spot in the slide with the highest titer or productivity by the Cy5(RNA)/Cy3 (gDNA) ratio of that same spot in the slide with the lowest titer or productivity. The samples used for the differential expression analysis are marked in Table 2. The spots were subsequently ranked based on this ratio or, when the ratio was <1, i.e. in the case of down-regulated genes, on 1/ratio.

Sequence Analysis of Spots Selected after Transcriptomics Approach

The relevant clones were selected from the glycerol stocks of the ordered libraries, (gDNA and cDNA library respectively) and cultivated in 96-well microtiter plates. The sequences of the inserts from both the 3' and the 5' end were determined by High Throuput (HT) sequencing service.

All RNA samples were labelled with Cy5. Hybridisations were performed with all 30 RNA samples, using Cy3-labeled chromosomal DNA of A. terreus as the reference.

The raw transcriptomics data were shown to be of high quality, based on visual inspection of the arrays after fluorescence scanning. Notably, also the hybridization with the partially degraded RNA samples gave good results.

The normalized data were subsequently combined. As the A. terreus array consisted out of two slides, different strategies of combining the data from the two slides were pursued, making use of the fact that the cDNA clones are present on both the A and B slide:

SET 1=mean expression signal of the cDNA clones on slide A and B, take only those spots that give a signal on both the A and B slide SET 2=use only the signal of the cDNA spots on the A slide. Spots with a Signal/Background below 1.5 were removed.

SET 3=use only the signal of the cDNA spots on the B slide. Spots with a Signal/Background below 1.5 were removed.

SET 4=Combimean cDNA data of both the A and B slide;
i. If both measurement values were zero the combined value was zero;
ii. If both measurements values were both non-zero, the combined value was equal to the average of the two measurement values;
iii. If one of the two measurement values was zero and the other measurement value was non-zero, the combined value was equal to the non-zero measurement value.

SET 5=SET 1+normalized gDNA spots using the normalization factor calculated based on the cDNA clones.

The most relevant spots were subsequently identified by differential expression analysis: the expression ratios between the sample with the lowest itaconate titer and the sample with the highest itaconate titer were calculated (see Table 2). As two samples have a low itaconate titer, the differential expression analysis was performed separately with both these reference samples (i.e. sample 3.a. and 4.a). Similarly, also the expression ratios between the samples with the lowest and the samples with the highest itaconate productivity were calculated.

'Top 20'-ies of the individual data set using the different data analysis approaches were generated. These 'top-20'-ies were combined, and unique spots were identified (Table 4 and 5). In total 88 spots obtained after the differential analyses (based on 15 models; 5 data sets-2 titer and 1 productivity model) were selected for sequencing.

Of the selected spots, >92% were spots belonging to cDNA clones. Of the differential spots, some 50-75% of the spots were present in the 'top 20' of both the itaconate titer and itaconate productivity differentials lists and were mostly upregulated spots, indicating that they might be really relevant for itaconate production.

Following sequence analysis of the 190 selected spots, the genes present on these inserts were identified by performing a homology search using BLAST based on the draft version of the A. terreus genome sequence as available from the BROAD institute (http://www.broad.mit.edu/annotation/fgi/).

Tables 4 and 5 show the results of the genes identified on the 20 highest overall ranking spots identified by differential expression analysis based on titer and productivity, respectively.

Standing out when comparing the highest ranking genes found by differential expression analysis based on productivity versus titer is the cis-aconitate decarboxylase (ATEG_09971.1) which was present on multiple clones in the top 20 rankings, underlining its relevance to the itaconate production phenotype.

TABLE 4

Overall Top 20 Differential expression - itaconic acid titer.

| Rank | Clone ID | Gene locus | Gene name according to (http://www.broad.mit.edu/) |
|---|---|---|---|
| 1 | AsTeR037B09 | ATEG_09971.1 | cis-aconitate decarboxylase |
| 2 | AsTeR017E03 | | |
| 3 | AsTeR008F12 | ATEG_09971.1 | cis-aconitate decarboxylase |
| 4 | AsTeR017E02 | | |
| 5 | AsTeR026D10 | | |
| 6 | AsTeR020B12 | | |
| 7 | AsTeR027F02 | | |
| 8 | AsTeR031E12 | | |
| 9 | AsTeR041A01 | | |
| 10 | AsTeR036C11 | | |
| 11 | AsTeR025E11 | | |
| 12 | AsTeR008H08 | | |
| 13 | AsTeR028C10 | | |
| 14 | AsTeR026G08 | | |
| 15 | AsTeR009E09 | ATEG_09971.1 | cis-aconitate decarboxylase |
| 16 | AsTeR005D11 | ATEG_09971.1 | cis-aconitate decarboxylase |
| 17 | AsTeR056A03 | | |
| 18 | AsTeR010E04 | | |
| 19 | AsTeR045C03 | | |
| 20 | AsTeR054H08 | | |

TABLE 5

Overall Top 20 Differential expression - itaconic acid productivity.

| Rank | Clone ID | Gene locus | Gene name according to (http://www.broad.mit.edu/) |
|---|---|---|---|
| 1 | AsTeR020B12 | | |
| 2 | AsTeR031E12 | | |
| 3 | AsTeR026D10 | | |
| 4 | AsTeR005D11 | ATEG_09971.1 | cis-aconitate decarboxylase |
| 5 | AsTeR017E03 | | |
| 6 | AsTeR008F12 | ATEG_09971.1 | cis-aconitate decarboxylase |
| 7 | AsTeR017E02 | | |
| 8 | AsTeR037B09 | ATEG_09971.1 | cis-aconitate decarboxylase |
| 9 | AsTeR027F02 | | |
| 10 | AsTeR038F06 | | |
| 11 | AsTeR008H08 | | |
| 12 | AsTeR022C05 | ATEG_09971.1 | cis-aconitate decarboxylase |
| 13 | AsTeR037B09 | ATEG_09971.1 | cis-aconitate decarboxylase |
| 14 | AsTeR004A12 | | |
| 15 | AsTeR018E11 | ATEG_09971.1 | cis-aconitate decarboxylase |
| 16 | AsTeR045C03 | | |
| 17 | AsTeR045F08 | | |
| 18 | AsTeR011A05 | | |
| 19 | AsTeR044F02 | | |
| 20 | AsTeR041B02 | | |

Example 6

Expression of CAD Gene in E. Coli

In order to unambiguously establish that the ATEG 9971 protein is indeed responsible for CAD activity, an E. coli-codon-usage-optimized synthetic gene of the ATEG 9971 protein was generated synthetically. It was cloned as a BspHI-BamHI fragment into the E. coli expression vector pET19b (Novagen; Cat. No. 69677-3) cut with NotI-BamHI, resulting in vector pET-9971 (see below for nucleotide sequence of vector pET-9971 (SEQ ID NO:42)).

```
   1 ATGAAACGAG AGAGGATGCT CACGATACGG GTTACTGATG ATGAACATGC CCGGTTACTG
  61 GAACGTTGTG AGGGTAAACA ACTGGCGGTA TGGATGCGGC GGGACCAGAG AAAAATCACT
 121 CAGGGTCAAT GCCAGCGCTT CGTTAATACA GATGTAGGTG TTCCACAGGG TAGCCAGCAG
 181 CATCCTGCGA TGCAGATCCG GAACATAATG GTGCAGGGCG CTGACTTCCG CGTTTCCAGA
 241 CTTTACGAAA CACGGAAACC GAAGACCATT CATGTTGTTG CTCAGGTCGC AGACGTTTTG
 301 CAGCAGCAGT CGCTTCACGT TCGCTCGCGT ATCGGTGATT CATTCTGCTA ACCAGTAAGG
 361 CAACCCCGCC AGCCTAGCCG GGTCCTCAAC GACAGGAGCA CGATCATGCG CACCCGTGGC
 421 CAGGACCCAA CGCTGCCCGA GATGCGCCGC GTGCGGCTGC TGGAGATGGC GGACGCGATG
 481 GATATGTTCT GCCAAGGGTT GGTTTGCGCA TTCACAGTTC TCCGCAAGAA TTGATTGGCT
 541 CCAATTCTTG GAGTGGTGAA TCCGTTAGCG AGGTGCCGCC GGCTTCCATT CAGGTCGAGG
 601 TGGCCCGGCT CCATGCACCG CGACGCAACG CGGGGAGGCA GACAAGGTAT AGGGCGGCGC
 661 CTACAATCCA TGCCAACCCG TTCCATGTGC TCGCCGAGGC GGCATAAATC GCCGTGACGA
 721 TCAGCGGTCC AGTGATCGAA GTTAGGCTGG TAAGAGCCGC GAGCGATCCT TGAAGCTGTC
 781 CCTGATGGTC GTCATCTACC TGCCTGGACA GCATGGCCTG CAACGCGGGC ATCCCGATGC
 841 CGCCGGAAGC GAGAAGAATC ATAATGGGGA AGGCCATCCA GCCTCGCGTC GCGAACGCCA
 901 GCAAGACGTA GCCCAGCGCG TCGGCCGCCA TGCCGGCGAT AATGGCCTGC TTCTCGCCGA
 961 AACGTTTGGT GGCGGGACCA GTGACGAAGG CTTGAGCGAG GGCGTGCAAG ATTCCGAATA
1021 CCGCAAGCGA CAGGCCGATC ATCGTCGCGC TCCAGCGAAA GCGGTCCTCG CCGAAAATGA
1081 CCCAGAGCGC TGCCGGCACC TGTCCTACGA GTTGCATGAT AAAGAAGACA GTCATAAGTG
1141 CGGCGACGAT AGTCATGCCC CGCGCCCACC GGAAGGAGCT GACTGGGTTG AAGGCTCTCA
1201 AGGGCATCGG TCGAGATCCC GGTGCCTAAT GAGTGAGCTA ACTTACATTA ATTGCGTTGC
1261 GCTCACTGCC CGCTTTCCAG TCGGGAAACC TGTCGTGCCA GCTGCATTAA TGAATCGGCC
1321 AACGCGCGGG GAGAGGCGGT TTGCGTATTG GGCGCCAGGG TGGTTTTTCT TTTCACCAGT
1381 GAGACGGGCA ACAGCTGATT GCCCTTCACC GCCTGGCCCT GAGAGAGTTG CAGCAAGCGG
1441 TCCACGCTGG TTTGCCCCAG CAGGCGAAAA TCCTGTTTGA TGGTGGTTAA CGGCGGGATA
1501 TAACATGAGC TGTCTTCGGT ATCGTCGTAT CCCACTACCG AGATATCCGC ACCAACGCGC
1561 AGCCCGGACT CGGTAATGGC GCGCATTGCG CCCAGCGCCA TCTGATCGTT GGCAACCAGC
1621 ATCGCAGTGG GAACGATGCC CTCATTCAGC ATTTGCATGG TTTGTTGAAA ACCGGACATG
1681 GCACTCCAGT CGCCTTCCCG TTCCGCTATC GGCTGAATTT GATTGCGAGT GAGATATTTA
1741 TGCCAGCCAG CCAGACGCAG ACGCGCCGAG ACAGAACTTA ATGGGCCCGC TAACAGCGCG
1801 ATTTGCTGGT GACCCAATGC GACCAGATGC TCCACGCCCA GTCGCGTACC GTCTTCATGG
1861 GAGAAAATAA TACTGTTGAT GGGTGTCTGG TCAGAGACAT CAAGAAATAA CGCCGGAACA
1921 TTAGTGCAGG CAGCTTCCAC GGCAATGGCA TCCTGGTCAT CCAGCGGATA GTTAATGATC
1981 AGCCCACTGA CGCGTTGCGC GAGAAGATTG TGCACCGCCG CTTTACAGGC TTCGACGCCG
2041 CTTCGTTCTA CCATCGACAC CACCACGCTG GCACCCAGTT GATCGGCGCG AGATTTAATC
2101 GCCGCGACAA TTTGCGACGG CGCGTGCAGG GCCAGACTGG AGGTGGCAAC GCCAATCAGC
2161 AACGACTGTT TGCCCGCCAG TTGTTGTGCC ACGCGGTTGG GAATGTAATT CAGCTCCGCC
2221 ATCGCCGCTT CCACTTTTTC CCGCGTTTTC GCAGAAACGT GGCTGGCCTG GTTCACCACG
2281 CGGGAAACGG TCTGATAAGA GACACCGGCA TACTCTGCGA CATCGTATAA GCTTACTGGT
2341 TTCACATTCA CCACCCTGAA TTGACTCTCT TCCGGGCGCT ATCATGCCAT ACCGCGAAAG
2401 GTTTTGCGCC ATTCGATGGT GTCCGGGATC TCGACGCTCT CCCTTATGCG ACTCCTGCAT
2461 TAGGAAGCAG CCCAGTAGTA GGTTGAGGCC GTTGAGCACC GCCGCCGCAA GGAATGGTGC
2521 ATGCAAGGAG ATGGCGCCCA ACAGTCCCCC GGCCACGGGG CCTGCCACCA TACCCACGCC
2581 GAAACAAGCG CTCATGAGCC CGAAGTGGCG AGCCCGATCT TCCCCATCGG TGATGTCGGC
2641 GATATAGGCG CCAGCAACCG CACCTGTGGC GCCGGTGATG CCGGCCACGA TGCGTCCGGC
2701 GTAGAGGATC GAGATCTCGA TCCCGCGAAA TTAATACGAC TCACTATAGG GGAATTGTGA
2761 GCGGATAACA ATTCCCCTCT AGAAATAATT TTGTTTAACT TTAAGAAGGA GATATACCAT
2821 GACCAAACAA AGTGCTGATT CTAACGCCAA GAGTGGCGTG ACCGCAGAAA TTTGCCATTG
2881 GGCGTCGAAT CTGGCGACGG ACGATATCCC GTCCGACGTC CTGGAACGCG CCAAGTATCT
2941 GATTCTGGAC GGTATTGCAT GTGCTTGGGT CGGGGCGCCC GTACCGTGGT CGGAAAAATA
3001 CGTGCAAGCC ACTATGAGCT TTGAACCGCC GGGCGCATGC CGTGTTATTG GTTACGGTCA
3061 AAAGCTGGGG CCGGTCGCGG CGGCCATGAC AAATAGCGCT TTTATCCAAG CCACAGAACT
3121 GGACGATTAT CACAGTGAGG CGCCGCTGCA CTCAGCGTCC ATTGTACTGC CGGCAGTATT
3181 CGCCAGCTTC A GAGGTTCTGG CCGAACAGGG TAAAACGATC AGCGGCATTG ACGTTATCCT
3241 GGCTGCGATT GTGGGTTTCG AGTCTGGGCC GCGTATTGGC AAGGCAATTT ACGGTAGTGA
3301 TCTGCTGAAC AACGGCTGGC ATTGTGGTGC AGTATACGGG GCACCGGCGG GGGCGCTCCC
3361 TACTGGTAAA CTGCTGGGGC TGACACCGGA CTCGATGGAG GACGCACTGG GCATCGCGTG
3421 TACCCAAGCG TGCGGTCTGA TGTCCGCACA ATACGGCGGT ATGGTGAAGC GTGTCCAACA
3481 CGGTTTTGCT GCCCGTAACG GTCTGCTGGG TGGCCTGCTG GCTTACGGTG GGTACGAAGC
3541 GATGAAAGGC GTGCTGGAAC GCAGTTACGG TGGGTTCCTG AAGATGTTTA CGAAAGGCAA
3601 CCGGTCGCGA A CCGCCGTACA AAGAGGAAGA AGTTGTTGCC GGTCTGGGCT CCTTTTGGCA
3661 CACTTTTACT ATTCGTATCA AGCTGTACGC ATGCTGTGGG CTGGTGCACG GTCCGGTGGA
3721 AGCAATTGAA AAGCTGCAGC GTCGCTACCC GGAGCTGCTG AACGCGCGCA ATCGTCTAA
3781 CATTCGTCAC GTGTACGTTC AGCTGTCGAC TGCGAGCAAC GTCACTGCG GTTGGATACC
3841 GGAAGAACGC CCGATTAGCT CGATCGCCGG TCAGATGTCT GTAGCCTATA TTCTCGGCGT
3901 CCAACTGGTT GATCAGCAAT GCCTGCTGGC ACAATTTTCT GAGTTTGACG ATAACCTGGA
3961 ACGTCCGGAA GTGTGGGATC TGGCCCGTAA AGTCACACCG AGTCACAGCG AGGAGTTCGA
4021 CCAGGATGGC AATTGCCTGA GTGCTGGTCG TGTTCGTATC GAGTTCAACG ACGGCTCGTC
```

-continued

```
4081 GGTCACCGAG ACTGTCGAAA AGCCGCTGGG TGTGAAAGAA CCGATGCCGA ATGAACGTAT
4141 TCTGCACAAG TATCGCACAC TGGCGGGGAG CGTTACTGAC GAGAGCCGTG TAAAGGAAAT
4201 CGAAGATCTG GTCCTGTCAC TGGACCGCCT GACGGATATT ACCCCGCTGC TGGAGCTGCT
4261 GAACTGTCCG GTTAAATCCC CGCTGGTGTA AGGATCCGGC TGCTAACAAA GCCCGAAAGG
4321 AAGCTGAGTT GGCTGCTGCC ACCGCTGAGC AATAACTAGC ATAACCCCTT GGGGCCTCTA
4381 AACGGGTCTT GAGGGGTTTT TTGCTGAAAG GAGGAACTAT ATCCGGATAT CCCGCAAGAG
4441 GCCCGGCAGT ACCGGCATAA CCAAGCCTAT GCCTACAGCA TCCAGGGTGA CGGTGCCGAG
4501 GATGACGATG AGCGCATTGT TAGATTTCAT ACACGGTGCC TGACTGCGTT AGCAATTTAA
4561 CTGTGATAAA CTACCGCATT AAAGCTTATC GATGATAAGC TGTCAAACAT GAGAATTCTT
4621 GAAGACGAAA GGGCCTCGTG ATACGCCTAT TTTTATAGGT TAATGTCATG ATAATAATGG
4681 TTTCTTAGAC GTCAGGTGGC ACTTTTCGGG GAAATGTGCG CGGAACCCCT ATTTGTTTAT
4741 TTTTCTAAAT ACATTCAAAT ATGTATCCGC TCATGAGACA ATAACCCTGA TAAATGCTTC
4801 AATAATATTG AAAAAGGAAG AGTATGAGTA TTCAACATTT CCGTGTCGCC CTTATTCCCT
4861 TTTTTGCGGC ATTTTGCCTT CCTGTTTTTG CTCACCCAGA AACGCTGGTG AAAGTAAAAG
4921 ATGCTGAAGA TCAGTTGGGT GCACGAGTGG GTTACATCGA ACTGGATCTC AACAGCGGTA
4981 AGATCCTTGA GAGTTTTCGC CCCGAAGAAC GTTTTCCAAT GATGAGCACT TTTAAAGTTC
5041 TGCTATGTGG CGCGGTATTA TCCCGTGTTG ACGCCGGGCA AGAGCAACTC GGTCGCCGCA
5101 TACACTATTC TCAGAATGAC TTGGTTGAGT ACTCACCAGT CACAGAAAAG CATCTTACGG
5161 ATGGCATGAC AGTAAGAGAA TTATGCAGTG CTGCCATAAC CATGAGTGAT AACACTGCGG
5221 CCAACTTACT TCTGACAACG ATCGGAGGAC CGAAGGAGCT AACCGCTTTT TTGCACAACA
5281 TGGGGGATCA TGTAACTCGC CTTGATCGTT GGGAACCGGA GCTGAATGAA GCCATACCAA
```

```
5341 ACGACGAGCG TGACACCACG ATGCCTGCAG CAATGGCAAC AACGTTGCGC AAACTATTAA
5401 CTGGCGAACT ACTTACTCTA GCTTCCCGGC AACAATTAAT AGACTGGATG GAGGCGGATA
5461 AAGTTGCAGG ACCACTTCTG CGCTCGGCCC TTCCGGCTGG CTGGTTTATT GCTGATAAAT
5521 CTGGAGCCGG TGAGCGTGGG TCTCGCGGTA TCATTGCAGC ACTGGGGCCA GATGGTAAGC
5581 CCTCCCGTAT CGTAGTTATC TACACGACGG GGAGTCAGGC AACTATGGAT GAACGAAATA
5641 GACAGATCGC TGAGATAGGT GCCTCACTGA TTAAGCATTG GTAACTGTCA GACCAAGTTT
5701 ACTCATATAT ACTTTAGATT GATTTAAAAC TTCATTTTTA ATTTAAAAGG ATCTAGGTGA
5761 AGATCCTTTT TGATAATCTC ATGACCAAAA TCCCTTAACG TGAGTTTTCG TTCCACTGAG
5821 CGTCAGACCC CGTAGAAAAG ATCAAAGGAT CTTCTTGAGA TCCTTTTTTT CTGCGCGTAA
5881 TCTGCTGCTT GCAAACAAAA AAACCACCGC TACCAGCGGT GGTTTGTTTG CCGGATCAAG
5941 AGCTACCAAC TCTTTTTCCG AAGGTAACTG GCTTCAGCAG AGCGCAGATA CCAAATACTG
6001 TCCTTCTAGT GTAGCCGTAG TTAGGCCACC ACTTCAAGAA CTCTGTAGCA CCGCCTACAT
6061 ACCTCGCTCT GCTAATCCTG TTACCAGTGG CTGGTGCCAG TGGCGATAAG TCGTGTCTTA
6121 CCGGGTTGGA CTCAAGACGA TAGTTACCGG ATAAGGCGCA GCGGTCGGGC TGAACGGGGG
6181 GTTCGTGCAC ACAGCCCAGC TTGGAGCGAA CGACCTACAC CGAACTGAGA TACCTACAGC
6241 GTGAGCTATG AGAAAGCGCC ACGCTTCCCG AAGGGAGAAA GGCGGACAGG TATCCGGTAA
6301 GCGGCAGGGT CGGAACAGGA GAGCGCACGA GGGAGCTTCC AGGGGGAAAC GCCTGGTATC
6361 TTTATAGTCC TGTCGGGTTT CGCCACCTCT GACTTGAGCG TCGATTTTTG TGATGCTCGT
6421 CAGGGGGGCG GAGCCTATGG AAAAACGCCA GCAACGCGGC CTTTTTACGG TTCCTGGCCT
6481 TTTGCTGGCC TTTTGCTCAC ATGTTCTTTC CTGCGTTATC CCCTGATTCT GTGGATAACC
6541 GTATTACCGC CTTTGAGTGA GCTGATACCG CTCGCCGCAG CCGAACGACC GAGCGCAGCG
```

```
6601 AGTCAGTGAG CGAGGAAGCG GAAGAGCGCC TGATGCGGTA TTTTCTCCTT ACGCATCTGT
6661 GCGGTATTTC ACACCGCATA TATGGTGCAC TCTCAGTACA ATCTGCTCTG ATGCCGCATA
6721 GTTAAGCCAG TATACACTCC GCTATCGCTA CGTGACTGGG TCATGGCTGC GCCCCGACAC
6781 CCGCCAACAC CCGCTGACGC GCCCTGACGG GCTTGTCTGC TCCCGGCATC CGCTTACAGA
6841 CAAGCTGTGA CCGTCTCCGG GAGCTGCATG TGTCAGAGGT TTTCACCGTC ATCACCGAAA
6901 CGCGCGAGGC AGCTGCGGTA AAGCTCATCA GCGTGGTCGT GAAGCGATTC ACAGATGTCT
6961 GCCTGTTCAT CCGCGTCCAG CTCGTTGAGT TTCTCCAGAA GCGTTAATGT CTGGCTTCTG
7021 ATAAAGCGGG CCATGTTAAG GGCGGTTTTT TCCTGTTTGG TCACTGATGC CTCCGTGTAA
7081 GGGGGATTTC TGTTCATGGG GGTAATGATA CCG
```

ATG startcodon in bold, italics
TAA stop codon in bold, underlined
CAD gene ATEG 9971

Subsequently E. coli strain BL21 (DE3) was transformed with vector pET-9971 and pET52 (expression vector without an insert) and transformants were cultivated in LB medium and on mineral salts medium (Hellmuth, 1994, J. Biotechnol. 32:289) supplemented with 0.5% glucose, 5 mM $MgCl_2$ and 100 μl/ml ampicillin. Freshly inoculated cultures were grown at 37° C., 250 rpm to an OD600 of 0.5-0.8, incubated on ice for 30 min, after which IPTG was added to a final concentration of 0.2 M. The cultures were subsequently cultivated overnight at 20° C., 250 rpm. Cells were harvested by centrifugation and the medium supernatant was analyzed by HPLC (see example 2).

Moreover, cell extracts were prepared by sonication (2×2 min sonication, setting at 3, output 30-40%-Branson Sonifier 450) in 0.2 M sodium phosphate (pH 6.5), 1 mM Na-EDTA, 1 mM DTT, 1 mM PMSF and 1.0 μg/ml pepstatin A. A cell free extract was obtained by centrifuging the crude extract for 15 min., 10.000 g 4° C. The CAD activity of these cell extracts was determined (Table 6).

IPTG-induced cells contained a distinct band with a molecular weight similar to the CAD protein (FIG. 5). The spent medium of the E. coli expressing the ATEG 9971 showed that these cultures produced up to 0.08 g/l of itaconate (Table 6). Moreover, when cell extracts of these cells were incubated with cis-aconitate itaconate was formed. This was not the case in *E. coli* containing the original expression vector, or in cells not induced by IPTG (Table 6). This demonstrates that the ATEG 9971 gene indeed codes for cis-aconitate decarboxylase activity.

TABLE 6

Production of itaconate by cell extracts of an *E. coli* transformant containing the ATEG 9971 gene in expression vector pET52 cultivated on different media

| Strain | Medium | Itaconate in culture medium (mg/l) | Itaconate produced from cis-aconitate by cell free extracts (mg/30 minutes per mg protein) |
|---|---|---|---|
| *E. coli* - pET52 (empty vector) | Luria Broth + IPTG | 0 | 0 |
| *E. coli* - pET52 (empty vector) | Mineral salts medium + IPTG | 0 | 0 |

TABLE 6-continued

Production of itaconate by cell extracts of an *E. coli* transformant containing the ATEG 9971 gene in expression vector pET52 cultivated on different media

| Strain | Medium | Itaconate in culture medium (mg/l) | Itaconate produced from cis-aconitate by cell free extracts (mg/30 minutes per mg protein) |
|---|---|---|---|
| *E. coli* - pET-9971 | Luria Broth | 0 | 0.2 |
| *E. coli* - pET-9971 | Luria Broth + IPTG | 83 | 18.5 |
| *E. coli* - pET-9971 | Mineral salts medium | 0 | 0.0 |
| *E. coli* - pET-9971 | Mineral salts medium + IPTG | 56 | 9.3 |

Example 7

Expression of ATEG_09971.1 in *Aspergillus niger*

To establish that introduction of the ATEG 9971 protein is also capable of rendering an naturally non-itaconic acid producing fungal host into a producing organism as PCR generated copy of the gene encoding the ATEG 9971 protein was generated. For this purpose two sets of primers were generated as shown below. PCCR amplification based on *A. terreus* genomic DNA (SEQ ID NO:23) resulted in the isolation of PCR fragments from which the complete coding region of the gene encoding the ATEG 9971 protein, could be isolated as BspHI-BamHI fragments

```
Translation of ATEG 7791 encoding gene(1-1473) (SEQ ID NO: 24)
Universal code
Total amino acid number: 490, MW=52872
Max ORF starts at AA pos 1(may be DNA pos 1) for 490 AA(1470 bases), MW=52872

BspHI   cadfor40° C.
5'-ATCGTCATGACCAAGCAATCTG- 3' (SEQ ID NO: 25)

BspHI   cadfor53° C.
5'-ATCGTCATGACCAAGCAATCTGCGGACA- 3' (SEQ ID NO: 26)

1 ATGACCAAGCAATCTGCGGACAGCAACGCAAAGTCAGGAGTTACGGCCGAAATATGCCAT
  1 M  T  K  Q  S  A  D  S  N  A  K  S  G  V  T  A  E  I  C  H

61 TGGGCATCCAACCTGGCCACTGACGACATCCCTTCGGACGTATTAGAAAGAGCGAAATAC
 21 W  A  S  N  L  A  T  D  D  I  P  S  D  V  L  E  R  A  K  Y

121 CTGATTCTCGATGGTATTGCATGTGCCTGGGTTGGTGCAAGAGTGCCTTGGTCAGAGAAG
 41 L  I  L  D  G  I  A  C  A  W  V  G  A  R  V  P  W  S  E  K

181 TATGTGCAGGCAACAATGAGCTTTGAGCCGCCAGGAGCCTGCAGGGTGATTGGATATGGG
 61 Y  V  Q  A  T  M  S  F  E  P  P  G  A  C  R  V  I  G  Y  G

241 CAGAAACTGGGGCCTGTTGCAGCAGCCATGACCAATTCCGCTTTCATACAGGCCACAGAG
 81 Q  K  L  G  P  V  A  A  A  M  T  N  S  A  F  I  Q  A  T  E
```

-continued

```
301 CTTGACGACTACCACAGCGAAGCCCCCTACACTCTGCAAGCATCGTCCTCCCTGCGGTC
101  L  D  D  Y  H  S  CAD(375)for  H  S  A  S  I  V  L  P  A  V
361 TTTGCAGCAAGTGAGGTCTTAGCCGAGCAAGGCAAAACAATTTCTGGTATAGATGTCATT
121  F  A  A  S  E  V  L  A  E  Q  G  K  T  I  S  G  I  D  V  I 421 CTAGCCGCCATTGTGGGGTTTGAATCTGGCCCGCGGATCGGCAAAGCAATTTACGGATCG
141  L  A  A  I  V  G  F  E  S  G  P  R  I  G  K  A  I  Y  G  S 481 GACCTCTTGAACAACGGCTGGCATTGTGGAGCCGTGTATGGTGCTCCAGCTGGTGCGCTG
161  D  L  L  N  N  G  W  H  C  G  A  V  Y  G  A  P  A  G  A  L 541 GCCACAGGAAAGCTCCTCGGTCTAACTCCAGACTCCATGGAAGATGCTCTCGGAATCGCG
181  A  T  G  K  L  L  G  L  T  P  D  S  M  E  D  A  L  G  I  A 601 TGCACGCAAGCCTGTGGTTTAATGTCGGCGCAATACGGAGGCATGGTCAAGCGCGTGCAA
201  C  T  Q  A  C  G  L  M  S  A  Q  Y  G  G  M  V  K  R  V  Q 661 CATGGATTCGCAGCGCGTAATGGTCTTCTTGGGGACTGTTGGCCTATGGTGGGTACGAG
221  H  G  F  A  A  R  N  G  L  L  G  G  L  L  A  Y  G  G  Y  E 721 GCCATGAAGGGTGTCCTGGAGAGATCTTATGGCGGTTTCCTCAAAATGTTCACCAAGGGC
241  A  M  K  G  V  L  E  R  S  Y  G  G  F  L  K  M  F  T  K  G 781 AATGGCAGAGAGCCTCCCTACAAAGAGGAGGAAGTGGTGGCCGGTCTCGGTTCATTCTGG
261  N  G  R  E  P  P  Y  K  E  E  E  V  V  A  G  L  G  S  F  W 901 CATGCTTTCGCTAATCGTCACAAGGCGTATGCCTGGTGCGGACATGTCAGTGGTCCAGTC
301  H  A  F  E  K  Q  N  L  Y  A  G  C  G  N  V  N  G  E  V 961 AACATTCGCCATGTTTATGTACAGCTTTCAACAGCCTCGAACAGTCACTGTGGATGGATA
321  N  I  R  H  V  Y  V  Q  L  S  T  A  S  N  S  H  C  G  W  I CAD(1067)rev
             3'- GTCCCGTCTACTCACACGC - 5' (SEQ ID NO: 27)
1021 CCAGAGGAGAGGCCCATCAGTTCAATCGCAGGGCAGATGAGTGTCGCATACATCCTCGCC
 341  P  E  E  R  P  I  S  S  I  A  G  Q  M  S  V  A  Y  I  L  A 1081 GTCCAGCTGGTCGACCAGCAATGTCTTCTGGCTCAGTTTTCTGAGTTTGATGACAACTTG
 361  V  Q  L  V  D  Q  Q  C  L  L  A  Q  F  S  E  F  D  D  N  L 1141 GAGAGACCAGAAGTGTGGGATCTGGCCAGGAAGGTTACTCCATCTCATAGCGAAGAGTTT
 381  E  R  P  E  V  W  D  L  A  R  K  V  T  P  S  H  S  E  E  F 1201 GATCAAGACGGCAACTGTCTCAGTGCGGGTCGCGTGAGGATTGAGTTCAACGATGGCTCT
 401  D  Q  D  G  N  C  L  S  A  G  R  V  R  I  E  F  N  D  G  S 1261 TCTGTTACGGAAACTGTCGAGAAGCCTCTTGGAGTCAAAGAGCCCATGCCAAACGAACGG
 421  S  V  T  E  T  V  E  K  P  L  G  V  K  E  P  M  P  N  E  R 1321 ATTCTCCACAAATACCGAACCCTTGCGGGTAGCGTGACGGACGAATCCCGGGTGAAAGAG
 441  I  L  H  K  Y  R  T  L  A  G  S  V  T  D  E  S  R  V  K  E 1381 ATTGAGGATCTTGTCCTCAGCCGTGGACAGGCTCAGCGACATTACCCCATTGCTGGAGCTG
 461  I  E  D  L  V  cadrev52°C.   G  BamHI
                 3'-TTTASCGGTGACCATATTCCTAGGCCT-5' (SEQ ID NO: 28)

cadrev52° C.        BamHI
             3'-GGCATTTTAGCGGTGACCATATTCCTAGGCCCC- 5' (SEQ ID NO: 29)
1441 CTTAATTGTCCCGTGAAATCGCCACTGGTATAA
 481  L  N  C  P  V  K  S  P  L  V  *
```

Overview Cad Primers:

```
cadfor40° C.; 22-mer
5'-ATCGTCATGACCAAGCAATCTG-3'Primer (SEQ ID NO: 30)
   ||||||||||||||||||||||
3'-      TACTGGTTCGTTAGAC-5'(16)Strand- (SEQ ID NO: 31)

cadfor53° C.; 28-mer
5'-ATCGTCATGACCAAGCAATCTGCGGACA-3'Primer (SEQ ID NO: 32)
   ||||||||||||||||||||||||||||
3'-      TACTGGTTCGTTAGACGCCTGT-5'(22)Strand- (SEQ ID NO: 33)
```

```
cadrev42° C.; 28-mer
5'-TCCCGGATCCTTATACCAGTGGCGATTT-3'Primer (SEQ ID NO: 34)
          ||||||||||||||||||||
3'-         AATATGGTCACCGCTAAA-5'(1456)Strand+ (SEQ ID NO: 35)

cadrev52° C.; 33-mer
5'-CCCCGGATCCTTATACCAGTGGCGATTTTACGG-3'Primer (SEQ ID NO: 36)
          |||||||||||||||||||||||
3'-         AATATGGTCACCGCTAAAGTGCC-5'(1451)Strand+ (SEQ ID NO: 37)

CAD(375)for; 19-mer
5'-GGTCTTAGCCGAGCAAGGC-3'Primer (SEQ ID NO: 38)
   |||||||||||||||||||
3'-CCAGAATCGGCTCGTTCCG-5'(393)Strand- (SEQ ID NO: 39)

CAD(1067)rev; 19-mer
5'-GCGACACTCATCTGCCCTG-3'Primer (SEQ ID NO: 40)
   |||||||||||||||||||
3'-CGCTGTGAGTAGACGGGAC-5'(1049)Strand+ (SEQ ID NO: 41)
```

The resulting BspHI—BamHI fragment was cloned into the *Aspergillus* expression vector pAN52-4 (EMBL accession #Z32699) digested with NcoI—BamHI. In a derivative of this vector also the *Aspergillus* selection marker amdS was cloned.

Subsequently, an *Aspergillus niger* strain derived from AB4.1 (van Hartingveldt, W. et al., 1987, Mol. Gen. Genet. 206:71-75) was transformed with the ATEG 7791 expression vector. AmdS transformants resulting for this experiment were purified by single colony purification and retested for their AmdS+ phenotype. In addition colony PCR was carried out on a selection of the AmdS+ transformants using the primers which were used to generate the PCR gene copy, to verify the presence of an intact ATEG 9971 gene copy in these transformants. Several PCR positive transformants and the parental host strain were subsequently cultured in Batch Fermentation in MM medium containing glucose as C-source and Nitrate as N-source (see example 4). Medium samples from the various cultures were analyzed by HPLC (see example 4) for the presence of itaconic acid. In the medium from the strains containing the ATEG 9971 gene itaconic acid was detected.

Example 8

A. terreus Genome Organization

It appears that at least the gene coding for the cis-aconitate decarboxylase (ATEG_09971.1) and the gene encoding the putitative mitochondrial tricarboxylate transporter (ATEG_9970.1) lie in the same cluster in the *A. terreus* genome (FIG. 6).

Flanking the CAD and the putative mitochondrial tricarboxylate transporter genes is the Major Facilitator Superfamily (MFS) transporter (ATEG_09972.1) that was identified by Partial Least Squares (PLS) biostatistical analysis. MFS transporters are a diverse family of transport proteins, transporting compounds ranging from sugars to organic acids, including dicarboxylic acids. In *A. niger* some 450 different MFS genes are present. The localization of MFS ATEG_09972.1 and its identification by PLS, suggest that this is the itaconate exporter.

A gene neighbouring CAD, the putative mitochondrial tricarboxylate transporter and the putative itaconate exporter is a putative regulator containing a zinc-finger domain (ATEG_09969.1). This gene was not identified using our transcriptomics approach, but considering its localization it is supposed that it is relevant for itaconic acid synthesis FIG. 6 shows that also the lovastatin pathway genes are located on this cluster, suggesting a link between both pathways which are (mainly) specific for *A. terreus*.

The invention claimed is:

1. A method for the production of itaconic acid comprising providing to a suitable host cell a recombinant expression system for a nucleic acid molecule encoding the enzyme cis-aconitic acid decarboxylase (CAD) wherein said host cell does not naturally produce itaconic acid or produces itaconic acid only minimally.

2. A method of claim 1, wherein the nucleic acid molecule encodes a CAD protein comprising an amino acid sequence which has an identity of at least 95% with the amino acid sequence of FIG. 2B (SEQ ID NO:2) and which protein exhibits cis-aconitic acid decarboxylase activity.

3. The method of claim 1, wherein said suitable host cell is a citrate producing micro-organism.

4. The method of claim 1, wherein said host is also provided with a nucleic acid molecule encoding a protein that transports di/tricarboxylic acids from the mitochondrion.

5. The method of claim 1, wherein the expression of the zinc-finger regulator protein encoded by the nucleic acid present in ATEG_09969.1 (SEQ ID NOS:17-18) is modulated in said host.

6. The method of claim 1, wherein said host is also provided with a nucleic acid molecule encoding an itaconate transporting Major Facilitator Superfamily Transporter (MFST).

7. The method of claim 3 wherein the microorganism is *Aspergillus niger, Aspergillus itaconicus, Yarrowia lipolytica, Ustilago zeae, Candida* sp., *Rhodotorula* sp., *Pseudozyma Antarctica, E. coli* or *Saccharomyces cerevisiae.*

8. The method of claim 1 wherein the microorganism is *Monascus* spp., *Penicillium* spp., *Hypomyces* spp., *Doratomyces* spp., *Phoma* spp., *Eupenicillium* spp., *Gymnoascus* spp., *Pichia labacensis, Candida cariosilognicola, Paecilomyces varioti, Scopulariopsis brevicaulis* or *Trichoderma* spp.

* * * * *

UNITED STATES PATENT AND TRADEMARK OFFICE
CERTIFICATE OF CORRECTION

PATENT NO.       : 8,440,436 B2                                      Page 1 of 1
APPLICATION NO.  : 12/669955
DATED            : May 14, 2013
INVENTOR(S)      : Van Der Werf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 316 days.

Signed and Sealed this

Eighth Day of September, 2015

Michelle K. Lee
*Director of the United States Patent and Trademark Office*

SEQUENCE LISTING

```
<160> NUMBER OF SEQ ID NOS: 42

<210> SEQ ID NO 1
<211> LENGTH: 2029
<212> TYPE: DNA
<213> ORGANISM: Aspergillus terreus
<220> FEATURE:
<221> NAME/KEY: CDS
<222> LOCATION: (501)...(743)
<220> FEATURE:
<221> NAME/KEY: CDS
<222> LOCATION: (800)...(2026)

<400> SEQUENCE: 1
gtccctggtg ggtcttgaaa tcgcatgtca cactcattcc ggatgaaaca cattccggag        60
cacgcgttga tattgctaaa cagtatagac ccgaatggtc tgcagaagcc ctaaatagta       120
ggtctcatta gccagcattt agttgtgatt gcagatcatt gtcagcctaa catcagtgta       180
ggttacggtg tgatatttac ttgcatagaa ggttccagac cacacggttc tagatccttt       240
```

```
gacagcagca tgaatggatt gccctctagg tgccgggcgc cgacgtgtgt gttgctccgg      300
gatttgtagg acggagctcg gataccctagc cgctatgggc atcggaggtt gtagcagcgt    360
acacacttgg atagttaaat aatcgggtgt acacccactg ttggaaatga cggggggccta   420 aaaacacgag attatctgac ccaatttctg ttcgttggca ttctatcatt cgcagcgaag    480
atcgtcctct taaattgacc atg acc aag caa tct gcg gac agc aac gca aag    533
                      Met Thr Lys Gln Ser Ala Asp Ser Asn Ala Lys
                       1               5                  10 tca gga gtt acg gcc gaa ata tgc cat tgg gca tcc aac ctg gcc act      581
Ser Gly Val Thr Ala Glu Ile Cys His Trp Ala Ser Asn Leu Ala Thr
            15                  20                  25 gac gac atc cct tcg gac gta tta gaa aga gcg aaa tac ctg att ctc      629
Asp Asp Ile Pro Ser Asp Val Leu Glu Arg Ala Lys Tyr Leu Ile Leu
        30                  35                  40 gat ggt att gca tgt gcc tgg gtt ggt gca aga gtg cct tgg tca gag      677
Asp Gly Ile Ala Cys Ala Trp Val Gly Ala Arg Val Pro Trp Ser Glu
    45                  50                  55 aag tat gtg cag gca aca atg agc ttt gag ccg cca gga gcc tgc agg      725
Lys Tyr Val Gln Ala Thr Met Ser Phe Glu Pro Pro Gly Ala Cys Arg
60                  65                  70                  75 gtg att gga tat ggg cag gtaagcttta tccaatctag acagtctaca             773
Val Ile Gly Tyr Gly Gln
                80 aagtatactg acgattcttt gtatag aaa ctg ggg cct gtt gca gca gcc atg     826
                           Lys Leu Gly Pro Val Ala Ala Ala Met
                                           85                  90 acc aat tcc gct ttc ata cag gcc aca gag ctt gac gac tac cac agc      874
Thr Asn Ser Ala Phe Ile Gln Ala Thr Glu Leu Asp Asp Tyr His Ser
                95                  100                 105 gaa gcc ccc cta cac tct gca agc atc gtc ctc cct gcg gtc ttt gca      922
Glu Ala Pro Leu His Ser Ala Ser Ile Val Leu Pro Ala Val Phe Ala
        110                 115                 120 gca agt gag gtc tta gcc gag caa ggc aaa aca att tct ggt ata gat      970
Ala Ser Glu Val Leu Ala Glu Gln Gly Lys Thr Ile Ser Gly Ile Asp
    125                 130                 135 gtc att cta gcc gcc att gtg ggg ttt gaa tct ggc ccg cgg atc ggc      1018
Val Ile Leu Ala Ala Ile Val Gly Phe Glu Ser Gly Pro Arg Ile Gly
140                 145                 150 aaa gca att tac gga tcg gac ctc ttg aac aac ggc tgg cat tgt gga     1066
Lys Ala Ile Tyr Gly Ser Asp Leu Leu Asn Asn Gly Trp His Cys Gly
155                 160                 165                 170 gcc gtg tat ggt gct cca gct ggt gcg ctg gcc aca gga aag ctc ctc     1114
Ala Val Tyr Gly Ala Pro Ala Gly Ala Leu Ala Thr Gly Lys Leu Leu
                175                 180                 185 ggt cta act cca gac tcc atg gaa gat gct ctc gga atc gcg tgc acg     1162
Gly Leu Thr Pro Asp Ser Met Glu Asp Ala Leu Gly Ile Ala Cys Thr
        190                 195                 200 caa gcc tgt ggt tta atg tcg gcg caa tac gga ggc atg gtc aag cgc     1210
Gln Ala Cys Gly Leu Met Ser Ala Gln Tyr Gly Gly Met Val Lys Arg
    205                 210                 215 gtg caa cat gga ttc gca gcg cgt aat ggt ctt ctt ggg gga ctg ttg     1258
Val Gln His Gly Phe Ala Ala Arg Asn Gly Leu Leu Gly Gly Leu Leu
220                 225                 230 gcc tat ggt ggg tac gag gcc atg aag ggt gtc ctg gag aga tct tat     1306
Ala Tyr Gly Gly Tyr Glu Ala Met Lys Gly Val Leu Glu Arg Ser Tyr
235                 240                 245                 250 ggc ggt ttc ctc aaa atg ttc acc aag ggc aat ggc aga gag cct ccc     1354
Gly Gly Phe Leu Lys Met Phe Thr Lys Gly Asn Gly Arg Glu Pro Pro
                255                 260                 265
```

```
tac aaa gag gag gaa gtg gtg gcc ggt ctc ggt tca ttc tgg cat acc    1402
Tyr Lys Glu Glu Glu Val Val Ala Gly Leu Gly Ser Phe Trp His Thr
            270                 275                 280 ttt act att cgc atc aag ctc tat gcc tgc tgc gga ctt gtc cat ggt    1450
Phe Thr Ile Arg Ile Lys Leu Tyr Ala Cys Cys Gly Leu Val His Gly
        285                 290                 295 cca gtc gaa gct atc gaa aag ctt cag agg aga tac ccc gag ctc ttg    1498
Pro Val Glu Ala Ile Glu Lys Leu Gln Arg Arg Tyr Pro Glu Leu Leu
    300                 305                 310 aat aga gcc aac ctc agc aac att cgc cat gtt tat gta cag ctt tca    1546
Asn Arg Ala Asn Leu Ser Asn Ile Arg His Val Tyr Val Gln Leu Ser
315                 320                 325                 330 aca gcc tcg aac agt cac tgt gga tgg ata cca gag gag agg ccc atc    1594
Thr Ala Ser Asn Ser His Cys Gly Trp Ile Pro Glu Glu Arg Pro Ile
                335                 340                 345 agt tca atc gca ggg cag atg agt gtc gca tac atc ctc gcc gtc cag    1642
Ser Ser Ile Ala Gly Gln Met Ser Val Ala Tyr Ile Leu Ala Val Gln
            350                 355                 360 ctg gtc gac cag caa tgt ctt ctg gct cag ttt tct gag ttt gat gac    1690
Leu Val Asp Gln Gln Cys Leu Leu Ala Gln Phe Ser Glu Phe Asp Asp
        365                 370                 375 aac ttg gag aga cca gaa gtg tgg gat ctg gcc agg aag gtt act cca    1738
Asn Leu Glu Arg Pro Glu Val Trp Asp Leu Ala Arg Lys Val Thr Pro
    380                 385                 390 tct cat agc gaa gag ttt gat caa gac ggc aac tgt ctc agt gcg ggt    1786
Ser His Ser Glu Glu Phe Asp Gln Asp Gly Asn Cys Leu Ser Ala Gly
395                 400                 405                 410 cgc gtg agg att gag ttc aac gat ggc tct tct gtt acg gaa act gtc    1834
Arg Val Arg Ile Glu Phe Asn Asp Gly Ser Ser Val Thr Glu Thr Val
                415                 420                 425 gag aag cct ctt gga gtc aaa gag ccc atg cca aac gaa cgg att ctc    1882
Glu Lys Pro Leu Gly Val Lys Glu Pro Met Pro Asn Glu Arg Ile Leu
            430                 435                 440 cac aaa tac cga acc ctt gcg ggt agc gtg acg gac gaa tcc cgg gtg    1930
His Lys Tyr Arg Thr Leu Ala Gly Ser Val Thr Asp Glu Ser Arg Val
        445                 450                 455 aaa gag att gag gat ctt gtc ctc agc ctg gac agg ctc acc gac att    1978
Lys Glu Ile Glu Asp Leu Val Leu Ser Leu Asp Arg Leu Thr Asp Ile
    460                 465                 470 acc cca ttg ctg gag ctg ctt aat tgt ccc gtg aaa tcg cca ctg gta    2026
Thr Pro Leu Leu Glu Leu Leu Asn Cys Pro Val Lys Ser Pro Leu Val
475                 480                 485                 490 taa                                                                2029

<210> SEQ ID NO 2
<211> LENGTH: 490
<212> TYPE: PRT
<213> ORGANISM: Aspergillus terreus

<400> SEQUENCE: 2

Met Thr Lys Gln Ser Ala Asp Ser Asn Ala Lys Ser Gly Val Thr Ala
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80
```

```
Gln Lys Leu Gly Pro Val Ala Ala Ala Met Thr Asn Ser Ala Phe Ile
                 85                  90                  95
Gln Ala Thr Glu Leu Asp Asp Tyr His Ser Glu Ala Pro Leu His Ser
            100                 105                 110
Ala Ser Ile Val Leu Pro Ala Val Phe Ala Ala Ser Glu Val Leu Ala
        115                 120                 125
Glu Gln Gly Lys Thr Ile Ser Gly Ile Asp Val Ile Leu Ala Ala Ile
    130                 135                 140
Val Gly Phe Glu Ser Gly Pro Arg Ile Gly Lys Ala Ile Tyr Gly Ser
145                 150                 155                 160
Asp Leu Leu Asn Asn Gly Trp His Cys Gly Ala Val Tyr Gly Ala Pro
                165                 170                 175
Ala Gly Ala Leu Ala Thr Gly Lys Leu Leu Gly Leu Thr Pro Asp Ser
            180                 185                 190
Met Glu Asp Ala Leu Gly Ile Ala Cys Thr Gln Ala Cys Gly Leu Met
        195                 200                 205
Ser Ala Gln Tyr Gly Gly Met Val Lys Arg Val Gln His Gly Phe Ala
    210                 215                 220
Ala Arg Asn Gly Leu Leu Gly Gly Leu Leu Ala Tyr Gly Gly Tyr Glu
225                 230                 235                 240
Ala Met Lys Gly Val Leu Glu Arg Ser Tyr Gly Gly Phe Leu Lys Met
                245                 250                 255
Phe Thr Lys Gly Asn Gly Arg Glu Pro Pro Tyr Lys Glu Glu Glu Val
            260                 265                 270
Val Ala Gly Leu Gly Ser Phe Trp His Thr Phe Thr Ile Arg Ile Lys
        275                 280                 285
Leu Tyr Ala Cys Cys Gly Leu Val His Gly Pro Val Glu Ala Ile Glu
    290                 295                 300
Lys Leu Gln Arg Arg Tyr Pro Glu Leu Leu Asn Arg Ala Asn Leu Ser
305                 310                 315                 320
Asn Ile Arg His Val Tyr Val Gln Leu Ser Thr Ala Ser Asn Ser His
                325                 330                 335
Cys Gly Trp Ile Pro Glu Glu Arg Pro Ile Ser Ser Ile Ala Gly Gln
            340                 345                 350
Met Ser Val Ala Tyr Ile Leu Ala Val Gln Leu Val Asp Gln Gln Cys
        355                 360                 365
Leu Leu Ala Gln Phe Ser Glu Phe Asp Asp Asn Leu Glu Arg Pro Glu
    370                 375                 380
Val Trp Asp Leu Ala Arg Lys Val Thr Pro Ser His Ser Glu Glu Phe
385                 390                 395                 400
Asp Gln Asp Gly Asn Cys Leu Ser Ala Gly Arg Val Arg Ile Glu Phe
                405                 410                 415
Asn Asp Gly Ser Ser Val Thr Glu Thr Val Glu Lys Pro Leu Gly Val
            420                 425                 430
Lys Glu Pro Met Pro Asn Glu Arg Ile Leu His Lys Tyr Arg Thr Leu
        435                 440                 445
Ala Gly Ser Val Thr Asp Glu Ser Arg Val Lys Glu Ile Glu Asp Leu
    450                 455                 460
Val Leu Ser Leu Asp Arg Leu Thr Asp Ile Thr Pro Leu Leu Glu Leu
465                 470                 475                 480
Leu Asn Cys Pro Val Lys Ser Pro Leu Val
                485                 490
```

<210> SEQ ID NO 3
<211> LENGTH: 490
<212> TYPE: PRT
<213> ORGANISM: Aspergillus terreus

<400> SEQUENCE: 3

```
Met Thr Lys Gln Ser Ala Asp Ser Asn Ala Lys Ser Gly Val Thr Ala
 1               5                  10                  15

Glu Ile Cys His Trp Ala Ser Asn Leu Ala Thr Asp Asp Ile Pro Ser
             20                  25                  30

Asp Val Leu Glu Arg Ala Lys Tyr Leu Ile Leu Asp Gly Ile Ala Cys
         35                  40                  45

Ala Trp Val Gly Ala Arg Val Pro Trp Ser Glu Lys Tyr Val Gln Ala
     50                  55                  60

Thr Met Ser Phe Glu Pro Pro Gly Ala Cys Arg Val Ile Gly Tyr Gly
 65                  70                  75                  80

Gln Lys Leu Gly Pro Val Ala Ala Ala Met Thr Asn Ser Ala Phe Ile
                 85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala Tyr Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Lys Leu Gln Arg Arg Tyr Pro Glu Leu Asn Arg Ala Asn Leu Ser
305                 310                 315                 320

Asn Ile Arg His Val Tyr Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365

Leu Leu Ala Gln Phe Ser Glu Phe Asp Asp Asn Leu Glu Arg Pro Glu
    370                 375                 380

Val Trp Asp Leu Ala Arg Lys Val Thr Pro Ser His Ser Glu Glu Phe
```

```
              385                 390                 395                 400
Asp Gln Asp Gly Asn Cys Leu Ser Ala Gly Arg Val Arg Ile Glu Phe
                405                 410                 415

Asn Asp Gly Ser Ser Val Thr Glu Thr Val Glu Lys Pro Leu Gly Val
                420                 425                 430

Lys Glu Pro Met Pro Asn Glu Arg Ile Leu His Lys Tyr Arg Thr Leu
                435                 440                 445

Ala Gly Ser Val Thr Asp Glu Ser Arg Val Lys Glu Ile Glu Asp Leu
                450                 455                 460

Val Leu Ser Leu Asp Arg Leu Thr Asp Ile Thr Pro Leu Leu Glu Leu
465                 470                 475                 480

Leu Asn Cys Pro Val Lys Ser Pro Leu Val
                485                 490

<210> SEQ ID NO 4
<211> LENGTH: 482
<212> TYPE: PRT
<213> ORGANISM: Aspergillus oryzae

<400> SEQUENCE: 4

Met Thr Val Thr Asp Ser Thr Pro Glu Gly Asn Val Thr Ala Glu Leu
 1               5                   10                  15

Cys Asn Trp Val Thr Glu Leu Lys Pro Ser Asp Ile Pro Ala Asp Val
                20                  25                  30

Leu Gln Arg Ala Lys His Leu Leu Asp Gly Ile Ala Cys Gly Leu
            35                  40                  45

Val Gly Ser His Val Pro Trp Ser Glu Gln Ala Ala Lys Ala Ile Asp
50                  55                  60

Asp Tyr Glu Pro Glu Gly Tyr Cys Ser Val Ile Gly Tyr Asn Arg Arg
65                  70                  75                  80

Tyr Gly Pro Gln Ala Ala Ala Ile Leu Asn Gly Ser Phe Ile Gln Ala
                85                  90                  95

Val Glu Leu Asp Asp Tyr His Ser Ala Ala Pro Leu His Ser Ala Ser
                100                 105                 110

Val Leu Leu Pro Ala Leu Phe Ala Ala Ala Glu Val Gln Ser Lys Gly
            115                 120                 125

His Arg Lys Ser Val Val Ser Gly Leu Asp Phe Leu Ala Leu Val
130                 135                 140

Val Gly Phe Glu Thr Gly Pro Arg Val Gly Ser Ala Met Tyr Gly Ala
145                 150                 155                 160

Asp Leu Leu Ser Arg Gly Trp His Ser Gly Pro Val Phe Gly Ser Pro
                165                 170                 175

Ala Ala Ala Ala Ala Ser Ser Lys Leu Leu Gly Leu Ser Pro Asp Asp
                180                 185                 190

Thr Glu Ser Ala Val Gly Ile Ala Cys Thr Gln Ala Gly Gly Leu Met
            195                 200                 205

Ala Ala Gln Tyr Glu Gly Met Val Lys Arg Val Gln His Ala Phe Ala
210                 215                 220

Ala Arg Asn Gly Leu Phe Gly Ala Leu Leu Ala Arg Asp Gly Tyr Val
225                 230                 235                 240

Gly Ile Lys Lys Val Phe Asp Arg Ser Tyr Gly Gly Phe Leu Thr Met
                245                 250                 255

Phe Thr Gln Gly Asn Gly Arg Thr Pro Gln Tyr Lys Pro Glu Glu Val
            260                 265                 270

Thr Thr Ala Leu Gly Lys Glu Trp Gln Thr Thr Asn Ile Arg Val Lys
```

```
                275                 280                 285
Leu His Ala Cys Val Gly Gly Cys His Gly Gln Ile Glu Ala Leu Glu
    290                 295                 300
Lys Leu Gln Arg Asn Tyr Pro Asp Arg Phe Ala Val Asp Gln Leu His
305                 310                 315                 320
Asn Ile Arg Arg Ile Thr Val Ser Leu Ser Glu Pro Val Phe Ala His
                325                 330                 335
Asp Gly Trp Ala Pro Glu Glu Arg Pro Leu Thr Ala Thr Gly Gly Gln
                340                 345                 350
Met Asn Ala Ala Tyr Ile Gly Ala Ala Gln Leu Val Tyr Gly Gln Val
                355                 360                 365
Leu Leu Asp Gln Phe Glu Pro His Ala Leu Asp Ser Asp Ala Val Trp
    370                 375                 380
Ser Leu Ile Asp Lys Thr Thr Cys Val His Ser Ser Glu Phe Asp Lys
385                 390                 395                 400
Pro Gly His Leu Cys Gly Ala Arg Ile Val Val Glu Phe Asn Asp Gly
                405                 410                 415
Glu Thr Val Glu Asp Val Val Ala Met Pro Lys Gly Phe Asp Pro Pro
                420                 425                 430
Ile Thr Asp Asp Glu Ile Arg Glu Lys Trp Arg Lys Leu Ala Ser Ser
                435                 440                 445
Val Ile Asp Ser Glu Arg Leu Gln Arg Ile Glu Asn Ser Val Leu Ser
                450                 455                 460
Leu Glu Thr Ser Ala Asp Val Ser Glu Leu Leu Ala Leu Ile Ser Gly
465                 470                 475                 480
Glu Leu

<210> SEQ ID NO 5
<211> LENGTH: 541
<212> TYPE: PRT
<213> ORGANISM: Aspergillus niger

<400> SEQUENCE: 5

Met Val Thr Ile Thr Ala Lys Ser Glu Ala Ala Ser Ala Thr Ser Pro
  1               5                  10                  15
Ile Ser Ser Asn Thr Ile Thr Thr Leu Asn Gly Val Gly Asp Pro
                20                  25                  30
Lys Asn Lys Glu Lys Asp Leu Gln Leu Gln Glu Lys Glu Gly Glu Glu
                35                  40                  45
Glu Glu Ile Ser Lys Glu Thr Lys Ala Tyr Asn Ser Ser Asn Gly Val
    50                  55                  60
Thr Ser Gln Leu Cys Thr Trp Ile Ala Ser Leu Gln Leu Asp Asp Ile
65                  70                  75                  80
Pro Asp Ser Val Arg Thr Arg Ala Lys Tyr Leu Phe Leu Asp Gly Ile
                85                  90                  95
Ala Cys Ala Leu Val Gly Ala Arg Val Pro Trp Ser Gln Lys Ala Phe
                100                 105                 110
Asp Ala Met Thr Ala Phe Glu Glu Arg Gly Lys His Val Val Ile Gly
                115                 120                 125
Tyr Glu Glu Arg Leu Gly Ala Ile Ala Ala Thr Leu Asn Gly Ser
    130                 135                 140
Trp Ile Gln Ala Cys Glu Val Asp Asp Tyr His Ser Val Ala Pro Leu
145                 150                 155                 160
His Ser Gln Ala Val Val Ile Pro Pro Leu Phe Ala Ala Ala Val Gly
                165                 170                 175
```

```
Ala Arg Asp His Pro Thr Thr Pro Arg Ile Ile Asp Gly Arg Thr Leu
            180                 185                 190

Leu Leu Ala Ser Val Val Gly Phe Glu Ile Gly Pro Arg Val Gly Met
        195                 200                 205

Ala Leu His Gly Thr Glu Met Leu Ala Lys Gly Trp His Cys Gly Ser
    210                 215                 220

Val Phe Gly Ala Pro Ala Ala Gly Ser Ser Ala Lys Leu Leu Gly
225                 230                 235                 240

Leu Ser Ala Gly Gln Ile Glu Asp Ala Ile Gly Val Ala Ala Thr Gln
                245                 250                 255

Ala Cys Gly Leu Met Ala Ala Gln Tyr Asp Gly Met Val Lys Arg Met
            260                 265                 270

His His Gly Phe Ala Ala Arg Asn Gly Leu Leu Gly Thr Met Leu Ala
        275                 280                 285

Trp Gly Gly Tyr Glu Gly Ile Lys Lys Val Phe Glu Arg Pro Tyr Gly
    290                 295                 300

Gly Phe Leu Ala Met Phe Gly Leu Gly Ser Lys Asn Thr Pro Ser Ser
305                 310                 315                 320

Lys Pro Glu Glu Val Ala Lys Asp Leu Gly Thr Phe Trp His Thr Ala
                325                 330                 335

Glu Trp Ile Arg Leu Lys Leu His Ala Cys Cys Gly Ile His Gly
            340                 345                 350

Thr Ile Glu Cys Leu Ala Glu Met Gln Glu Met Tyr Pro Glu Arg Leu
        355                 360                 365

Gly Arg Glu Lys Leu Gly Glu Ile Lys Glu Ile Arg Ile Gln Leu Ser
    370                 375                 380

Asp Ala Val Phe His His Cys Gly Trp Ala Pro Glu Thr Arg Pro Leu
385                 390                 395                 400

Thr Pro Thr Gly Ala Gln Met Asn Thr Ala Phe Val Ala Ala Ser Gln
                405                 410                 415

Leu Val Asp Gly Gln Val Leu Glu Gln Phe Ser Ser Gly Lys Leu
            420                 425                 430

Asp Arg Asp Glu Ile Trp Glu Leu Ile Gly Lys Thr Ser Cys Val His
        435                 440                 445

Thr Thr Glu Leu Asp Gln Pro Asn Ile Gly Cys Gly Ala Leu Ile Ser
    450                 455                 460

Ile Ala Phe Ala Asp Gly Ser Gln Val Gln His Ser Leu Leu Lys Pro
465                 470                 475                 480

Lys Gly Val Asp Glu Pro Ile Ser Asn Glu Ile Leu Glu Lys Phe
                485                 490                 495

Arg Arg Leu Thr Gly Gly Leu Ile Gly Val Glu Arg Gln Glu Lys Ile
            500                 505                 510

Glu Arg Ala Val Leu Gly Met Glu Glu Leu Gln Asp Val Asn Glu Leu
        515                 520                 525

Ile Glu Leu Leu Ser Val Asn Val Val Asn Pro Leu Gln
    530                 535                 540

<210> SEQ ID NO 6
<211> LENGTH: 485
<212> TYPE: PRT
<213> ORGANISM: Aspergillus niger

<400> SEQUENCE: 6

Met Thr Thr Leu Thr Pro Thr Pro Ala Asn Ser Thr Ser Thr Pro Ile
1               5                   10                  15
```

```
Thr His Thr Leu Ser Thr Trp Leu Glu Asp Leu Thr Pro Glu Ser Ile
            20              25              30
Pro Val Glu Val Arg Glu Arg Ala Lys Tyr Leu Ile Leu Asp Gly Leu
            35              40              45
Ala Cys Ala Leu Leu Gly Ala Arg Leu Pro Trp Ser Val Lys Ala His
50              55              60
Asp Ala Ile Thr Thr Ile Glu Gly Gln Gly Lys Cys Thr Val Ile Gly
65              70              75              80
Trp Asn Glu Thr Leu Ser Pro Asn Ala Ala Leu Leu Asn Ser Thr
            85              90              95
Phe Leu Gln Gly Phe Asp Leu Asp Asp Ile His Val Glu Ala Pro Ile
            100             105             110
His Thr Met Ser Val Ile Leu Pro Ala Ile Leu Ala Ala Ala Glu Gln
            115             120             125
Glu His Gly Gly Ser Thr Arg Pro Ile Ser Gly Asn Asp Phe Ile Thr
        130             135             140
Ala Thr Val Ala Gly Cys Glu Thr Gly Pro Arg Val Gly Tyr Ala Leu
145             150             155             160
Gly Gly Thr His Met Leu Thr Ile Gly Trp His Cys Gly Ala Ile Phe
            165             170             175
Gly Pro Ala Ala Ser Ala Ala Val Ser Lys Leu Leu Asn Leu Pro
            180             185             190
Ala Ala Gln Ile Glu Asp Ala Leu Gly Met Ala Cys Thr Gln Ala Cys
        195             200             205
Gly Leu Met Ser Val Gln Phe Glu Ser Met Val Lys Arg Met Gln His
    210             215             220
Gly Phe Ala Ser Arg Ser Gly Val Leu Ala Thr Tyr Leu Ala Lys Gln
225             230             235             240
Gly Phe Thr Gly Ile Lys Glu Ile Phe Asp Arg Glu Tyr Gly Gly Phe
            245             250             255
Leu Lys Met Phe Ser Tyr Gly Ala Glu Thr Glu Arg Lys Tyr Tyr Pro
            260             265             270
Glu Glu Val Cys Lys Gly Leu Gly Glu Val Trp Gln Thr Lys Lys Ile
        275             280             285
Lys Gln Lys Leu His Ala Leu Cys Ala Val Ser His Cys Thr Val Asp
    290             295             300
Cys Ile Lys Asp Leu Gln Ala Met Tyr Pro Ala Lys Met Gly Glu Trp
305             310             315             320
Lys Lys Ile Val Lys Ile Glu Ala Glu Met Ala Arg Ala Ala Met Lys
            325             330             335
Lys Gly Gly Trp Ala Pro Glu Lys Pro Ala Thr Ala Thr Ala Ala Gln
            340             345             350
Met Ser Ile Pro Tyr Ala Val Ala Leu Gln Val Leu Asp Gly Glu Ile
        355             360             365
Val Pro Gly Gln Phe Ala Pro Gly Met Leu Asn Arg Glu Glu Leu Trp
    370             375             380
Asp Val Ile Arg Leu Val Glu Cys Arg Glu Ala Lys Glu Leu Asp Asn
385             390             395             400
Thr Trp Ala Gln Arg Val Lys Ile Thr Phe Glu Asp Gly Glu Val Val
            405             410             415
Glu Lys Leu Leu Lys Ala Pro Lys Gly Val His Pro Gly Val Thr Asn
            420             425             430
Glu Glu Val Leu Gln Lys Trp Arg Ala Val Thr Lys Gly Val Ile Ser
```

```
                    435                 440                 445
Glu Glu Arg Gln Lys Lys Ile Glu Glu Ile Val Leu Asn Leu Glu Glu
            450                 455                 460
Val Glu Asp Val Ala Gly Val Leu Gly Glu Leu Leu Arg Glu Thr
465                 470                 475                 480
Val Asn Val Leu Gln
                485

<210> SEQ ID NO 7
<211> LENGTH: 504
<212> TYPE: PRT
<213> ORGANISM: Gibberella zeae

<400> SEQUENCE: 7

Met Ser His Gly Cys Ile Gly Ile Asn Tyr Arg Leu Ile Ser Phe Val
  1               5                  10                  15
Leu Thr Asn Ser Phe Pro Thr Thr Tyr Asn Pro Ser Met Ser Glu Ser
                 20                  25                  30
Lys Pro Ser Pro Thr Val Gln Leu Ser Arg Trp Val Ser Gln Leu Lys
             35                  40                  45
Leu Asp Asp Ile Pro Glu Gln Val Arg Thr Arg Ala Lys Tyr Leu Ile
 50                  55                  60
Leu Asp Gly Ile Ala Cys Ala Phe Val Gly Ser His Leu Pro Trp Ser
 65                  70                  75                  80
Glu Thr Ala Ala His Ala Ile Phe Lys Leu Glu Pro Thr Gln Gly Asp
                 85                  90                  95
Ala Ser Leu Val Gly Trp Gly Arg Lys Ala Thr Ala Leu Ser Ala
            100                 105                 110
Ala Leu Leu Asn Gly Thr Phe Ile Gln Gly Phe Glu Leu Asp Asp Trp
            115                 120                 125
His Ser Glu Ala Pro Leu His Ser Asn Ser Ile Ile Leu Pro Ala Leu
            130                 135                 140
Ile Ala Ala Ala Gln Asn Ser His Ser Thr Thr Ser Gly Lys Asp Phe
145                 150                 155                 160
Leu Leu Ala Thr Ile Ala Gly Tyr Glu Ile Gly Pro Arg Val Gly Arg
                165                 170                 175
Ala Leu Trp Gly Thr His Val Leu Ser Ser Gly Trp His Ser Gly Ala
            180                 185                 190
Val Phe Gly Pro Ala Ala Ala Ser Ser Val Ser Lys Leu Tyr Gly
            195                 200                 205
Phe Ser Ala Asp Lys Ile Glu Asp Ala Phe Gly Ile Ala Cys Thr Gln
210                 215                 220
Ala Cys Gly Leu Met Ser Ala Gln Phe Glu Ser Asp Val Lys Arg Met
225                 230                 235                 240
His His Gly Ile Ala Ala Arg Asn Gly Leu Met Ala Ala Val Leu Ala
                245                 250                 255
Arg Asp Gly Tyr Val Gly Ile Lys Lys Val Phe Glu Arg Glu Tyr Gly
            260                 265                 270
Gly Phe Leu Lys Gln Phe Ser Ser Gly Asn Gly Arg Glu Pro Gln Tyr
            275                 280                 285
Arg Leu Asp Glu Leu Thr Ser Glu Leu Gly Thr Lys Trp Gln Thr Asn
            290                 295                 300
Gly Ile Arg Ile Lys Pro Tyr Ala Ala Met Ala Gly Thr His Pro Ser
305                 310                 315                 320
Ile Asp Cys Ile Arg Arg Leu Gln Glu Gln Asn Pro Glu Arg Met Asn
```

```
                    325                 330                 335
Lys Phe Asp Glu Ile Thr Lys Ile Glu Ile Leu Leu Gly Glu Ala Ala
                340                 345                 350

Phe His His Gly Gly Trp Lys Ala Lys Lys Pro Leu Thr Ala Thr Gly
            355                 360                 365

Ala Gln Met Ser Asn Ser Phe Thr Thr Ala Leu Gln Ile Val His Arg
        370                 375                 380

Gln Val Leu Met Ala Gln Phe Thr Ser Asn Met Leu Asn Asp Glu Arg
385                 390                 395                 400

Val Trp Arg Leu Val His Met Thr Glu Cys Lys Leu Tyr Ile Thr Asp
                405                 410                 415

Gly Asp Ser Ile Gly Cys Gln Glu Val Arg Ile Glu Phe Gln Asp Gly
            420                 425                 430

Thr Ala Leu His His Ala Val Gln Asn Ala Tyr Gly Val Asp Pro Pro
        435                 440                 445

Leu Ser Asn Glu Asp Ile Val Gly Lys Trp Arg Asp Leu Thr Lys Gly
    450                 455                 460

Ile Val Glu Asn Lys Val Leu Asp Lys Ile Glu Glu Ile Val Leu Ser
465                 470                 475                 480

Leu Glu Glu Leu Asp Asp Leu Ser Thr Leu Cys Asp Leu Leu Gly Gln
                485                 490                 495

Ile Ala Lys Ser Pro Leu Ala Glu
            500

<210> SEQ ID NO 8
<211> LENGTH: 481
<212> TYPE: PRT
<213> ORGANISM: Pichia stipitis

<400> SEQUENCE: 8

Met Asp Leu Ser Leu Pro Tyr Asp Arg Lys Ile Asn Ser Arg Ser Val
1               5                   10                  15

Thr Thr Glu Leu Ser Glu Trp Val Ala Gln Leu Lys Trp Glu Asp Val
            20                  25                  30

Pro Asp Lys Ile Lys Asp Arg Thr Lys Phe Leu Ile Leu Asp Gly Ile
        35                  40                  45

Gly Cys Ala Leu Val Gly Ala His Leu Pro Trp Ser Glu Glu Ala Val
    50                  55                  60

Glu Ala Val Leu Lys Phe Glu Thr Pro Gly Gly Asp Ser Pro Ile Val
65                  70                  75                  80

Gly Trp Lys Gly Arg Lys Thr Gly Leu Val Ser Ala Ala Leu Leu Asn
                85                  90                  95

Ser Thr Phe Ile Gln Gly Phe Glu Leu Asp Asp Tyr His Ser Tyr Ala
            100                 105                 110

Pro Leu His Ser Asn Ser Ile Ile Leu Pro Thr Leu Leu Ser Leu Cys
        115                 120                 125

Ser Lys Asp Pro Ser Lys His Ser Gly Arg Asp Phe Ile Leu Ala Thr
    130                 135                 140

Ile Val Gly Phe Glu Val Gly Pro Arg Val Gly Lys Ser Ile Gly Gly
145                 150                 155                 160

Ser Ser Ile Leu Ser Leu Gly Trp His Ser Gly Ala Val Phe Gly Pro
                165                 170                 175

Pro Val Ala Ala Ala Ser Ala Cys Lys Phe Leu Ser His Asn Ala Ile
            180                 185                 190

Gln Ile Glu Asp Ala Phe Gly Ile Ala Cys Thr Gln Ala Ser Gly Leu
```

```
            195                 200                 205
Met Ser Ala Gln Phe Glu Ser Ser Val Lys Arg Met Gln His Gly Phe
210                 215                 220

Ala Val Arg Asn Gly Leu Phe Ala Ala Leu Leu Ala Asp Ser Asn Tyr
225                 230                 235                 240

Lys Gly Ile Ser Lys Val Phe Glu Arg Lys Tyr Gly Tyr Ile Pro
                245                 250                 255

Val Phe Thr Leu Gly Gly Leu Lys Pro Lys Pro Glu Glu Ile Ser Leu
                260                 265                 270

Gly Leu Gly Glu Ile Trp Arg Ile Glu Gly Thr Leu Val Lys Leu His
                275                 280                 285

Pro Cys Met Gly Gly Ile His Ser Thr Cys Glu Cys Val Glu Glu Leu
290                 295                 300

Val Asn Ser Gln Glu Val Asp Ser Lys Asn Ile Glu Gly Val Lys Ile
305                 310                 315                 320

Glu Leu Gly Lys Ala Ala Phe His His Gly Gly Trp Lys Ala Gln Arg
                325                 330                 335

Pro Ile Asn Val Ile Gly Ala Gln Met Asn Asn Ser Tyr Ile Ala Ala
                340                 345                 350

Ser Ile Phe Val Asp Gly Ser Leu Gln Met Lys Ser Phe Thr Glu Asp
                355                 360                 365

Lys Leu Asn Arg Glu Glu Val Trp Asp Ile Val Lys Lys Thr Gln Cys
                370                 375                 380

Val Glu Asn Asn Phe Glu Gly Gln Ile Asp Pro Gln Phe Lys Leu Cys
385                 390                 395                 400

Thr Gln Val Thr Val Thr Thr Lys Asp Gly Lys Glu His Ile Ser Arg
                405                 410                 415

Val Val Asn Pro Lys Gly Val Leu Pro Leu Thr Gly Lys Glu Ile
                420                 425                 430

Val Glu Lys Phe Lys Asn Leu Thr Asn Asn Val Ile Thr Lys Asp Gln
                435                 440                 445

Gln Asp Lys Ile Ile Glu Thr Val Leu Asn Leu Asp Lys Phe Asp Met
                450                 455                 460

Ser Cys Leu Leu Asp Ser Leu Asp Ile Asp Thr Ser Asn Pro Leu Ala
465                 470                 475                 480

Val

<210> SEQ ID NO 9
<211> LENGTH: 670
<212> TYPE: PRT
<213> ORGANISM: Aspergillus terreus

<400> SEQUENCE: 9

Met Ala Lys Leu Leu Glu Arg Ser Ile Ala Trp Val Leu Tyr Ala Arg
  1               5                  10                  15

Arg Gly His Asp Ser Gly Leu Leu His Arg Ser Pro Pro Phe Ala Gln
                 20                  25                  30

His Pro Ser Pro Thr Met Thr Val Glu Cys Thr Ile Gly Pro Ser Glu
             35                  40                  45

Ser Pro Ile Pro Pro Glu Tyr Ser Ala Phe Glu His Gly Leu Phe Pro
         50                  55                  60

Thr Phe Ser Trp Thr Pro Pro Asn Ala Ala Glu Tyr Leu Leu Val
 65                  70                  75                  80

Val Glu Asp Pro Asp Ala Pro Leu Ala Glu Pro Val Val His Gly Leu
                 85                  90                  95
```

```
Tyr Tyr Gly Ile Pro Ala Ser Lys Thr Ser Val Ser Ser Thr Asp Phe
            100                 105                 110

Glu Pro Val Gly Asp Asp Gly Glu Leu Arg Leu Asn Gly Gly Phe Lys
            115                 120                 125

Tyr Gly Leu Asn Arg Arg Asn Val Tyr Met Pro Pro Arg Gly Phe
        130                 135                 140

Leu Gly His Gly Pro His Arg Tyr Phe Tyr Gln Ile Val Ala Leu Ser
145                 150                 155                 160

Glu Arg Ile Glu Gln Ser Gln Leu Ser Ala Pro Ala Thr Lys Glu Glu
                165                 170                 175

Val Val Arg Cys Leu Gln Asp Lys Ile Ile Ser Met Thr Glu His Ser
            180                 185                 190

Gly Leu Thr Thr Gln Gln Asn Asn Gly Val Thr Arg Gln Leu Cys Ser
        195                 200                 205

Trp Val Asp Arg Leu Arg Leu Ala Asp Val Pro Glu Asp Gln Leu Val
    210                 215                 220

Arg Ala Lys Tyr Leu Ile Leu Asp Gly Ile Gly Cys Thr Ile Val Gly
225                 230                 235                 240

Ala His Leu Pro Trp Ser Glu Lys Ala Ala His Ala Ile Leu Asp Met
                245                 250                 255

Glu Pro Pro Gly Asp Cys Pro Val Trp Gly Tyr Asn Lys Lys Ile Gly
            260                 265                 270

Pro Leu Pro Ser Ala Leu Val Asn Ser Thr Ala Ile Gln Ala Phe Glu
        275                 280                 285

Leu Asp Asp Trp His Ser Leu Ala Pro Leu His Ser Asn Ala Ile Leu
    290                 295                 300

Leu Pro Ala Leu Phe Ala Ala Ala His Gln Lys Ala Arg Gly Gly
305                 310                 315                 320

Pro Ala Ile Asn Gly Ala Ser Leu Leu Leu Ser Thr Ile Val Gly Tyr
                325                 330                 335

Glu Ile Gly Pro Arg Val Gly Leu Cys Leu His Gly Ser His Met Leu
            340                 345                 350

Thr Arg Gly Trp His Ser Gly Val Val Phe Gly His Ala Ala Ser Ala
        355                 360                 365

Ala Ala Val Ser Lys Leu Leu Gly Leu Gly Ser Asp Ala Ile Glu Asp
    370                 375                 380

Ala Val Gly Ile Ala Cys Thr Gln Ala Cys Gly Leu Met Ser Ala Gln
385                 390                 395                 400

Phe Gly Ser Asp Val Lys Arg Met Gln His Gly Phe Ala Ala Arg Asn
                405                 410                 415

Gly Leu Phe Gly Ala Leu Leu Ala Lys Ser Gly Tyr Thr Gly Ile Lys
            420                 425                 430

Arg Val Phe Glu Glu Pro Tyr Gly Gly Phe Leu Ala Val Phe Gly Glu
        435                 440                 445

Gly Ser Gly Lys Glu Pro Pro Phe Leu Ala Glu Glu Leu Val Asn Gly
    450                 455                 460

Leu Gly Gln Thr Trp Gln Leu Asp Ala Ile Arg Val Lys Pro Tyr Ala
465                 470                 475                 480

Ser Met Ala Gly Thr His Cys Ile Ile Asp Ser Val Ala Ala Leu Gln
                485                 490                 495

Arg Glu Tyr Pro Glu Lys Leu Lys Asp Leu Asp Ala Ile Val Ser Ile
            500                 505                 510

Ala Ile Glu Met Ser Glu Pro Ala Trp Lys His Gly Gly Trp Lys Ala
```

```
                515                 520                 525
His Arg Pro Leu Thr Ala Thr Gly Ala Gln Met Ser Cys Ala Tyr Val
530                 535                 540

Ala Ala Val Gln Leu Val Asp Gly Gln Val Leu Pro Gln Gln Phe Gln
545                 550                 555                 560

Pro Glu Lys Val Asp Arg Asp Val Ile Trp Arg Leu Val Asp Lys Thr
                565                 570                 575

Glu Cys Phe His Thr Pro Glu Leu Gly Glu Lys Tyr Glu Gln Arg Val
                580                 585                 590

Thr Val Ala Phe Gln Asp Gly Ser Lys Ile Ser Arg Leu Leu Glu Ala
            595                 600                 605

Pro Lys Gly Val Ser Pro Leu Ser Asn Glu Glu Ile Leu Asp Lys
        610                 615                 620

Phe Arg Met Phe Thr Tyr Gly Leu Val Glu Lys Arg Arg Asp Ala
625                 630                 635                 640

Ile Glu Gln Leu Val Leu Arg Ile Glu Tyr Val Glu Asp Val Ser Ala
                645                 650                 655

Leu Glu Glu Leu Leu Ser Gly Pro Thr Leu Ser Pro Ile Ala
            660                 665                 670

<210> SEQ ID NO 10
<211> LENGTH: 476
<212> TYPE: PRT
<213> ORGANISM: Mycobacterium avium subsp. paratuberculosis

<400> SEQUENCE: 10

Met Thr Ala Leu Gln Gln Glu Thr Val Thr Asp Pro Val Gly Pro Thr
1               5                   10                  15

Gly Leu Leu Ala Thr Trp Val Ala Glu Leu Thr Leu Asp Asp Val Pro
            20                  25                  30

Ala Pro Val Val Asp Arg Ala Lys His Leu Leu Leu Asp Gly Ile Gly
        35                  40                  45

Cys Ala Leu Val Gly Ala Gln Leu Pro Trp Ser Arg Ile Ala Thr Asp
    50                  55                  60

Ala Val Leu Ala Leu Glu Gly Ser Gly Asp Ser Ile Val Ile Gly Thr
65                  70                  75                  80

Gly Arg Arg Thr Ser Ala Pro Ala Ala Val Leu Asn Gly Thr Phe
                85                  90                  95

Ile Gln Gly Phe Glu Leu Asp Asp Phe His Pro Leu Ala Pro Leu His
            100                 105                 110

Ser Cys Ser Leu Leu Ile Pro Ala Leu Leu Ser Thr Ala Ala Thr Arg
        115                 120                 125

Ser Ala Thr Thr Thr Gly Arg Glu Leu Leu Ala Ala Ile Ala Gly
    130                 135                 140

Phe Glu Val Gly Pro Arg Val Gly His Ala Leu His Gly Thr Gln Met
145                 150                 155                 160

Leu Asp Arg Gly Trp His Ser Gly Pro Val Phe Gly Thr His Ala Ala
                165                 170                 175

Ala Met Ala Ser Gly Lys Leu Arg Gly Leu Pro Ala Gln Leu Glu
            180                 185                 190

Asp Ala Leu Gly Leu Ala Gly Thr Gln Ser Ala Gly Leu Met Ala Ala
        195                 200                 205

Gln Tyr Glu Ala Met Ser Lys Arg Met His His Gly Leu Ala Ala Arg
    210                 215                 220

Asn Gly Phe Tyr Ala Ala Gly Leu Ala Ala Ala Gly Tyr Thr Gly Ile
```

```
                    225                 230                 235                 240
Lys Arg Val Phe Glu Arg Glu Tyr Gly Gly Phe Leu Ser Val Phe Gly
                    245                 250                 255

Glu Gly His Asp Pro Asp Ala Ala Leu Thr Ala Asp Leu Gly Gln
                260                 265                 270

Arg Trp Glu Thr Ser Leu Ile Met Val Lys Ser Tyr Ala Ala Met Gly
                275                 280                 285

Gly Leu His Gly Ala Ile Asp Ala Ala Arg Arg Leu Arg Asn Ser Val
                290                 295                 300

Ala Pro Gln Asn Ile Ser Ser Val Asp Ile Thr Val Gly Glu Thr Val
305                 310                 315                 320

Tyr Lys His Gly Trp Trp Leu Pro Glu Arg Pro Leu Thr Pro Ile Gly
                325                 330                 335

Ala Gln Met Asn Ile Gly Tyr Ala Thr Val Ala Ala Leu Leu Asp Gly
                340                 345                 350

Asn Val Leu Pro Glu Gln Phe Thr Ala Ala Arg Leu Asp Ala Asp Asp
                355                 360                 365

Ile Trp Ala Leu Ile Ser Ala Thr Arg Val His Leu Asp Glu Ser Leu
370                 375                 380

Ala Asp Ala Asp Ile Thr Glu Lys Phe Arg Thr Asp Leu Ala Val Thr
385                 390                 395                 400

Thr Arg Glu Gly Thr Val His Arg Ala Arg Val Thr Leu Pro His Gly
                405                 410                 415

Ala Pro Asn Asp Pro Val Thr Asn Asp Glu Val Val Ala Lys Phe His
                420                 425                 430

Ala Leu Ala Asp Arg Val Thr Ser Arg Gly Arg Ala Ala Ile Glu
                435                 440                 445

Arg Ala Val Ile Arg Leu Asp Asp Leu Thr Asp Val Glu Asn Leu Met
450                 455                 460

Asp Leu Leu Ala Asp Pro Val Ala Gly Ala Leu Asp
465                 470                 475

<210> SEQ ID NO 11
<211> LENGTH: 477
<212> TYPE: PRT
<213> ORGANISM: Mycobacterium smegmatis

<400> SEQUENCE: 11

Met Gly Gln Val Asn Thr Leu Thr Asp Pro Ser Ala Pro Glu Gly Pro
  1               5                  10                  15

Thr Gly Gln Leu Val Asn Trp Val Arg Thr Leu Glu Trp Asp Gln Val
                20                  25                  30

Pro Glu His Val Arg Val Arg Ala Ala His Leu Leu Asp Gly Ile
                35                  40                  45

Gly Cys Ala Leu Val Gly Ala Gln Leu Pro Trp Ser Arg Leu Ala Thr
 50                  55                  60

Asp Ala Val Leu Gly Ile Glu Gly Asp Gly Ala Val Pro Val Ile Gly
 65                  70                  75                  80

Thr Gly Arg Thr Ser Thr Pro Val Gly Ala Val Leu Leu Asn Ser Thr
                85                  90                  95

Phe Ile Gln Gly Phe Glu Leu Asp Asp Phe His Pro Phe Ala Pro Leu
                100                 105                 110

His Ser Ala Ser Leu Val Val Pro Ala Leu Leu Ala Thr Thr Ala His
                115                 120                 125

Leu Asn Arg Pro Val Ser Gly Lys Glu Leu Leu Met Ala Ala Ile Val
```

```
                130                 135                 140
Gly Phe Glu Thr Gly Pro Arg Ile Gly Arg Ala Leu Gly Gly Thr Glu
145                 150                 155                 160

Met Leu Ser Arg Gly Trp His Ser Gly Pro Val Phe Gly Gly Ile Gly
                165                 170                 175

Thr Ala Leu Ala Cys Gly Arg Leu Arg Gly Leu Asn Gly Glu Gln Leu
            180                 185                 190

Glu Asp Ala Val Gly Phe Ala Ala Thr Gln Ser Ala Gly Leu Met Ser
        195                 200                 205

Ala Gln Tyr Glu Ala Met Gly Lys Arg Met Gln His Gly Phe Ala Ala
    210                 215                 220

Arg Asn Gly Phe Tyr Ser Ala Leu Ala Gln Ser Gly Tyr Thr Gly
225                 230                 235                 240

Ile Asp Gln Val Leu Glu Arg Pro Tyr Gly Phe Leu Ala Val Tyr
                245                 250                 255

Gly Glu Gly His Arg Pro Asp Ala Ser Ala Ile Thr Arg Gly Leu Gly
            260                 265                 270

Asp Glu Trp Glu Thr Thr Ala Ile Met Val Lys Ser Trp Ala Val Met
        275                 280                 285

Gly Gly Leu His Gly Val Val Glu Ala Ala Arg Ile Leu Arg Asn Arg
    290                 295                 300

Leu His Gly Arg Thr Ile Glu His Ile Asp Ile Arg Val Gly Asp Val
305                 310                 315                 320

Val Tyr His His Gly Trp Trp Gln Pro Gln Arg Pro Leu Thr Ala Ile
                325                 330                 335

Gly Ala Gln Met Asn Ile Gly Tyr Ala Ala Ala Val Thr Leu Leu Asp
            340                 345                 350

Gly Val Ala Leu Pro Gln Gln Phe Thr Ala Glu Arg Leu Asp Ala Asp
        355                 360                 365

Asp Val Trp Arg Leu Leu Ala Arg Thr His Val Glu Leu Asp Glu Ser
    370                 375                 380

Ile Asp Glu Leu Pro Pro Thr Glu Arg Phe Gln Thr His Leu Thr Leu
385                 390                 395                 400

Thr Phe Ser Asp Gly Ser Thr Glu Thr Ala Ser Val Met Ala Pro His
                405                 410                 415

Gly Asn Pro Arg Asp Pro Val Thr Asn His Glu Val Val Asp Lys Phe
            420                 425                 430

Ala Arg Leu Val Ala Pro Val Met Pro Ala Asp Arg Ala Ala Ile
        435                 440                 445

Gln His Ala Phe Leu Gly Leu Pro Glu Val Pro Asp Val Ala Pro Leu
    450                 455                 460

Val Glu Leu Leu Ser Gly Pro Val Gly Arg Val Leu Asp
465                 470                 475

<210> SEQ ID NO 12
<211> LENGTH: 464
<212> TYPE: PRT
<213> ORGANISM: Salinispora arenicola

<400> SEQUENCE: 12

Met Ala Gly Thr Thr Pro Thr Asp Ala Asp Gly Pro Thr Gly Arg Leu
1               5                   10                  15

Ala Thr Trp Leu Ala Glu Thr Ser Val Asp Ala Ile Pro Thr Glu Val
            20                  25                  30

Ser Thr Arg Ala Arg His Leu Ile Leu Asp Gly Ile Gly Cys Leu Leu
```

```
                  35                  40                  45
Val Gly Ala Arg Leu Pro Trp Ser Arg Ile Ala Val Gln Ser Leu Thr
 50                  55                  60

Val Glu Pro Gly Ala Ser Val Val Ala Gly Trp Asp Arg Thr Ala Ser
 65                  70                  75                  80

Ala Pro Thr Ala Val Met Leu Asn Ser Ser Phe Ile Gln Gly Phe Glu
                 85                  90                  95

Leu Asp Asp Val Ser Tyr Arg Ile Pro Trp His Ala Asn Ala Val Val
                100                 105                 110

Leu Pro Val Leu Leu Ala Val Ala Gly Leu Arg Gly Lys Val Thr Gly
                115                 120                 125

Ala Glu Phe Leu Arg Ala Glu Val Leu Gly Phe Glu Thr Gly Ala Arg
    130                 135                 140

Val Gly Leu Ala Leu Arg Gly Pro Gln Leu Val Thr His Gly Trp His
145                 150                 155                 160

Ser Gly Ala Val Phe Gly Gly Pro Gly Ala Ala Ala Gly Gly Val
                165                 170                 175

Leu Tyr Gly Leu Thr Pro Ala Arg Phe Glu Asp Ala Leu Gly Ile Ala
                180                 185                 190

Ala Thr Gln Ser Cys Gly Leu Met Ala Asn Glu Ala Met Val Lys Arg
    195                 200                 205

Met Gln His Gly Phe Ala Ala Arg Asn Gly Leu Val Ala Ala Met Leu
210                 215                 220

Ala Ala Gly Gly Tyr Gly Gly Thr Lys Arg Ile Phe Glu Arg Gly Tyr
225                 230                 235                 240

Gly Gly Tyr Leu Thr Val Tyr Gly Ala Gly His Gly Pro Asp Pro Ser
                245                 250                 255

His Ile Asp Asp Ala Leu Gly Glu His Trp Tyr Leu Arg Glu Gln Thr
                260                 265                 270

Ile Lys Pro Tyr Ala Ala Met Gly Tyr Thr His Pro Ala Ile Asp Ala
                275                 280                 285

Ala Leu Ala Leu Arg Ala Ala Asp Arg Val Asp Pro Ala Ala Thr Ala
    290                 295                 300

Arg Ile Glu Ile Glu Val Ala Asp Ser Val Phe Asp His Thr Ala Phe
305                 310                 315                 320

Pro Ile His Arg Pro Ile Glu Ser Val Ala Ala Gln Met Ser Val Arg
                325                 330                 335

Tyr Val Thr Ala Ala Ala Leu Leu Asp Gly Thr Val Ser Leu Glu Gln
                340                 345                 350

Leu Arg Pro Glu Arg Leu Asp Arg Asp Val Trp Arg Leu Val Asp
    355                 360                 365

Arg Thr Thr Val Thr Arg Gly Ser Gly Ser Ala Ser Gln Gly Arg Val
370                 375                 380

Arg Leu Thr Asp Val Asp Gly Arg Thr His Glu His Arg Thr Glu Ala
385                 390                 395                 400

Pro Leu Gly Ser Val Glu Arg Pro Leu Gly Asp Ala Ala Ile Val Asp
                405                 410                 415

Lys Tyr Arg Asp Leu Thr Gly Arg Val Val Asp Arg His Arg Gln Arg
                420                 425                 430

Ala Ile Glu Asp Leu Val Leu His Leu Asp Glu His Arg Asp Gly Pro
    435                 440                 445

Ala Ala Leu Leu Thr Leu Leu Ala Pro Ala Val Gly Asp Ala Leu Asp
    450                 455                 460
```

<210> SEQ ID NO 13
<211> LENGTH: 476
<212> TYPE: PRT
<213> ORGANISM: Mycobacterium avium

<400> SEQUENCE: 13

Met Thr Ala Leu Gln Gln Glu Thr Val Thr Asp Pro Val Gly Pro Thr
1 5 10 15

Gly Leu Leu Ala Thr Trp Val Ala Glu Leu Thr Leu Asp Asp Val Pro
20 25 30

Pro Pro Val Val Asp Arg Ala Lys His Leu Leu Leu Asp Gly Ile Gly
35 40 45

Cys Ala Leu Val Gly Ala Gln Leu Pro Trp Ser Arg Ile Ala Thr Asp
50 55 60

Ala Val Leu Ala Leu Glu Gly Ser Gly Asp Ser Ile Val Ile Gly Thr
65 70 75 80

Gly Arg Arg Thr Ser Ala Pro Ala Ala Ala Val Leu Asn Gly Thr Phe
85 90 95

Ile Gln Gly Phe Glu Leu Asp Asp Phe His Pro Leu Ala Pro Leu His
100 105 110

Ser Cys Ser Leu Leu Ile Pro Ala Leu Leu Ser Thr Ala Ala Thr Arg
115 120 125

Ser Ala Thr Thr Thr Gly Arg Glu Leu Leu Pro Ala Ala Ile Ala Gly
130 135 140

Phe Glu Val Gly Pro Arg Val Gly His Ala Leu His Gly Thr Gln Met
145 150 155 160

Leu Asp Arg Gly Trp His Ser Gly Pro Val Phe Gly Thr His Ala Ala
165 170 175

Ala Met Ala Ser Gly Lys Leu Arg Gly Leu Pro Pro Ala Gln Leu Glu
180 185 190

Asp Ala Leu Gly Leu Ala Gly Thr Gln Ser Ala Gly Leu Met Ala Ala
195 200 205

Gln Tyr Glu Ala Met Ser Lys Arg Met His His Gly Leu Ala Ala Arg
210 215 220

Asn Gly Phe Tyr Ala Ala Gly Leu Ala Ala Ala Gly Tyr Thr Gly Ile
225 230 235 240

Lys Arg Val Phe Glu Arg Glu Tyr Gly Gly Phe Leu Ser Val Phe Gly
245 250 255

Glu Gly His Asp Pro Asp Ala Ala Ala Leu Thr Ala Asp Leu Gly Gln
260 265 270

Arg Trp Glu Thr Ser Leu Ile Met Val Lys Ser Tyr Ala Ala Met Gly
275 280 285

Gly Leu His Gly Ala Ile Asp Ala Ala Arg Arg Leu Arg Asn Ser Val
290 295 300

Ala Pro Gln Asn Ile Ser Ser Val Asp Ile Thr Val Gly Glu Thr Val
305 310 315 320

Tyr Lys His Gly Trp Trp Leu Pro Glu Arg Pro Leu Thr Pro Ile Gly
325 330 335

Ala Gln Met Asn Ile Gly Tyr Ala Thr Ala Ala Ala Leu Leu Asp Gly
340 345 350

Asn Val Leu Pro Glu Gln Phe Thr Ala Ala Arg Leu Asp Ala Asp Asp
355 360 365

Ile Trp Ala Leu Ile Ser Ala Thr Arg Val His Leu Asp Glu Ser Leu
370 375 380

```
Ala Asp Ala Asp Ile Thr Glu Lys Phe Arg Thr Asp Leu Ala Val Thr
385                 390                 395                 400

Thr Arg Glu Gly Thr Val His Arg Ala Arg Val Ala Leu Pro His Gly
                405                 410                 415

Ala Pro Asn Asp Pro Val Thr Asn Asp Glu Val Val Ala Lys Phe His
            420                 425                 430

Ala Leu Ala Asp Arg Val Thr Ser Arg Gly Arg Ala Ala Ile Glu
            435                 440                 445

Arg Ala Val Ile Arg Leu Asp Asp Leu Thr Asp Val Glu Asn Leu Met
        450                 455                 460

Asp Leu Leu Ala Asp Pro Val Ala Gly Ala Leu Asp
465                 470                 475

<210> SEQ ID NO 14
<211> LENGTH: 464
<212> TYPE: PRT
<213> ORGANISM: Salonispora tropica

<400> SEQUENCE: 14

Met Ala Gly Ala Thr Pro Thr Asp Pro Asp Gly Pro Thr Gly Arg Leu
1               5                   10                  15

Ala Thr Trp Leu Thr Glu Thr Ala Thr Asp Ala Ile Pro Ala Asp Val
            20                  25                  30

Thr Thr Arg Ala Arg His Leu Ile Leu Asp Gly Val Gly Cys Leu Leu
        35                  40                  45

Val Gly Ala Arg Leu Pro Trp Ser Arg Ile Ala Val Arg Ser Leu Thr
50                  55                  60

Val Glu Pro Gly Ser Gly Val Val Ala Gly Trp Asp Arg Thr Ala Asp
65                  70                  75                  80

Ala Ala Thr Ala Val Leu Leu Asn Ser Ser Phe Ile Gln Gly Phe Glu
                85                  90                  95

Leu Asp Asp Val Ser Tyr Gln Ile Pro Trp His Ala Asn Ala Val Leu
            100                 105                 110

Leu Pro Val Leu Leu Ala Val Ala Gly Arg Arg Gly Glu Val Thr Gly
        115                 120                 125

Ala Glu Phe Leu Arg Ala Glu Val Leu Gly Val Glu Thr Gly Ala Arg
130                 135                 140

Val Gly Leu Ala Leu Gly Gly Pro Gln Leu Val Arg Gln Gly Trp His
145                 150                 155                 160

Ser Gly Ala Val Phe Gly Gly Pro Ala Ala Ala Ala Gly Val
                165                 170                 175

Leu Leu Asp Leu Thr Pro Ala Gln Phe Glu Asp Ala Leu Gly Ile Ala
            180                 185                 190

Ala Thr Gln Ser Cys Gly Leu Met Ala Asn Glu Ala Met Val Lys Arg
        195                 200                 205

Met Gln His Gly Phe Ala Ala Arg Asn Gly Leu Val Ala Ala Met Leu
210                 215                 220

Ala Ala Gly Gly Tyr Ile Gly Thr Lys Arg Ile Phe Glu Arg Gly Tyr
225                 230                 235                 240

Gly Gly Tyr Leu Thr Val Tyr Gly Ser Gly His Asp Thr Asp Pro Ser
            245                 250                 255

Arg Ile Asp Asp Ala Leu Gly Glu His Trp Tyr Leu Arg Glu Gln Thr
        260                 265                 270

Ile Lys Pro Tyr Ala Ala Met Gly Tyr Thr His Pro Ala Ile Asp Ala
            275                 280                 285
```

```
Ala Leu Ala Leu Arg Ala Ala Asn Arg Phe Asp Pro Thr Ala Thr Glu
        290                 295                 300

Arg Ile Glu Val Glu Val Ala Glu Ser Val Phe Asp His Thr Ala Phe
305                 310                 315                 320

Pro Ile His Arg Pro Ile Glu Ser Val Ala Ala Gln Met Ser Val Arg
                325                 330                 335

Tyr Val Thr Ala Ala Ala Leu Leu Asp Gly Thr Val Ser Leu Glu Gln
            340                 345                 350

Leu Arg Pro Asp Gln Leu Asp Arg Asp Val Trp Arg Leu Val Asp
        355                 360                 365

Arg Thr Thr Val Thr Arg Gly Ser Gly Ser Ala Ser Gln Gly Arg Val
370                 375                 380

Arg Leu Thr Asp Val Asp Gly Arg Thr His Glu His His Thr Asp Ala
385                 390                 395                 400

Pro Leu Gly Ser Val Glu Arg Pro Leu Asp Asp Ala Ala Ile Val Asp
                405                 410                 415

Lys Tyr Arg Asp Leu Thr Asp Arg Ile Asp Arg Arg Gln Arg
            420                 425                 430

Thr Ile Glu Asp Leu Val Leu His Leu Asp Glu His Arg Asp Gly Pro
            435                 440                 445

Ala Ala Leu Leu Ala Leu Leu Ala Pro Ala Val Gly Asp Ala Leu Asp
450                 455                 460

<210> SEQ ID NO 15
<211> LENGTH: 490
<212> TYPE: PRT
<213> ORGANISM: Aspergillus terreus

<400> SEQUENCE: 15

Met Thr Lys Gln Ser Ala Asp Ser Asn Ala Lys Ser Gly Val Thr Ala
1               5                   10                  15

Glu Ile Cys His Trp Ala Ser Asn Leu Ala Thr Asp Asp Ile Pro Pro
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Ala Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205
```

```
Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Asn Leu Gln Arg Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ile Ala Gly Gln
            340                 345                 350

Met Ser Val Ala Tyr Ile Leu Ala Val Gln Leu Val Asp Gln Gln Cys
        355                 360                 365

Leu Leu Ala Gln Phe Ser Glu Phe Asp Asp Asn Leu Glu Arg Pro Glu
    370                 375                 380

Val Trp Asp Leu Ala Arg Lys Val Thr Pro Ser His Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Val Thr Glu Thr Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Thr Arg Val Lys Glu Ile Glu Asp Leu
    450                 455                 460

Val Leu Ser Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 16
<211> LENGTH: 449
<212> TYPE: PRT
<213> ORGANISM: Aspergillus terreus

<400> SEQUENCE: 16

Met Ala Thr Lys Ala Leu Ala Ala Trp Ala Val Ala Leu Gln Phe Thr
1               5                   10                  15

Ser Leu Pro Pro Val Thr Asp Met Ala Val Lys Ser Val Ser Asn
            20                  25                  30

Trp Ala Gly Cys Ala Ile Gly Gly Tyr Ala Leu Pro Pro Ala Gly Val
        35                  40                  45

Ala Tyr Glu Ala Val Ser Arg Leu Leu Pro His His Ala Gly Asn Val
    50                  55                  60

Ser Leu Leu Gly Thr Gly Ala Trp Thr Asp Val Gln Thr Ala Ala Leu
65                  70                  75                  80

Val Asn Gly Ile Ala Ser His Val Asp Asp Tyr Asp Asp Thr His Ala
                85                  90                  95
```

Glu Thr Pro Ile His Pro Ser Gly Pro Val Ala Ser Ala Leu Leu Ala
            100                 105                 110

Val Ala Glu Trp Ser Ala Pro Val Ser Gly Gln Asp Phe Leu Thr Ala
        115                 120                 125

Phe Val Ala Gly Val Glu Ala Glu Cys Lys Leu Gly Leu Ala Val Tyr
130                 135                 140

Pro Glu His Tyr Asp Ile Gly Trp His Ile Thr Ser Thr Thr Gly Ser
145                 150                 155                 160

Ile Gly Ala Ala Val Ala Val Gly Lys Leu Leu Gly Leu Asp Val Glu
                165                 170                 175

Gln Leu Gln Gln Ala Ile Ser Ile Ala Ala Val Gln Val Val Gly Met
            180                 185                 190

His Glu Ser Phe Gly Thr Asp Thr Lys Pro Phe His Val Gly Arg Ala
        195                 200                 205

Ala Gln Ser Gly Leu Leu Ala Ala Leu Leu Ala Gln Asn Gly Tyr Gly
210                 215                 220

Ala Ser Leu Gln Gly Leu Glu Ala Glu Arg Gly Trp Ala His Val Val
225                 230                 235                 240

Ser Thr Arg Glu Asn Leu Thr Ala Glu Phe Gly Thr Leu Gly Thr Thr
                245                 250                 255

Trp Glu Ile Ala Arg Asn Thr Phe Lys Pro Phe Pro Cys Asp Arg Ile
            260                 265                 270

Ile His Ala Ala Ile Asp Gly Trp Ile Gln Ser His Gln Leu Ala Gly
        275                 280                 285

Arg Lys Gly Leu Asp Leu Ala Gly Val Lys Asn Val Thr Ala Arg Thr
290                 295                 300

Asn Pro Arg Val Leu Phe Leu Thr Asp Asn Arg Glu Pro Arg Thr Gly
305                 310                 315                 320

Leu Asp Ala Lys Phe Ser Val Tyr His Ala Ala Val Ala Leu Leu
                325                 330                 335

Phe Gly Gln Ala Thr Pro Ala Gln Phe Thr Asp Glu Met Val Arg Asn
            340                 345                 350

Ala Thr Val Val Ala Leu Arg Asp Lys Val His Val Thr Ser Asp Glu
        355                 360                 365

Gly Val Ser Glu His Glu Ala Phe Val Ser Val Glu Phe Gln Asp Gly
370                 375                 380

Thr Gln Leu Asp Val His Val Glu His Ala Leu Gly Ser Met Glu Asn
385                 390                 395                 400

Pro Leu Ser Ala Lys Gln Leu Lys Asp Lys Phe Ile Glu His Ala Gly
                405                 410                 415

Ser Leu Ile Gly Ala Gln Arg Ala Glu Lys Ala Phe Arg Gly Phe Ser
            420                 425                 430

Ser Ile Val Asn Ser Thr Asp Val Gly Ser Ile Ser Arg Glu Phe Arg
        435                 440                 445

Lys

<210> SEQ ID NO 17
<211> LENGTH: 2256
<212> TYPE: DNA
<213> ORGANISM: Aspergillus terreus
<220> FEATURE:
<221> NAME/KEY: CDS
<222> LOCATION: (1)...(2256)

<400> SEQUENCE: 17 atg gag agt gca gag ctg tcg tcg aag cgg cag gca ttt ccc gca tgt        48

```
        Met Glu Ser Ala Glu Leu Ser Ser Lys Arg Gln Ala Phe Pro Ala Cys
        1               5                   10                  15 gat gag tgt cgg atc cgc aag gtg cga tgc agt aag gag ggt tca aag         96
Asp Glu Cys Arg Ile Arg Lys Val Arg Cys Ser Lys Glu Gly Ser Lys
                20                  25                  30 tgc tcc cat tgc ctc cga tat aac cta ccc tgc gaa ttc tcc aac aaa         144
Cys Ser His Cys Leu Arg Tyr Asn Leu Pro Cys Glu Phe Ser Asn Lys
            35                  40                  45 gtt aca cgg gtc aac caa aca gca aaa ttg gcg cga gat gtc gag aag         192
Val Thr Arg Val Asn Gln Thr Ala Lys Leu Ala Arg Asp Val Glu Lys
        50                  55                  60 ctc ggg agt cgg gtt gaa gat atc gaa cat gcc ctc caa cga tgc ctg         240
Leu Gly Ser Arg Val Glu Asp Ile Glu His Ala Leu Gln Arg Cys Leu
65                  70                  75                  80 tcc ttt att gat gcc cat cag ggc ttt cgt gat cta tca agg cca cag         288
Ser Phe Ile Asp Ala His Gln Gly Phe Arg Asp Leu Ser Arg Pro Gln
                85                  90                  95 tca caa gaa agc ggg tac aca agc tca acc agc tca gaa gag tgt gaa         336
Ser Gln Glu Ser Gly Tyr Thr Ser Ser Thr Ser Ser Glu Glu Cys Glu
            100                 105                 110 gta aac ttg tac tca ggc aaa cac act tca ccc aca gag gaa gat gga         384
Val Asn Leu Tyr Ser Gly Lys His Thr Ser Pro Thr Glu Glu Asp Gly
        115                 120                 125 ttc tgg cct ctc cac ggt tat ggc tct ttt gtt tca ctc gtt atg gag         432
Phe Trp Pro Leu His Gly Tyr Gly Ser Phe Val Ser Leu Val Met Glu
130                 135                 140 gca cag gct gct aac gcc aac cta acc tct tgg tta ccg gtc gac atg         480
Ala Gln Ala Ala Asn Ala Asn Leu Thr Ser Trp Leu Pro Val Asp Met
145                 150                 155                 160 aac agc cac caa gtc gca gag atg gtc gca ttt gac cac caa gct gtg         528
Asn Ser His Gln Val Ala Glu Met Val Ala Phe Asp His Gln Ala Val
                165                 170                 175 tca gct gtg cgc tcg aag gta act gag gca aat gaa acg ctt caa cag         576
Ser Ala Val Arg Ser Lys Val Thr Glu Ala Asn Glu Thr Leu Gln Gln
            180                 185                 190 att att gat gat atc cca acg cta tcg gca tcc gaa gac gat acc ttt         624
Ile Ile Asp Asp Ile Pro Thr Leu Ser Ala Ser Glu Asp Asp Thr Phe
        195                 200                 205 ctc ccg tct ctt cca ccc cgc gct cta gtg gag ccg tct atc aat gaa         672
Leu Pro Ser Leu Pro Pro Arg Ala Leu Val Glu Pro Ser Ile Asn Glu
210                 215                 220 tat ttc aag aag ctg aat cca cga ctc cct ata ttt agt cga cag acc         720
Tyr Phe Lys Lys Leu Asn Pro Arg Leu Pro Ile Phe Ser Arg Gln Thr
225                 230                 235                 240 att agg gac gca gtg gaa tct cag tac aca atc aga act ggg cct ccg         768
Ile Arg Asp Ala Val Glu Ser Gln Tyr Thr Ile Arg Thr Gly Pro Pro
                245                 250                 255 gac ctg gtt tgg att acc tct ttc aac tgc att gtg ctt cag gcc ctt         816
Asp Leu Val Trp Ile Thr Ser Phe Asn Cys Ile Val Leu Gln Ala Leu
            260                 265                 270 act caa aca tca att gcg aac aaa gtc gtg gga ggc aca gaa caa gac         864
Thr Gln Thr Ser Ile Ala Asn Lys Val Val Gly Gly Thr Glu Gln Asp
        275                 280                 285 ata cca tta gat tat atg atc ata agc ctg ctg cgt aac atc agg cag         912
Ile Pro Leu Asp Tyr Met Ile Ile Ser Leu Leu Arg Asn Ile Arg Gln
290                 295                 300 tgc tat aat cga ttg gaa act ctt gtt aaa ccc cgg cta tcg aat ata         960
Cys Tyr Asn Arg Leu Glu Thr Leu Val Lys Pro Arg Leu Ser Asn Ile
305                 310                 315                 320 cgg gcc ctc ttt tgt ttg gca ctt gtg gca atg gag tat ttt gat ttc        1008
```

|  |  |
|---|---|
| Arg Ala Leu Phe Cys Leu Ala Leu Val Ala Met Glu Tyr Phe Asp Phe<br>325 330 335 | |
| gca att ttt cag act atc ttt gct caa gtc tgc gag ttg tcc agg ctc<br>Ala Ile Phe Gln Thr Ile Phe Ala Gln Val Cys Glu Leu Ser Arg Leu<br>340 345 350 | 1056 |
| att gga ctc cat tta atg aca acg acc ccg cca acg gaa gat ggg gct<br>Ile Gly Leu His Leu Met Thr Thr Thr Pro Pro Thr Glu Asp Gly Ala<br>355 360 365 | 1104 |
| gtg gac gac cag cca aaa gac ttg ttc tgg agc atc ttc ctc gtc gat<br>Val Asp Asp Gln Pro Lys Asp Leu Phe Trp Ser Ile Phe Leu Val Asp<br>370 375 380 | 1152 |
| aag cac gta tcc atc att ggg ggc aag gcc tgc cta ttg ccc tcg tat<br>Lys His Val Ser Ile Ile Gly Gly Lys Ala Cys Leu Leu Pro Ser Tyr<br>385 390 395 400 | 1200 |
| gac tgc agc gta cca ttg cct cca tat gac tcc gct gcg cca ctg ccc<br>Asp Cys Ser Val Pro Leu Pro Pro Tyr Asp Ser Ala Ala Pro Leu Pro<br>405 410 415 | 1248 |
| aat gtt ttt gcg gca cgc ata cgc ttg gca ttc att ctt gag gag ata<br>Asn Val Phe Ala Ala Arg Ile Arg Leu Ala Phe Ile Leu Glu Glu Ile<br>420 425 430 | 1296 |
| tat cag tgc tta tac tca gca aaa tcc agc aaa atg gaa cag agt cgc<br>Tyr Gln Cys Leu Tyr Ser Ala Lys Ser Ser Lys Met Glu Gln Ser Arg<br>435 440 445 | 1344 |
| gtc cgc cgc cgt atc cgc aga att gct cga aaa ctt agc cag tgg cac<br>Val Arg Arg Arg Ile Arg Arg Ile Ala Arg Lys Leu Ser Gln Trp His<br>450 455 460 | 1392 |
| gtg caa cat gag cat gta ctg cgt acc gga gat tcg aaa agg cct ctc<br>Val Gln His Glu His Val Leu Arg Thr Gly Asp Ser Lys Arg Pro Leu<br>465 470 475 480 | 1440 |
| gaa gag tat atc tgt gca atg cag ttg aga ttt gca ctc tcg agc tgt<br>Glu Glu Tyr Ile Cys Ala Met Gln Leu Arg Phe Ala Leu Ser Ser Cys<br>485 490 495 | 1488 |
| tgg gta ctt ctg cat aaa cgc att tgg agc cag gaa agg ggc aca gtc<br>Trp Val Leu Leu His Lys Arg Ile Trp Ser Gln Glu Arg Gly Thr Val<br>500 505 510 | 1536 |
| tgc cta caa cac gct cgg gat tgt ctg atg ctg ttc aag caa tta tgc<br>Cys Leu Gln His Ala Arg Asp Cys Leu Met Leu Phe Lys Gln Leu Cys<br>515 520 525 | 1584 |
| gat ggg tgt aaa tct ggc ttc agc aat ttc gac agc att gtc ctg aac<br>Asp Gly Cys Lys Ser Gly Phe Ser Asn Phe Asp Ser Ile Val Leu Asn<br>530 535 540 | 1632 |
| tat tct ttg atc tca ttc atg gga atc tat gtc cac att gtg gag gaa<br>Tyr Ser Leu Ile Ser Phe Met Gly Ile Tyr Val His Ile Val Glu Glu<br>545 550 555 560 | 1680 |
| gac cag ccg atc cat tca cag gac atg gag ata ctc act ttc ttc gct<br>Asp Gln Pro Ile His Ser Gln Asp Met Glu Ile Leu Thr Phe Phe Ala<br>565 570 575 | 1728 |
| ata tac acg aac cgc ttg gca tcc aat agg tca gct gca tct atc ccg<br>Ile Tyr Thr Asn Arg Leu Ala Ser Asn Arg Ser Ala Ala Ser Ile Pro<br>580 585 590 | 1776 |
| tac aaa ttc agc caa gtg gcc agt cgc tgt agc gat att gcc ctc ctc<br>Tyr Lys Phe Ser Gln Val Ala Ser Arg Cys Ser Asp Ile Ala Leu Leu<br>595 600 605 | 1824 |
| ctc cag aac tta agg gag agg cgt ttt att ccg aca acg ata tca cga<br>Leu Gln Asn Leu Arg Glu Arg Arg Phe Ile Pro Thr Thr Ile Ser Arg<br>610 615 620 | 1872 |
| agt cca acg ccc tca tgg aac gag cca acc tac atg gat tac gat gcc<br>Ser Pro Thr Pro Ser Trp Asn Glu Pro Thr Tyr Met Asp Tyr Asp Ala<br>625 630 635 640 | 1920 |
| gcc aat gcg tcc act agc aca act agc acc ggc tct tca tat aac ttg | 1968 |

```
                 Ala Asn Ala Ser Thr Ser Thr Thr Ser Thr Gly Ser Ser Tyr Asn Leu
                                 645                 650                 655 aat atc ggc cct ctt ggc gta cct gga gac ggc cag gtc tgg gac ata             2016
Asn Ile Gly Pro Leu Gly Val Pro Gly Asp Gly Gln Val Trp Asp Ile
            660                 665                 670 tac ttc aac ccg aga gag ata cca atg gat ggt aca att gcg act cct             2064
Tyr Phe Asn Pro Arg Glu Ile Pro Met Asp Gly Thr Ile Ala Thr Pro
            675                 680                 685 tct gag gat gca acc cag gat ttg ctg agc aat gag gct ggc caa tgc             2112
Ser Glu Asp Ala Thr Gln Asp Leu Leu Ser Asn Glu Ala Gly Gln Cys
            690                 695                 700 ctt gac ttc ccc gac ttt tca ctt ggc att gac aac ttc cct gac ttt             2160
Leu Asp Phe Pro Asp Phe Ser Leu Gly Ile Asp Asn Phe Pro Asp Phe
705                 710                 715                 720 cca ctt ggc att gac atg act agc caa agc gaa ttt gat ctt att atg             2208
Pro Leu Gly Ile Asp Met Thr Ser Gln Ser Glu Phe Asp Leu Ile Met
                725                 730                 735 gag gag gac ata att cga tat aag aga cta cta gat agg cct gtt tag             2256
Glu Glu Asp Ile Ile Arg Tyr Lys Arg Leu Leu Asp Arg Pro Val
                740                 745                 750

<210> SEQ ID NO 18
<211> LENGTH: 751
<212> TYPE: PRT
<213> ORGANISM: Aspergillus terreus

<400> SEQUENCE: 18

Met Glu Ser Ala Glu Leu Ser Ser Lys Arg Gln Ala Phe Pro Ala Cys
1               5                   10                  15

Asp Glu Cys Arg Ile Arg Lys Val Arg Cys Ser Lys Glu Gly Ser Lys
            20                  25                  30

Cys Ser His Cys Leu Arg Tyr Asn Leu Pro Cys Glu Phe Ser Asn Lys
        35                  40                  45

Val Thr Arg Val Asn Gln Thr Ala Lys Leu Ala Arg Asp Val Glu Lys
    50                  55                  60

Leu Gly Ser Arg Val Glu Asp Ile Glu His Ala Leu Gln Arg Cys Leu
65                  70                  75                  80

Ser Phe Ile Asp Ala His Gln Gly Phe Arg Asp Leu Ser Arg Pro Gln
                85                  90                  95

Ser Gln Glu Ser Gly Tyr Thr Ser Ser Thr Ser Ser Glu Glu Cys Glu
            100                 105                 110

Val Asn Leu Tyr Ser Gly Lys His Thr Ser Pro Thr Glu Glu Asp Gly
        115                 120                 125

Phe Trp Pro Leu His Gly Tyr Gly Ser Phe Val Ser Leu Val Met Glu
    130                 135                 140

Ala Gln Ala Ala Asn Ala Asn Leu Thr Ser Trp Leu Pro Val Asp Met
145                 150                 155                 160

Asn Ser His Gln Val Ala Glu Met Val Ala Phe Asp His Gln Ala Val
                165                 170                 175

Ser Ala Val Arg Ser Lys Val Thr Glu Ala Asn Glu Thr Leu Gln Gln
            180                 185                 190

Ile Ile Asp Asp Ile Pro Thr Leu Ser Ala Ser Glu Asp Asp Thr Phe
        195                 200                 205

Leu Pro Ser Leu Pro Pro Arg Ala Leu Val Glu Pro Ser Ile Asn Glu
    210                 215                 220

Tyr Phe Lys Lys Leu Asn Pro Arg Leu Pro Ile Phe Ser Arg Gln Thr
225                 230                 235                 240
```

-continued

```
Ile Arg Asp Ala Val Glu Ser Gln Tyr Thr Ile Arg Thr Gly Pro Pro
                245                 250                 255

Asp Leu Val Trp Ile Thr Ser Phe Asn Cys Ile Val Leu Gln Ala Leu
            260                 265                 270

Thr Gln Thr Ser Ile Ala Asn Lys Val Val Gly Gly Thr Glu Gln Asp
        275                 280                 285

Ile Pro Leu Asp Tyr Met Ile Ile Ser Leu Leu Arg Asn Ile Arg Gln
    290                 295                 300

Cys Tyr Asn Arg Leu Glu Thr Leu Val Lys Pro Arg Leu Ser Asn Ile
305                 310                 315                 320

Arg Ala Leu Phe Cys Leu Ala Leu Val Ala Met Glu Tyr Phe Asp Phe
                325                 330                 335

Ala Ile Phe Gln Thr Ile Phe Ala Gln Val Cys Glu Leu Ser Arg Leu
            340                 345                 350

Ile Gly Leu His Leu Met Thr Thr Thr Pro Pro Thr Glu Asp Gly Ala
        355                 360                 365

Val Asp Asp Gln Pro Lys Asp Leu Phe Trp Ser Ile Phe Leu Val Asp
    370                 375                 380

Lys His Val Ser Ile Ile Gly Lys Ala Cys Leu Leu Pro Ser Tyr
385                 390                 395                 400

Asp Cys Ser Val Pro Leu Pro Pro Tyr Asp Ser Ala Ala Pro Leu Pro
                405                 410                 415

Asn Val Phe Ala Ala Arg Ile Arg Leu Ala Phe Ile Leu Glu Glu Ile
            420                 425                 430

Tyr Gln Cys Leu Tyr Ser Ala Lys Ser Ser Lys Met Glu Gln Ser Arg
        435                 440                 445

Val Arg Arg Arg Ile Arg Arg Ile Ala Arg Lys Leu Ser Gln Trp His
    450                 455                 460

Val Gln His Glu His Val Leu Arg Thr Gly Asp Ser Lys Arg Pro Leu
465                 470                 475                 480

Glu Glu Tyr Ile Cys Ala Met Gln Leu Arg Phe Ala Leu Ser Ser Cys
                485                 490                 495

Trp Val Leu Leu His Lys Arg Ile Trp Ser Gln Glu Arg Gly Thr Val
            500                 505                 510

Cys Leu Gln His Ala Arg Asp Cys Leu Met Leu Phe Lys Gln Leu Cys
        515                 520                 525

Asp Gly Cys Lys Ser Gly Phe Ser Asn Phe Asp Ser Ile Val Leu Asn
    530                 535                 540

Tyr Ser Leu Ile Ser Phe Met Gly Ile Tyr Val His Ile Val Glu Glu
545                 550                 555                 560

Asp Gln Pro Ile His Ser Gln Asp Met Glu Ile Leu Thr Phe Phe Ala
                565                 570                 575

Ile Tyr Thr Asn Arg Leu Ala Ser Asn Arg Ser Ala Ala Ser Ile Pro
            580                 585                 590

Tyr Lys Phe Ser Gln Val Ala Ser Arg Cys Ser Asp Ile Ala Leu Leu
        595                 600                 605

Leu Gln Asn Leu Arg Glu Arg Arg Phe Ile Pro Thr Thr Ile Ser Arg
    610                 615                 620

Ser Pro Thr Pro Ser Trp Asn Glu Pro Thr Tyr Met Asp Tyr Asp Ala
625                 630                 635                 640

Ala Asn Ala Ser Thr Ser Thr Thr Ser Thr Gly Ser Ser Tyr Asn Leu
                645                 650                 655

Asn Ile Gly Pro Leu Gly Val Pro Gly Asp Gly Gln Val Trp Asp Ile
            660                 665                 670
```

```
Tyr Phe Asn Pro Arg Glu Ile Pro Met Asp Gly Thr Ile Ala Thr Pro
            675                 680                 685

Ser Glu Asp Ala Thr Gln Asp Leu Leu Ser Asn Glu Ala Gly Gln Cys
        690                 695                 700

Leu Asp Phe Pro Asp Phe Ser Leu Gly Ile Asp Asn Phe Pro Asp Phe
705                 710                 715                 720

Pro Leu Gly Ile Asp Met Thr Ser Gln Ser Glu Phe Asp Leu Ile Met
                725                 730                 735

Glu Glu Asp Ile Ile Arg Tyr Lys Arg Leu Leu Asp Arg Pro Val
            740                 745                 750

<210> SEQ ID NO 19
<211> LENGTH: 906
<212> TYPE: DNA
<213> ORGANISM: Aspergillus terreus
<220> FEATURE:
<221> NAME/KEY: CDS
<222> LOCATION: (1)...(906)

<400> SEQUENCE: 19 atg gac tct aaa atc cag aca aat gtt cca tta cca aag gca ccc ctt        48
Met Asp Ser Lys Ile Gln Thr Asn Val Pro Leu Pro Lys Ala Pro Leu
 1               5                  10                  15 atc caa aaa gcc cgt ggg aag cgt acg aaa ggc att cct gca ttg gtt        96
Ile Gln Lys Ala Arg Gly Lys Arg Thr Lys Gly Ile Pro Ala Leu Val
                20                  25                  30 gcg ggt gct tgt gct ggg gca gtt gaa atc tcc atc acc tac cct ttc       144
Ala Gly Ala Cys Ala Gly Ala Val Glu Ile Ser Ile Thr Tyr Pro Phe
            35                  40                  45 gaa tcg gct aaa act cgc gcc cag ctt aag cgg cga aac cat gat gtg       192
Glu Ser Ala Lys Thr Arg Ala Gln Leu Lys Arg Arg Asn His Asp Val
        50                  55                  60 gca gct ata aaa cct gga atc cga ggc tgg tat gct ggg tat gga gcc       240
Ala Ala Ile Lys Pro Gly Ile Arg Gly Trp Tyr Ala Gly Tyr Gly Ala
65                  70                  75                  80 acc ttg gta gga acc aca gtg aaa gcc tcc gtt caa ttt gcc tca ttc       288
Thr Leu Val Gly Thr Thr Val Lys Ala Ser Val Gln Phe Ala Ser Phe
                85                  90                  95 aat att tat cgc tcg gcc ctt tcg ggc cca aat gga gag ctc tca act       336
Asn Ile Tyr Arg Ser Ala Leu Ser Gly Pro Asn Gly Glu Leu Ser Thr
            100                 105                 110 gga gct tcc gtc ctg gct ggg ttt ggg gct ggc gtg acc gag gct gtc       384
Gly Ala Ser Val Leu Ala Gly Phe Gly Ala Gly Val Thr Glu Ala Val
        115                 120                 125 tta gcc gta acc cca gcg gag gcg atc aag aca aaa atc att gat gca       432
Leu Ala Val Thr Pro Ala Glu Ala Ile Lys Thr Lys Ile Ile Asp Ala
    130                 135                 140 agg aag gtt gga aat gca gag tta agt acg act ttt ggc gcg ata gct       480
Arg Lys Val Gly Asn Ala Glu Leu Ser Thr Thr Phe Gly Ala Ile Ala
145                 150                 155                 160 ggg atc ctt cga gat cgg gga ccg ctt gga ttc ttc tct gcg gtt ggt       528
Gly Ile Leu Arg Asp Arg Gly Pro Leu Gly Phe Phe Ser Ala Val Gly
                165                 170                 175 cct aca att ttg cgg cag tcc tcc aat gcg gca gtg aag ttc act gtt       576
Pro Thr Ile Leu Arg Gln Ser Ser Asn Ala Ala Val Lys Phe Thr Val
            180                 185                 190 tat aac gaa ctt att ggg ctg gcc cga aaa tac tcg aag aat ggc gaa       624
Tyr Asn Glu Leu Ile Gly Leu Ala Arg Lys Tyr Ser Lys Asn Gly Glu
        195                 200                 205 gac gtg cac cct ctg gca agc acc ttg gtc ggt tct gtt act gga gtt       672
Asp Val His Pro Leu Ala Ser Thr Leu Val Gly Ser Val Thr Gly Val
```

```
Asp Val His Pro Leu Ala Ser Thr Leu Val Gly Ser Val Thr Gly Val
    210                 215                 220 tgc tgc gcc tgg tcg aca cag cca ctg gac gtg atc aag aca cga atg       720
Cys Cys Ala Trp Ser Thr Gln Pro Leu Asp Val Ile Lys Thr Arg Met
225                 230                 235                 240 caa tct ctt cag gca aga caa ctg tac gga aat acc ttc aac tgc gtg       768
Gln Ser Leu Gln Ala Arg Gln Leu Tyr Gly Asn Thr Phe Asn Cys Val
                    245                 250                 255 aaa aca ctc ctg cgc agt gaa ggc att ggc gtt ttc tgg tcc ggt gtc       816
Lys Thr Leu Leu Arg Ser Glu Gly Ile Gly Val Phe Trp Ser Gly Val
                260                 265                 270 tgg ttt cgg aca ggg aga ctt tcc ctt acc tcg gcc atc atg ttt ccc       864
Trp Phe Arg Thr Gly Arg Leu Ser Leu Thr Ser Ala Ile Met Phe Pro
            275                 280                 285 gtc tac gag aaa gtc tac aag ttc ttg acg caa cca aac tga               906
Val Tyr Glu Lys Val Tyr Lys Phe Leu Thr Gln Pro Asn
        290                 295                 300

<210> SEQ ID NO 20
<211> LENGTH: 301
<212> TYPE: PRT
<213> ORGANISM: Aspergillus terreus

<400> SEQUENCE: 20

Met Asp Ser Lys Ile Gln Thr Asn Val Pro Leu Pro Lys Ala Pro Leu
1               5                   10                  15

Ile Gln Lys Ala Arg Gly Lys Arg Thr Lys Gly Ile Pro Ala Leu Val
            20                  25                  30

Ala Gly Ala Cys Ala Gly Ala Val Glu Ile Ser Ile Thr Tyr Pro Phe
        35                  40                  45

Glu Ser Ala Lys Thr Arg Ala Gln Leu Lys Arg Arg Asn His Asp Val
    50                  55                  60

Ala Ala Ile Lys Pro Gly Ile Arg Gly Trp Tyr Ala Gly Tyr Gly Ala
65                  70                  75                  80

Thr Leu Val Gly Thr Thr Val Lys Ala Ser Val Gln Phe Ala Ser Phe
                85                  90                  95

Asn Ile Tyr Arg Ser Ala Leu Ser Gly Pro Asn Gly Glu Leu Ser Thr
            100                 105                 110

Gly Ala Ser Val Leu Ala Gly Phe Gly Ala Gly Val Thr Glu Ala Val
        115                 120                 125

Leu Ala Val Thr Pro Ala Glu Ala Ile Lys Thr Lys Ile Ile Asp Ala
    130                 135                 140

Arg Lys Val Gly Asn Ala Glu Leu Ser Thr Thr Phe Gly Ala Ile Ala
145                 150                 155                 160

Gly Ile Leu Arg Asp Arg Gly Pro Leu Gly Phe Phe Ser Ala Val Gly
                165                 170                 175

Pro Thr Ile Leu Arg Gln Ser Ser Asn Ala Ala Val Lys Phe Thr Val
            180                 185                 190

Tyr Asn Glu Leu Ile Gly Leu Ala Arg Lys Tyr Ser Lys Asn Gly Glu
        195                 200                 205

Asp Val His Pro Leu Ala Ser Thr Leu Val Gly Ser Val Thr Gly Val
    210                 215                 220

Cys Cys Ala Trp Ser Thr Gln Pro Leu Asp Val Ile Lys Thr Arg Met
225                 230                 235                 240

Gln Ser Leu Gln Ala Arg Gln Leu Tyr Gly Asn Thr Phe Asn Cys Val
                245                 250                 255

Lys Thr Leu Leu Arg Ser Glu Gly Ile Gly Val Phe Trp Ser Gly Val
```

```
                   260                 265                 270
Trp Phe Arg Thr Gly Arg Leu Ser Leu Thr Ser Ala Ile Met Phe Pro
        275                 280                 285

Val Tyr Glu Lys Val Tyr Lys Phe Leu Thr Gln Pro Asn
        290                 295                 300

<210> SEQ ID NO 21
<211> LENGTH: 1212
<212> TYPE: DNA
<213> ORGANISM: Aspergillus terreus
<220> FEATURE:
<221> NAME/KEY: CDS
<222> LOCATION: (1)...(1212)

<400> SEQUENCE: 21 atg ggc cac ggt gac act gag tcc ccg aac cca acg acg acc acg gaa      48
Met Gly His Gly Asp Thr Glu Ser Pro Asn Pro Thr Thr Thr Thr Glu
 1               5                  10                  15 ggt agc gga caa aac gag cca gag aaa aag ggc cgt gat att cca tta      96
Gly Ser Gly Gln Asn Glu Pro Glu Lys Lys Gly Arg Asp Ile Pro Leu
             20                  25                  30 tgg aga aaa tgt gtc att acg ttt gtt gtt agt tgg atg act cta gtc     144
Trp Arg Lys Cys Val Ile Thr Phe Val Val Ser Trp Met Thr Leu Val
         35                  40                  45 gtt act ttc tcc agt act tgt ctt ctt cct gcc gcc cct gaa atc gcg     192
Val Thr Phe Ser Ser Thr Cys Leu Leu Pro Ala Ala Pro Glu Ile Ala
     50                  55                  60 aat gaa ttt gat atg act gtc gag act atc aac atc tcc aat gct ggt     240
Asn Glu Phe Asp Met Thr Val Glu Thr Ile Asn Ile Ser Asn Ala Gly
 65                  70                  75                  80 gtc cta gtt gcc atg gga tat tca tcc ctc ata tgg ggt ccc atg aac     288
Val Leu Val Ala Met Gly Tyr Ser Ser Leu Ile Trp Gly Pro Met Asn
                 85                  90                  95 aag tta gtc ggc cgg cgg aca tca tac aat ctg gcc att tca atg ctt     336
Lys Leu Val Gly Arg Arg Thr Ser Tyr Asn Leu Ala Ile Ser Met Leu
            100                 105                 110 tgt gca tgc tcc gct gga acg gca gcg gcg ata aac gag gaa atg ttc     384
Cys Ala Cys Ser Ala Gly Thr Ala Ala Ala Ile Asn Glu Glu Met Phe
        115                 120                 125 ata gcg ttc aga gtg ttg agc ggc tta acc gga acc tcg ttc atg gtc     432
Ile Ala Phe Arg Val Leu Ser Gly Leu Thr Gly Thr Ser Phe Met Val
    130                 135                 140 tca ggc caa act gtt ctt gca gat atc ttt gag cct gtt tac cgt ggg     480
Ser Gly Gln Thr Val Leu Ala Asp Ile Phe Glu Pro Val Tyr Arg Gly
145                 150                 155                 160 acg gcc gta ggt ttc ttc atg gcc ggg act ctt tct ggc cct gca ata     528
Thr Ala Val Gly Phe Phe Met Ala Gly Thr Leu Ser Gly Pro Ala Ile
                165                 170                 175 ggc ccc tgc gtg gga ggg gtc atc gtc act ttc acg agt tgg cgt gtt     576
Gly Pro Cys Val Gly Gly Val Ile Val Thr Phe Thr Ser Trp Arg Val
            180                 185                 190 atc ttc tgg ctt caa cta ggt atg agc ggg ctg ggg ctc gtg ctt tct     624
Ile Phe Trp Leu Gln Leu Gly Met Ser Gly Leu Gly Leu Val Leu Ser
        195                 200                 205 ctg cta ttt ttc ccg aaa atc gaa gga aat tct gag aag gtc tca acg     672
Leu Leu Phe Phe Pro Lys Ile Glu Gly Asn Ser Glu Lys Val Ser Thr
    210                 215                 220 gcg ttt aaa ccg acc aca ctt gtc aca atc ata tcg aaa ttc tcc cca     720
Ala Phe Lys Pro Thr Thr Leu Val Thr Ile Ile Ser Lys Phe Ser Pro
225                 230                 235                 240 acg gat gtg ctc aag cag tgg gtg tat cca aat gtc ttt ctt gcc gac     768
Thr Asp Val Leu Lys Gln Trp Val Tyr Pro Asn Val Phe Leu Ala Asp
```

```
Thr Asp Val Leu Lys Gln Trp Val Tyr Pro Asn Val Phe Leu Ala Asp
                245                 250                 255 tta tgc tgt ggc ctc ctg gca atc acg caa tat tcg atc ctg act tca         816
Leu Cys Cys Gly Leu Leu Ala Ile Thr Gln Tyr Ser Ile Leu Thr Ser
            260                 265                 270 gct cgt gcc ata ttc aac tca cga ttt cat tta acg act gcc cta gta         864
Ala Arg Ala Ile Phe Asn Ser Arg Phe His Leu Thr Thr Ala Leu Val
        275                 280                 285 tcg ggt ctc ttc tac ctc gct cca ggt gcc ggg ttc ctg ata ggc agt         912
Ser Gly Leu Phe Tyr Leu Ala Pro Gly Ala Gly Phe Leu Ile Gly Ser
    290                 295                 300 ctc gtc ggc ggt aaa ctt tcg gat cgc acc gtt cgg aga tac ata gta         960
Leu Val Gly Gly Lys Leu Ser Asp Arg Thr Val Arg Arg Tyr Ile Val
305                 310                 315                 320 aag cgc gga ttc cgt ctc cct cag gat cga ctc cac agc ggg ctc atc        1008
Lys Arg Gly Phe Arg Leu Pro Gln Asp Arg Leu His Ser Gly Leu Ile
                325                 330                 335 aca ttg ttc gcc gtg ctg ccc gca gga acg ctc att tac ggg tgg aca        1056
Thr Leu Phe Ala Val Leu Pro Ala Gly Thr Leu Ile Tyr Gly Trp Thr
            340                 345                 350 ctc caa gag gat aag ggt gat atg gta gtg ccc ata atc gcg gcg ttc        1104
Leu Gln Glu Asp Lys Gly Asp Met Val Val Pro Ile Ile Ala Ala Phe
        355                 360                 365 ttc gcg ggc tgg ggg ctc atg ggc agt ttt aac tgc ctg aac act tac        1152
Phe Ala Gly Trp Gly Leu Met Gly Ser Phe Asn Cys Leu Asn Thr Tyr
    370                 375                 380 gtg gct ggt ttg ttc cac acc ctc att tat cta ttc cct ttg tgt aca        1200
Val Ala Gly Leu Phe His Thr Leu Ile Tyr Leu Phe Pro Leu Cys Thr
385                 390                 395                 400 tgc cca caa taa                                                        1212
Cys Pro Gln <210> SEQ ID NO 22
<211> LENGTH: 403
<212> TYPE: PRT
<213> ORGANISM: Aspergillus terreus

<400> SEQUENCE: 22

Met Gly His Gly Asp Thr Glu Ser Pro Asn Pro Thr Thr Thr Glu
1               5                   10                  15

Gly Ser Gly Gln Asn Glu Pro Glu Lys Lys Gly Arg Asp Ile Pro Leu
            20                  25                  30

Trp Arg Lys Cys Val Ile Thr Phe Val Val Ser Trp Met Thr Leu Val
        35                  40                  45

Val Thr Phe Ser Ser Thr Cys Leu Leu Pro Ala Ala Pro Glu Ile Ala
    50                  55                  60

Asn Glu Phe Asp Met Thr Val Glu Thr Ile Asn Ile Ser Asn Ala Gly
65                  70                  75                  80

Val Leu Val Ala Met Gly Tyr Ser Ser Leu Ile Trp Gly Pro Met Asn
                85                  90                  95

Lys Leu Val Gly Arg Arg Thr Ser Tyr Asn Leu Ala Ile Ser Met Leu
            100                 105                 110

Cys Ala Cys Ser Ala Gly Thr Ala Ala Ala Ile Asn Glu Glu Met Phe
        115                 120                 125

Ile Ala Phe Arg Val Leu Ser Gly Leu Thr Gly Thr Ser Phe Met Val
    130                 135                 140

Ser Gly Gln Thr Val Leu Ala Asp Ile Phe Glu Pro Val Tyr Arg Gly
145                 150                 155                 160
```

```
Thr Ala Val Gly Phe Phe Met Ala Gly Thr Leu Ser Gly Pro Ala Ile
                165                 170                 175

Gly Pro Cys Val Gly Val Ile Val Thr Phe Thr Ser Trp Arg Val
            180                 185                 190

Ile Phe Trp Leu Gln Leu Gly Met Ser Gly Leu Gly Leu Val Leu Ser
                195                 200                 205

Leu Leu Phe Phe Pro Lys Ile Glu Gly Asn Ser Glu Lys Val Ser Thr
    210                 215                 220

Ala Phe Lys Pro Thr Thr Leu Val Thr Ile Ile Ser Lys Phe Ser Pro
225                 230                 235                 240

Thr Asp Val Leu Lys Gln Trp Val Tyr Pro Asn Val Phe Leu Ala Asp
                245                 250                 255

Leu Cys Cys Gly Leu Leu Ala Ile Thr Gln Tyr Ser Ile Leu Thr Ser
            260                 265                 270

Ala Arg Ala Ile Phe Asn Ser Arg Phe His Leu Thr Thr Ala Leu Val
        275                 280                 285

Ser Gly Leu Phe Tyr Leu Ala Pro Gly Ala Gly Phe Leu Ile Gly Ser
    290                 295                 300

Leu Val Gly Gly Lys Leu Ser Asp Arg Thr Val Arg Arg Tyr Ile Val
305                 310                 315                 320

Lys Arg Gly Phe Arg Leu Pro Gln Asp Arg Leu His Ser Gly Leu Ile
                325                 330                 335

Thr Leu Phe Ala Val Leu Pro Ala Gly Thr Leu Ile Tyr Gly Trp Thr
            340                 345                 350

Leu Gln Glu Asp Lys Gly Asp Met Val Val Pro Ile Ile Ala Ala Phe
        355                 360                 365

Phe Ala Gly Trp Gly Leu Met Gly Ser Phe Asn Cys Leu Asn Thr Tyr
    370                 375                 380

Val Ala Gly Leu Phe His Thr Leu Ile Tyr Leu Phe Pro Leu Cys Thr
385                 390                 395                 400

Cys Pro Gln

<210> SEQ ID NO 23
<211> LENGTH: 1473
<212> TYPE: DNA
<213> ORGANISM: Aspergillus terreus
<220> FEATURE:
<221> NAME/KEY: CDS
<222> LOCATION: (1)...(1473)

<400> SEQUENCE: 23 atg acc aag caa tct gcg gac agc aac gca aag tca gga gtt acg gcc      48
Met Thr Lys Gln Ser Ala Asp Ser Asn Ala Lys Ser Gly Val Thr Ala
1               5                   10                  15 gaa ata tgc cat tgg gca tcc aac ctg gcc act gac gac atc cct tcg      96
Glu Ile Cys His Trp Ala Ser Asn Leu Ala Thr Asp Asp Ile Pro Ser
                20                  25                  30 gac gta tta gaa aga gcg aaa tac ctg att ctc gat ggt att gca tgt     144
Asp Val Leu Glu Arg Ala Lys Tyr Leu Ile Leu Asp Gly Ile Ala Cys
            35                  40                  45 gcc tgg gtt ggt gca aga gtg cct tgg tca gag aag tat gtg cag gca     192
Ala Trp Val Gly Ala Arg Val Pro Trp Ser Glu Lys Tyr Val Gln Ala
        50                  55                  60 aca atg agc ttt gag ccg cca gga gcc tgc agg gtg att gga tat ggg     240
Thr Met Ser Phe Glu Pro Pro Gly Ala Cys Arg Val Ile Gly Tyr Gly
65                  70                  75                  80 cag aaa ctg ggg cct gtt gca gca gcc atg acc aat tcc gct ttc ata     288
Gln Lys Leu Gly Pro Val Ala Ala Ala Met Thr Asn Ser Ala Phe Ile
```

-continued

```
                      85                  90                  95
cag gcc aca gag ctt gac gac tac cac agc gaa gcc ccc cta cac tct        336
Gln Ala Thr Glu Leu Asp Asp Tyr His Ser Glu Ala Pro Leu His Ser
            100                 105                 110 gca agc atc gtc ctc cct gcg gtc ttt gca gca agt gag gtc tta gcc        384
Ala Ser Ile Val Leu Pro Ala Val Phe Ala Ala Ser Glu Val Leu Ala
        115                 120                 125 gag caa ggc aaa aca att tct ggt ata gat gtc att cta gcc gcc att        432
Glu Gln Gly Lys Thr Ile Ser Gly Ile Asp Val Ile Leu Ala Ala Ile
130                 135                 140 gtg ggg ttt gaa tct ggc ccg cgg atc ggc aaa gca att tac gga tcg        480
Val Gly Phe Glu Ser Gly Pro Arg Ile Gly Lys Ala Ile Tyr Gly Ser
145                 150                 155                 160 gac ctc ttg aac aac ggc tgg cat tgt gga gcc gtg tat ggt gct cca        528
Asp Leu Leu Asn Asn Gly Trp His Cys Gly Ala Val Tyr Gly Ala Pro
                165                 170                 175 gct ggt gcg ctg gcc aca gga aag ctc ctc ggt cta act cca gac tcc        576
Ala Gly Ala Leu Ala Thr Gly Lys Leu Leu Gly Leu Thr Pro Asp Ser
            180                 185                 190 atg gaa gat gct ctc gga atc gcg tgc acg caa gcc tgt ggt tta atg        624
Met Glu Asp Ala Leu Gly Ile Ala Cys Thr Gln Ala Cys Gly Leu Met
        195                 200                 205 tcg gcg caa tac gga ggc atg gtc aag cgc gtg caa cat gga ttc gca        672
Ser Ala Gln Tyr Gly Gly Met Val Lys Arg Val Gln His Gly Phe Ala
210                 215                 220 gcg cgt aat ggt ctt ctt ggg gga ctg ttg gcc tat ggt ggg tac gag        720
Ala Arg Asn Gly Leu Leu Gly Gly Leu Leu Ala Tyr Gly Gly Tyr Glu
225                 230                 235                 240 gcc atg aag ggt gtc ctg gag aga tct tat ggc ggt ttc ctc aaa atg        768
Ala Met Lys Gly Val Leu Glu Arg Ser Tyr Gly Gly Phe Leu Lys Met
                245                 250                 255 ttc acc aag ggc aat ggc aga gag cct ccc tac aaa gag gag gaa gtg        816
Phe Thr Lys Gly Asn Gly Arg Glu Pro Pro Tyr Lys Glu Glu Glu Val
            260                 265                 270 gtg gcc ggt ctc ggt tca ttc tgg cat acc ttt act att cgc atc aag        864
Val Ala Gly Leu Gly Ser Phe Trp His Thr Phe Thr Ile Arg Ile Lys
        275                 280                 285 ctc tat gcc tgc tgc gga ctt gtc cat ggt cca gtc gaa gct atc gaa        912
Leu Tyr Ala Cys Cys Gly Leu Val His Gly Pro Val Glu Ala Ile Glu
290                 295                 300 aag ctt cag agg aga tac ccc gag ctc ttg aat aga gcc aac ctc agc        960
Lys Leu Gln Arg Arg Tyr Pro Glu Leu Leu Asn Arg Ala Asn Leu Ser
305                 310                 315                 320 aac att cgc cat gtt tat gta cag ctt tca aca gcc tcg aac agt cac       1008
Asn Ile Arg His Val Tyr Val Gln Leu Ser Thr Ala Ser Asn Ser His
                325                 330                 335 tgt gga tgg ata cca gag gag agg ccc atc agt tca atc gca ggg cag       1056
Cys Gly Trp Ile Pro Glu Glu Arg Pro Ile Ser Ser Ile Ala Gly Gln
            340                 345                 350 atg agt gtc gca tac atc ctc gcc gtc cag ctg gtc gac cag caa tgt       1104
Met Ser Val Ala Tyr Ile Leu Ala Val Gln Leu Val Asp Gln Gln Cys
        355                 360                 365 ctt ctg gct cag ttt tct gag ttt gat gac aac ttg gag aga cca gaa       1152
Leu Leu Ala Gln Phe Ser Glu Phe Asp Asp Asn Leu Glu Arg Pro Glu
370                 375                 380 gtg tgg gat ctg gcc agg aag gtt act cca tct cat agc gaa gag ttt       1200
Val Trp Asp Leu Ala Arg Lys Val Thr Pro Ser His Ser Glu Glu Phe
385                 390                 395                 400 gat caa gac ggc aac tgt ctc agt gcg ggt cgc gtg agg att gag ttc       1248
Asp Gln Asp Gly Asn Cys Leu Ser Ala Gly Arg Val Arg Ile Glu Phe
```

```
                         405                 410                 415
aac gat ggc tct tct gtt acg gaa act gtc gag aag cct ctt gga gtc    1296
Asn Asp Gly Ser Ser Val Thr Glu Thr Val Glu Lys Pro Leu Gly Val
            420                 425                 430 aaa gag ccc atg cca aac gaa cgg att ctc cac aaa tac cga acc ctt    1344
Lys Glu Pro Met Pro Asn Glu Arg Ile Leu His Lys Tyr Arg Thr Leu
        435                 440                 445 gcg ggt agc gtg acg gac gaa tcc cgg gtg aaa gag att gag gat ctt    1392
Ala Gly Ser Val Thr Asp Glu Ser Arg Val Lys Glu Ile Glu Asp Leu
450                 455                 460 gtc ctc agc ctg gac agg ctc acc gac att acc cca ttg ctg gag ctg    1440
Val Leu Ser Leu Asp Arg Leu Thr Asp Ile Thr Pro Leu Leu Glu Leu
465                 470                 475                 480 ctt aat tgt ccc gtg aaa tcg cca ctg gta taa                        1473
Leu Asn Cys Pro Val Lys Ser Pro Leu Val
                485                 490

<210> SEQ ID NO 24
<211> LENGTH: 490
<212> TYPE: PRT
<213> ORGANISM: Aspergillus terreus

<400> SEQUENCE: 24

Met Thr Lys Gln Ser Ala Asp Ser Asn Ala Lys Ser Gly Val Thr Ala
 1               5                   10                  15

Glu Ile Cys His Trp Ala Ser Asn Leu Ala Thr Asp Asp Ile Pro Ser
             20                  25                  30

Asp Val Leu Glu Arg Ala Lys Tyr Leu Ile Leu Asp Gly Ile Ala Cys
         35                  40                  45

Ala Trp Val Gly Ala Arg Val Pro Trp Ser Glu Lys Tyr Val Gln Ala
     50                  55                  60

Thr Met Ser Phe Glu Pro Pro Gly Ala Cys Arg Val Ile Gly Tyr Gly
 65                  70                  75                  80

Gln Lys Leu Gly Pro Val Ala Ala Ala Met Thr Asn Ser Ala Phe Ile
                 85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala Tyr Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270
```

Val Ala Gly Leu Gly Ser Phe Trp His Thr Phe Thr Ile Arg Ile Lys
            275                 280                 285

Leu Tyr Ala Cys Cys Gly Leu Val His Gly Pro Val Glu Ala Ile Glu
        290                 295                 300

Lys Leu Gln Arg Arg Tyr Pro Glu Leu Leu Asn Arg Ala Asn Leu Ser
305                 310                 315                 320

Asn Ile Arg His Val Tyr Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365

Leu Leu Ala Gln Phe Ser Glu Phe Asp Asp Asn Leu Glu Arg Pro Glu
    370                 375                 380

Val Trp Asp Leu Ala Arg Lys Val Thr Pro Ser His Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Val Thr Glu Thr Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
    450                 455                 460

Val Leu Ser Leu Asp Arg Leu Thr Asp Ile Thr Pro Leu Leu Glu Leu
465                 470                 475                 480

Leu Asn Cys Pro Val Lys Ser Pro Leu Val
                485                 490

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
atcgtcatga ccaagcaatc tg                                              22

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26
atcgtcatga ccaagcaatc tgcggaca                                        28

<210> SEQ ID NO 27
<211> LENGTH: 19
<212> TYPE: DNA
<213> ORGANISM: Artificial Sequence
<220> FEATURE:
<223> OTHER INFORMATION: reverse primer

<400> SEQUENCE: 27
gtcccgtcta ctcacacgc                                                  19

```
<210> SEQ ID NO 28
<211> LENGTH: 28
<212> TYPE: DNA
<213> ORGANISM: Artificial Sequence
<220> FEATURE:
<223> OTHER INFORMATION: reverse primer

<400> SEQUENCE: 28
tttagcggtg accatattcc taggccct                                    28

<210> SEQ ID NO 29
<211> LENGTH: 33
<212> TYPE: DNA
<213> ORGANISM: Artificial Sequence
<220> FEATURE:
<223> OTHER INFORMATION: reverse primer

<400> SEQUENCE: 29
ggcattttag cggtgaccat attcctaggc ccc                              33

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
atcgtcatga ccaagcaatc tg                                          22

<210> SEQ ID NO 31
<211> LENGTH: 16
<212> TYPE: DNA
<213> ORGANISM: Artificial Sequence
<220> FEATURE:
<223> OTHER INFORMATION: primer

<400> SEQUENCE: 31
tactggttcg ttagac                                                 16

<210> SEQ ID NO 32
<211> LENGTH: 28
<212> TYPE: DNA
<213> ORGANISM: Artificial Sequence
<220> FEATURE:
<223> OTHER INFORMATION: primer

<400> SEQUENCE: 32
atcgtcatga ccaagcaatc tgcggaca                                    28

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
tactggttcg ttagacgcct gt                                          22

<210> SEQ ID NO 34
<211> LENGTH: 28
<212> TYPE: DNA
<213> ORGANISM: Artificial Sequence
<220> FEATURE:
<223> OTHER INFORMATION: reverse primer

<400> SEQUENCE: 34
```
tcccggatcc ttataccagt ggcgattt                                                      28

<210> SEQ ID NO 35
<211> LENGTH: 18
<212> TYPE: DNA
<213> ORGANISM: Artificial Sequence
<220> FEATURE:
<223> OTHER INFORMATION: primer

<400> SEQUENCE: 35
aatatggtca ccgctaaa                                                                 18

<210> SEQ ID NO 36
<211> LENGTH: 33
<212> TYPE: DNA
<213> ORGANISM: Artificial Sequence
<220> FEATURE:
<223> OTHER INFORMATION: reverse primer

<400> SEQUENCE: 36
ccccggatcc ttataccagt ggcgatttta cgg                                                33

<210> SEQ ID NO 37
<211> LENGTH: 23
<212> TYPE: DNA
<213> ORGANISM: Artificial Sequence
<220> FEATURE:
<223> OTHER INFORMATION: primer

<400> SEQUENCE: 37
aatatggtca ccgctaaagt gcc                                                           23

<210> SEQ ID NO 38
<211> LENGTH: 19
<212> TYPE: DNA
<213> ORGANISM: Artificial Sequence
<220> FEATURE:
<223> OTHER INFORMATION: primer

<400> SEQUENCE: 38
ggtcttagcc gagcaaggc                                                                19

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ccagaatcgg ctcgttccg                                                                19

<210> SEQ ID NO 40
<211> LENGTH: 19
<212> TYPE: DNA
<213> ORGANISM: Artificial Sequence
<220> FEATURE:
<223> OTHER INFORMATION: reverse primer

<400> SEQUENCE: 40
gcgacactca tctgccctg                                                                19

<210> SEQ ID NO 41
<211> LENGTH: 19
<212> TYPE: DNA
<213> ORGANISM: Artificial Sequence
<220> FEATURE:
<223> OTHER INFORMATION: primer

<400> SEQUENCE: 41
cgctgtgagt agacgggac                                                   19

<210> SEQ ID NO 42
<211> LENGTH: 7113
<212> TYPE: DNA
<213> ORGANISM: Artificial Sequence
<220> FEATURE:
<223> OTHER INFORMATION: synthetically constructed sequence of vector
      pET-9971

<400> SEQUENCE: 42

| | | |
|---|---|---|
| atgaaacgag agaggatgct cacgatacgg gttactgatg atgaacatgc ccggttactg | 60 |
| gaacgttgtg agggtaaaca actggcggta tggatgcggc gggaccagag aaaaatcact | 120 |
| cagggtcaat gccagcgctt cgttaataca gatgtaggtg ttccacaggg tagccagcag | 180 |
| catcctgcga tgcagatccg aacataatg gtgcagggcg ctgacttccg cgtttccaga | 240 |
| ctttacgaaa cacggaaacc gaagaccatt catgttgttg ctcaggtcgc agacgttttg | 300 |
| cagcagcagt cgcttcacgt tcgctcgcgt atcggtgatt cattctgcta accagtaagg | 360 |
| caaccccgcc agcctagccg ggtcctcaac gacaggagca cgatcatgcg cacccgtggc | 420 |
| caggacccaa cgctgcccga tgcgccgc gtgcggctgc tggagatggc ggacgcgatg | 480 |
| gatatgttct gccaagggtt ggtttgcgca ttcacagttc tccgcaagaa ttgattggct | 540 |
| ccaattcttg gagtggtgaa tccgttagcg aggtgccgcc ggcttccatt caggtcgagg | 600 |
| tggcccggct ccatgcaccg cgacgcaacg cggggaggca gacaaggtat agggcggcgc | 660 |
| ctacaatcca tgccaacccg ttccatgtgc tcgccgaggc ggcataaatc gccgtgacga | 720 |
| tcagcggtcc agtgatcgaa gttaggctgg taagagccgc gagcgatcct tgaagctgtc | 780 |
| cctgatggtc gtcatctacc tgcctggaca gcatggcctg caacgcgggc atcccgatgc | 840 |
| cgccggaagc gagaagaatc ataatgggga aggccatcca gcctcgcgtc gcgaacgcca | 900 |
| gcaagacgta gcccagcgcg tcggccgcca tgccggcgat aatggcctgc ttctcgccga | 960 |
| aacgtttggt ggcgggacca gtgacgaagg cttgagcgag ggcgtgcaag attccgaata | 1020 |
| ccgcaagcga caggccgatc atcgtcgcgc tccagcgaaa gcggtcctcg ccgaaaatga | 1080 |
| cccagagcgc tgccggcacc tgtcctacga gttgcatgat aaagaagaca gtcataagtg | 1140 |
| cggcgacgat agtcatgccc cgcgcccacc ggaaggagct gactgggttg aaggctctca | 1200 |
| agggcatcgg tcgagatccc ggtgcctaat gagtgagcta acttacatta attgcgttgc | 1260 |
| gctcactgcc cgctttccag tcgggaaacc tgtcgtgcca gctgcattaa tgaatcggcc | 1320 |
| aacgcgcggg gagaggcggt ttgcgtattg ggcgccaggg tggtttttct tttcaccagt | 1380 |
| gagacgggca acagctgatt gcccttcacc gcctggccct gagagagttg cagcaagcgg | 1440 |
| tccacgctgg tttgccccag caggcgaaaa tcctgtttga tggtggttaa cggcgggata | 1500 |
| taacatgagc tgtcttcggt atcgtcgtat cccactaccg agatatccgc accaacgcgc | 1560 |
| agcccggact cggtaatggc gcgcattgcg cccagcgcca tctgatcgtt ggcaaccagc | 1620 |
| atcgcagtgg gaacgatgcc ctcattcagc atttgcatgg tttgttgaaa accggacatg | 1680 |
| gcactccagt cgccttcccg ttccgctatc ggctgaattt gattgcgagt gagatattta | 1740 |
| tgccagccag ccagacgcag acgcgccgag acagaactta atgggcccgc taacagcgcg | 1800 |
| atttgctggt gacccaatgc gaccagatgc tccacgccca gtcgcgtacc gtcttcatgg | 1860 |

```
gagaaaataa tactgttgat gggtgtctgg tcagagacat caagaaataa cgccggaaca    1920
ttagtgcagg cagcttccac agcaatggca tcctggtcat ccagcggata gttaatgatc    1980
agcccactga cgcgttgcgc gagaagattg tgcaccgccg ctttacaggc ttcgacgccg    2040
cttcgttcta ccatcgacac caccacgctg cacccagtt gatcggcgcg agatttaatc     2100
gccgcgacaa tttgcgacgg cgcgtgcagg ccagactgg aggtggcaac gccaatcagc     2160
aacgactgtt tgcccgccag ttgttgtgcc acgcggttgg gaatgtaatt cagctccgcc    2220
atcgccgctt ccactttttc ccgcgttttc gcagaaacgt ggctggcctg gttcaccacg    2280
cgggaaacgg tctgataaga gacaccggca tactctgcga catcgtataa cgttactggt    2340
ttcacattca ccaccctgaa ttgactctct tccgggcgct atcatgccat accgcgaaag    2400
gttttgcgcc attcgatggt gtccgggatc tcgacgctct cccttatgcg actcctgcat    2460
taggaagcag cccagtagta ggttgaggcc gttgagcacc gccgccgcaa ggaatggtgc    2520
atgcaaggag atggcgccca acagtccccc ggccacgggg cctgccacca tacccacgcc    2580
gaaacaagcg ctcatgagcc cgaagtggcg agcccgatct tccccatcgg tgatgtcggc    2640
gatataggcg ccagcaaccg cacctgtggc gccggtgatg ccggcacga tgcgtccggc     2700 gtagaggatc gagatctcga tcccgcgaaa ttaatacgac tcactatagg ggaattgtga    2760
gcggataaca attcccctct agaaataatt ttgtttaact ttaagaagga gatataccat    2820
gaccaaacaa agtgctgatt ctaacgccaa gagtggcgtg accgcagaaa tttgccattg    2880
ggcgtcgaat ctggcgacgg acgatatccc gtccgacgtc ctggaacgcg ccaagtatct    2940
gattctggac ggtattgcat gtgcttgggt cggggcgcgc gtaccgtggt cggaaaaata    3000
cgtgcaagcc actatgagct ttgaaccgcc gggcgcatgc cgtgttattg gttacggtca    3060
aaagctgggg ccggtcgcgg cggccatgac aaatagcgct tttatccaag ccacagaact    3120
ggacgattat cacagtgagg cgccgctgca ctcagcgtcc attgtactgc cggcagtatt    3180
cgcagcttca gaggttctgg ccgaacaggg taaaacgatc agcggcattg acgttatcct    3240
ggctgcgatt gtgggtttcg agtctggggcc gcgtattggc aaggcaattt acggtagtga    3300
tctgctgaac aacggctggc attgtggtgc agtatacggg gcaccggcgg gggcgctggc    3360
tactggtaaa ctgctggggc tgacaccgga ctcgatggag gacgcactgg gcatcgcgtg    3420
tacccaagcg tgcggtctga tgtccgcaca atacggcggt atggtgaagc gtgtccaaca    3480
cggttttgct gcccgtaacg gtctgctggg tggcctgctg gcttacggtg ggtacgaagc    3540
gatgaaaggc gtgctggaac gcagttacgg tgggttcctg aagatgttta cgaaaggcaa    3600
cggtcgcgaa ccgccgtaca agaggaaga agttgttgcc ggtctgggct ccttttggca    3660 cactttttact attcgtatca agctgtacgc atgctgtggg ctggtgcacg gtccggtgga    3720
agcaattgaa aagctgcagc gtcgctaccc ggagctgctg aaccgcgcga atctgtctaa    3780
cattcgtcac gtgtacgttc agctgtcgac tgcgagcaac agtcactgcg gttgatacc     3840 ggaagaacgc ccgattagct cgatcgccgg tcagatgtct gtagcctata ttctggcggt    3900
ccaactggtt gatcagcaat gcctgctggc acaattttct gagtttgacg ataacctgga    3960
acgtccggaa gtgtgggatc tggcccgtaa agtcacaccg agtcacagcg aggagttcga    4020
ccaggatgga aattgcctga gtgctggtcg tgttcgtatc gagttcaacg acggctcgtc    4080
ggtcaccgag actgtcgaaa agccgctggg tgtgaaagaa ccgatgccga atgaacgtat    4140
tctgcacaag tatcgcacac tggcggggag cgttactgac gagagccgtg taaaggaaat    4200
cgaagatctg gtcctgtcac tggaccgcct gacggatatt accccgctgc tggagctgct    4260
```

```
gaactgtccg gttaaatccc cgctggtgta aggatccggc tgctaacaaa gcccgaaagg   4320
aagctgagtt ggctgctgcc accgctgagc aataactagc ataacccctt ggggcctcta   4380
aacgggtctt gaggggtttt ttgctgaaag gaggaactat atccggatat cccgcaagag   4440
gcccggcagt accggcataa ccaagcctat gcctacagca tccagggtga cggtgccgag   4500
gatgacgatg agcgcattgt tagatttcat acacggtgcc tgactgcgtt agcaatttaa   4560
ctgtgataaa ctaccgcatt aaagcttatc gatgataagc tgtcaaacat gagaattctt   4620
gaagacgaaa gggcctcgtg atacgcctat ttttataggt taatgtcatg ataataatgg   4680
tttcttagac gtcaggtggc acttttcggg gaaatgtgcg cggaacccct atttgtttat   4740
ttttctaaat acattcaaat atgtatccgc tcatgagaca ataaccctga taaatgcttc   4800
aataatattg aaaaaggaag agtatgagta ttcaacattt ccgtgtcgcc cttattccct   4860 ttttgcggc attttgcctt cctgtttttg ctcacccaga aacgctggtg aaagtaaaag   4920
atgctgaaga tcagttgggt gcacgagtgg gttacatcga actggatctc aacagcggta   4980
agatccttga gagttttcgc cccgaagaac gttttccaat gatgagcact tttaaagttc   5040
tgctatgtgg cgcggtatta tcccgtgttg acgccgggca agagcaactc ggtcgccgca   5100
tacactattc tcagaatgac ttggttgagt actcaccagt cacagaaaag catcttacgg   5160
atggcatgac agtaagagaa ttatgcagtg ctgccataac catgagtgat aacactgcgg   5220
ccaacttact tctgacaacg atcggaggac cgaaggagct aaccgctttt ttgcacaaca   5280
tgggggatca tgtaactcgc cttgatcgtt gggaaccgga gctgaatgaa gccataccaa   5340
acgacgagcg tgacaccacg atgcctgcag caatggcaac aacgttgcgc aaactattaa   5400
ctggcgaact acttactcta gcttcccggc aacaattaat agactggatg gaggcggata   5460
aagttgcagg accacttctg cgctcggccc ttccggctgg ctggtttatt gctgataaat   5520
ctggagccgg tgagcgtggg tctcgcggta tcattgcagc actggggcca gatggtaagc   5580
cctcccgtat cgtagttatc tacacgacgg ggagtcaggc aactatggat gaacgaaata   5640
gacagatcgc tgagataggt gcctcactga ttaagcattg gtaactgtca gaccaagttt   5700
actcatatat actttagatt gatttaaaac ttcatttta atttaaaagg atctaggtga   5760
agatcctttt tgataatctc atgaccaaaa tcccttaacg tgagttttcg ttccactgag   5820
cgtcagaccc cgtagaaaag atcaaaggat cttcttgaga tcctttttt ctgcgcgtaa   5880 tctgctgctt gcaaacaaaa aaaccaccgc taccagcggt ggtttgtttg ccggatcaag   5940
agctaccaac tcttttttcg aaggtaactg gcttcagcag agcgcagata ccaaatactg   6000
tccttctagt gtagccgtag ttaggccacc acttcaagaa ctctgtagca ccgcctacat   6060
acctcgctct gctaatcctg ttaccagtgg ctgctgccag tggcgataag tcgtgtctta   6120
ccgggttgga ctcaagacga tagttaccgg ataaggcgca gcggtcgggc tgaacggggg   6180
gttcgtgcac acagcccagc ttggagcgaa cgacctacac cgaactgaga tacctacagc   6240
gtgagctatg agaaagcgcc acgcttcccg aagggagaaa ggcggacagg tatccggtaa   6300
gcggcagggt cggaacagga gagcgcacga gggagcttcc agggggaaac gcctggtatc   6360
tttatagtcc tgtcgggttt cgccacctct gacttgagcg tcgatttttg tgatgctcgt   6420
caggggggcg gagcctatgg aaaaacgcca gcaacgcggc cttttacgg ttcctggcct   6480 tttgctggcc ttttgctcac atgttctttc ctgcgttatc ccctgattct gtggataacc   6540
gtattaccgc ctttgagtga gctgataccg ctcgccgcag ccgaacgacc gagcgcagcg   6600
agtcagtgag cgaggaagcg gaagagcgcc tgatgcggta ttttctcctt acgcatctgt   6660
```

-continued

```
gcggtatttc acaccgcata tatggtgcac tctcagtaca atctgctctg atgccgcata    6720
gttaagccag tatacactcc gctatcgcta cgtgactggg tcatggctgc gccccgacac    6780
ccgccaacac ccgctgacgc gccctgacgg gcttgtctgc tcccggcatc cgcttacaga    6840
caagctgtga ccgtctccgg gagctgcatg tgtcagaggt tttcaccgtc atcaccgaaa    6900
cgcgcgaggc agctgcggta aagctcatca gcgtggtcgt gaagcgattc acagatgtct    6960
gcctgttcat ccgcgtccag ctcgttgagt ttctccagaa gcgttaatgt ctggcttctg    7020
ataaagcggg ccatgttaag ggcggttttt tcctgtttgg tcactgatgc ctccgtgtaa    7080
gggggatttc tgttcatggg ggtaatgata ccg                                 7113
```